US008865178B2

(12) United States Patent
Galili

(10) Patent No.: US 8,865,178 B2
(45) Date of Patent: *Oct. 21, 2014

(54) COMPOSITIONS AND METHODS FOR WOUND HEALING

(75) Inventor: Uri Galili, Shrewsbury, MA (US)

(73) Assignee: University of Massachusetts, Boston, MA (US)

( * ) Notice: Subject to any disclaimer, the term of this patent is extended or adjusted under 35 U.S.C. 154(b) by 140 days.

This patent is subject to a terminal disclaimer.

(21) Appl. No.: 13/390,292

(22) PCT Filed: Aug. 17, 2010

(86) PCT No.: PCT/US2010/045747
§ 371 (c)(1),
(2), (4) Date: May 1, 2012

(87) PCT Pub. No.: WO2011/022389
PCT Pub. Date: Feb. 24, 2011

(65) Prior Publication Data
US 2012/0207819 A1 Aug. 16, 2012

Related U.S. Application Data

(63) Continuation-in-part of application No. 12/542,377, filed on Aug. 17, 2009, now Pat. No. 8,084,057, which is a continuation-in-part of application No. PCT/US2008/008731, filed on Jul. 17, 2008.

(60) Provisional application No. 60/961,047, filed on Jul. 17, 2007.

(51) Int. Cl.
| A61K 39/12 | (2006.01) |
| A61K 39/00 | (2006.01) |
| A61K 39/395 | (2006.01) |
| C07K 16/00 | (2006.01) |
| A61K 47/48 | (2006.01) |
| A61K 9/00 | (2006.01) |

(52) U.S. Cl.
CPC ....... *A61K 47/48815* (2013.01); *A61K 47/4823* (2013.01); *A61K 9/0019* (2013.01); *A61K 9/0014* (2013.01); *Y10S 424/816* (2013.01)
USPC .................. 424/184.1; 424/155.1; 424/156.1; 424/218.1; 424/277.1; 424/816; 530/387.1

(58) Field of Classification Search
None
See application file for complete search history.

(56) References Cited

U.S. PATENT DOCUMENTS

| 5,705,188 | A | 1/1998 | Junichi et al. ................. 424/450 |
| 6,361,775 | B1 | 3/2002 | Galili et al. ................. 424/184.1 |
| 8,084,057 | B2 | 12/2011 | Galili .......................... 424/450 |
| 8,440,198 | B2 * | 5/2013 | Galili ........................ 424/184.1 |
| 2004/0043006 | A1 | 3/2004 | Badylak et al. .............. 424/93.7 |
| 2004/0234507 | A1 | 11/2004 | Stone ........................... 424/93.7 |
| 2005/0112118 | A1 | 5/2005 | Cimbora et al. ........... 424/143.1 |
| 2005/0112141 | A1 | 5/2005 | Terman ...................... 424/192.1 |
| 2006/0258562 | A1 | 11/2006 | Tennenbaum ............... 514/44 R |
| 2010/0226965 | A1 | 9/2010 | Galili ........................... 424/448 |

FOREIGN PATENT DOCUMENTS

| WO | WO 97/30731 | 8/1997 |
| WO | WO/2009/011883 | 1/2009 |

OTHER PUBLICATIONS

Abdel-Motal, et al., "Increased immunogenicity of HIV gp120 engineered to express α-gal epitopes." *J. Virol.*, 80:6943-6951 (2006).
Abdel-Motal, et al., "Mechanism for increased immunogenicity of vaccines that form in vivo immune complexes with the natural anti-Gal antibody." *Vaccine*, 27:3072-3082 (2009).
Aderem and Underhill, "Mechanisms of Phagocytosis in Macrophages." *Annu Rev Immunol*, 17:593-623 (1999).
Aguiar-Passeti, et al., "Epithelioid cells from foreign-body granuloma selectively express the calcium-binding protein MRP-14, a novel down-regulatory molecule of macrophage activation." *J Leukoc Biol.*, 62:852-858 (1997).
Arras et al., "Monocyte activation in angiogenesis and collateral growth in the rabbit hindlimb" *J Clin Invest.*, 101(1):40-50 (1998).
Bryant, et al., "Mediation of Post-Surgical Wound Healing by Macrophages." *Prog Clin Biol Res*, 266:273-290 (1988).
Clark, "Basics of Cutaneous Wound Repair." *J Dermatol Surg Oncol*, 19(8):693-706 (1993).
Collins, et al., "Cardiac Xenografts between Primate Species Provide Evidence for the Importance of the Alpha-Galactosyl Determinant in Hyperacute Rejection." *J Immunol*, 154(10):5500-5510 (1995).
Crainic et al., "ABO tissue antigens of Egyptian mummies." *Forensic Sci Int.* 43:113-124 (1989).
Dabrowski, et al., "Immunochemistry of I/I-Active Oligo- and Polyglycosylceramides from Rabbit Erythrocyte Membranes. Determination of Branching Patterns of a Ceramide Pentadecasaccharide by 1H Nuclear Magnetic Resonance." *J Biol Chem*, 259(12):7648-7651 (1984).
Danon, et al., "Treatment of Human Ulcers by Application of Macrophages Prepared from a Blood Unit." *Exp Gerontol*, 32(6):633-641 (1997).

(Continued)

*Primary Examiner* — Michail Belyavskyi
(74) *Attorney, Agent, or Firm* — Medlen & Carroll, LLP

(57) ABSTRACT

The present invention is related to the field of wound healing or tissue regeneration due to disease (i.e., for example, cardiovascular diseases, osetoarthritic diseases, or diabetes). In particular, the present invention provides compositions and methods comprising molecules with linked α-gal epitopes for induction of recruitment of macrophages localized within or surrounding damaged tissue. The recruited macrophages recruit stem cells and promote the repair and regeneration of the treated injured tissue. In some embodiments, the present invention provides treatments for tissue repair in normal subjects and in subjects having impaired healing capabilities, such as diabetic and aged subjects. In some embodiments, the present invention provides treatments for injured tissues such as brain, peripheral nerve, heart muscle, skeletal muscle, cartilage, bone, gastrointestinal tract and dysfunctional endocrine tissues.

9 Claims, 34 Drawing Sheets

(56) References Cited

OTHER PUBLICATIONS

Dinarello, "Biology of Interleukin 1." *Faseb J*, 2(2):108-115 (1988).
DiPietro, "Wound Healing: The Role of the Macrophage and Other Immune Cells." *Shock*, 4(4):233-240 (1995).
Duffield, et al., "Selective depletion of macrophages reveals distinct, opposing roles during liver injury and repair." *J Clin Invest.*, 115:56-65 (2005).
Egge, et al., "Immunochemistry of Pi-active oligo- and polyglycosylceramides from rabbit erythrocyte membranes. Characterization of linear, di-, and triantennary neolactoglycosphingolipids." *J. Biol. Chem.*, 260:4927-4935 (1985).
Eisenberg, et al., "Bone Marrow Cells Transdifferentiate to Cardiomyocytes When Introduced into the Embryonic Heart." *Stem Cells*, 24(5):1236-1245 (2006).
Eto, et al., "Chemistry of Lipid of the Posthemyolytic Residue or Stroma of Erythrocytes. Xvi. Occurrence of Ceramide Pentasaccharide in the Membrane of Erythrocytes and Reticulocytes of Rabbit." *J Biochem*, 64(2):205-213 (1968).
Frangogiannis, "Targeting the Inflammatory Response in Healing Myocardial Infarcts." *Curr Med Chem*, 13(16):1877-1893 (2006).
Galili, et al., "A Unique Natural Human IgG Antibody with Anti-α-Galactosyl Specificity." *J Exp Med*, 160(5):1519-1531 (1984).
Galili, et al., "Human natural anti-α-galactosyl IgG. II. The specific recognition of $\alpha(1\text{-}3)$-linked galactose residues." *J. Exp. Med.*, 162:573-82 (1985).
Galili, et al., "Identification of Erythrocyte Galα1-3Gal Glycosphingolipids with a Mouse Monoclonal Antibody, Gal-13." *J Biol Chem*, 262(10):4683-4688 (1987a).
Galili, et al. "Evolutionary Relationship between the Natural Anti-Gal Antibody and the Galα1→3Gal Epitope in Primates." *Proc Natl Acad Sci U S A* 84(5):1369-1373 (1987b).
Galili, et al., "Interaction between Human Natural Anti-α-Galactosyl Immunoglobulin G and Bacteria of the Human Flora." *Infect Immun*, 56(7):1730-1737 (1988a).
Galili, et al., "Man, Apes, and Old World Monkeys Differ from Other Mammals in the Expression of α-Galactosyl Epitopes on Nucleated Cells." *J Biol Chem*, 263(33):17755-17762 (1988b).
Galili, "Evolution and Pathophysiology of the Human Natural Anti-α-Galactosyl IgG(Anti-Gal) Antibody." *Springer Seminars in Immunopathology*, 15(2-3):155-171 (1993a).
Galili, "Interaction of the Natural Anti-Gal Antibody with α-Galactosyl Epitopes: A Major Obstacle for Xenotransplantation in Humans." *Immunol Today*, 14(10):480-482 (1993b).
Galili, et al., "Increased anti-Gal activity in diabetic patients transplanted with fetal porcine islet cell clusters." *Transplantation*, 59:1549-1556 (1995).
Galili, et al., "A Sensitive Assay for Measuring α-Gal Epitope Expression on Cells by a Monoclonal Anti-Gal Antibody." *Transplantation*, 65(8):1129-1132 (1998).
Galili, "Autologous Tumor Vaccines Processed to α-Gal Epitopes: A Practical Approach to Immunotherapy in Cancer." *Cancer Immunology, Immunotherapy*, 53(11):935-945 (2004a).
Galili, "The α-gal epitope and the anti-Gal antibody in xenotransplantation and in cancer immunotherapy." *Immunology and Cell Biology*, 83:674-686 (2005).
Galili, et al., "Intratumoral injection of α-gal glycolipids induces xenograft-like destruction and conversion of lesions into endogenous vaccines." *J. Immunol.*, 178:4676-4687 (2007).
Galili, et al., "Accelerated healing of skin burns by anti-Gal/α-gal liposomes interaction." *Burns*, 36:239-251 (2010).
Hamadeh, et al., "Human secretions contain IgA, IgG and IgM anti-Gal (anti-.alpha.-galactosyl) antibodies." *Clin. Diagnos. Lab. Immunol.*, 2:125-131 (1995).
Hanfland, et al., "Structure Elucidation of Blood Group B-Like and I-Active Ceramide Eicosa-and Pentacosasaccharides from Rabbit Erythrocyte Membranes by Combined Gas Chromatography-Mass Spectrometry; Electron-Impact and Fast-Atom-Bombardment Mass Spectrometry; and Two-Dimensional Correlated, Relayed-Coherence Transfer, and Nuclear Overhauser Effect 500-MHz $^{1}$H-N.M.R. Spectroscopy." *Carbohydr Res*, 178:1-21 (1988).

Honma, et al., "Isolation and Partial Structural Characterization of Macroglycolipid from Rabbit Erythrocyte Membranes." *J Biochem*, 90(4):1187-1196 (1981).
Jeschke, et al., "The combination of IGF-I and KGF cDNA improves dermal and epidermal regeneration by increased VEGF expression and neovascularization." *Gene Ther.*, 14:1235-1242 (2007).
Kelley, et al., "Influence of hypercholesterolemia and cholesterol accumulation on rabbit carrageenan granuloma macrophage activation." *Am J. Pathol.*, 131:539-546 (1988).
Knighton and Fiegel, "The Macrophages: Effector Cell Wound Repair." *Prog Clin Biol Res*, 299:217-226 (1989).
LaTemple, et al., "Increased immunogenicity of tumor vaccines complexed with anti-Gal: Studies in knockout mice for α1,3galactosyltranferase." *Cancer Res.*, 59:3417-3423 (1999).
Leibovich and Ross, "The Role of the Macrophage in Wound Repair. A Study with Hydrocortisone and Antimacrophage Serum." *Am J Pathol*, 78(1):71-100 (1975).
Manches, et al., "Anti-Gal mediated targeting of human B lymphoma cells to antigen-presenting cells: a potential method for immunotherapy with autologous tumor cells." *Haematologica*, 90:625-634 (2005).
Mateo, et al., "Interleukin-6 Activity in Wounds." *Am J Physiol*, 266(6 Pt 2):R1840-1844 (1994).
Nathan, "Secretory Products of Macrophages." *J Clin Invest*, 79(2):319-326 (1987).
Orenstein, et al., "Treatment of Deep Sternal Wound Infections Post-Open Heart Surgery by Application of Activated Macrophage Suspension." *Wound Repair Regen*, 13(3):237-242 (2005).
Ott, et al., "Inhalation of Carbon Monoxide Prevents Liver Injury and Inflammation Following Hind Limb Ischemia/Reperfusion." *FASEB J*, 19(1):106-108 (2005).
Parker, et al., "Characterization and affinity isolation of xenoreactive human natural antibodies" *J. Immunol.* 153(8):3791-803 (1994).
Plock, et al., "Hemoglobin vesicles improve wound healing and tissue survival in critically ischemic skin in mice." *Am J Physiol Heart Circ Physiol.*, 297:H905-910 (2009).
Rappolee and Werb, "Macrophage-Derived Growth Factors." *Curr Top Microbiol Immunol*, 181:87-140 (1992).
Sandrin, et al., "Natural Human Anti-Galα(1,3)Gal Antibodies React with Human Mucin Peptides." *Glycoconj J*, 14(1):97-105 (1997).
Schirmer, et al., "Effective Antiplatelet Therapy Does Not Prolong Transgenic Pig to Baboon Cardiac Xenograft Survival." *Xenotransplantation*, 11(5):436-443 (2004).
Schmid, et al., "The Disulfide Bonds of $\alpha_1$-Acid Glycoprotein." *Biochemistry*, 13(13):2694-2697 (1974).
Sen, et al., "Human skin wounds: a major and snowballing threat to public health and the economy." *Wound Repair Regen.*, 17:763 (2009).
Seta and Kuwana, "Human Circulating Monocytes as Multipotential Progenitors." *Keio J Med*, 56(2):41-47 (2007).
Singer and Clark, "Cutaneous Wound Healing." *N Engl J Med*, 341(10):738-746 (1999).
Stein and Keshav, "The Versatility of Macrophages." *Clinical & Experimental Allergy*, 22(1):19-27 (1992).
Stellner, et al., "Determination of Aminosugar Linkages in Glycolipids by Methylation. Aminosugar Linkages of Ceramide Pentasaccharides of Rabbit Erythrocytes and of Forssman Antigen." *Arch Biochem Biophys*, 155(2):464-472 (1973).
Stone, et al., "Replacement of Human Anterior Cruciate Ligaments with Pig Ligaments: A Model for Anti-Non-Gal Antibody Response in Long-Term Xenotransplantation." *Transplantation*, 83(2):211-219 (2007).
Tanemura, et al., "Differential Immune Responses to α-gal Epitopes on Xenografts and Allografts: Implications for Accommodation in Xenotransplantation." *J Clin Invest*, 105(3):301-310 (2000).
Thall, et al., "Oocyte Galα1,3Gal Epitopes Implicated in Sperm Adhesion to the Zona Pellucida Glycoprotein Zp3 Are Not Required for Fertilization in the Mouse." *J Biol Chem*, 270(37):21437-21440 (1995).
Vorauer-Uhl, et al., "Reepithelialization of experimental scalds effected by topically applied superoxide dismutase: controlled animal studies." *Wound Repair Regen.* 10:366-371 (2002).

(56) References Cited

OTHER PUBLICATIONS

Wang, et al., "Macrophages are a significant source of type 1 cytokines during mycobacterial infection." *J Clin Invest.* 103(7):1023-1029 (1999).

Wood, et al., "Immunochemical Studies of the Combining Sites of the Two Isolectins, A4 and B4, Isolated from *Bandeiraea simplicifolia.*" *Arch Biochem Biophys*, 198(1):1-11 (1979).

Zhong, et al., "Improvement in Human Decay Accelerating Factor Transgenic Porcine Kidney Xenograft Rejection with Intravenous Administration of GAS914, a Polymeric Form of αgal." *Transplantation*, 75(1):10-19 (2003).

Feldman, et al., "Anti-TNF alpha therapy is useful in rheumatoid arthritis and Crohn's disease: analysis of the mechanism of action predicts utility in other diseases." *Transplant. Proc.*, 30:4126-4127 (1998).

Cochlovius, et al., "Therapeutic Antibodies." *Modern Drug Discovery*, 33-38 (2003).

Chazaud, et al., "Satellite cells attract monocytes and use macrophages as a support to escape apoptosis and enhance muscle growth." *J. Cell Biol.*, 163: 1133-1143 (2003).

Duffield, "The inflammatory macrophage: a story of Jekyll and Hyde." *Clinical Science*, 104: 27-38 (2003).

Leor, et al., "Ex Vivo Activated Human Macrophages Improve Healing, Remodeling, and Function of the Infarcted Heart." *Circulation*, 114: I-94-I-100 (2006).

Rapalino, et al., "Implantation of stimulated homologous macrophages results in partial recovery of paraplegic rats." *Nature Med.*, 4: 814-821 (1998).

Wigglesworth, et al., "Rapid recruitment and activation of macrophages by anti-Gal/α-Gal liposome interaction accelerates wound healing." *J. Immunol.*, pp. 4422-4432 (2011).

Abbas & Lichtman, *Cellular and Molecular Immunology.* Publ. Saunders, Fifth Ed., Chapter 12, entitled "Innate Immunity." p. 293 (2003).

Abbas & Lichtman, *Cellular and Molecular Immunology.* Publ. Saunders, Fifth Ed., Chapter 14, entitled "Effector Mechanisms of Immune Responses," pp. 326-333 (2003).

Peakman & Vergani, *Basic and Clinical Immunology.* Publ. Churchill Livingstone, pp. 13-17 (1997).

GenBank: AAA72968.1 (1990).

GenBank: AAA73037.1 (1991).

Joziasse, et al. "α-1→3-Galactosyltransferase: The Use of Recombinant Enzyme for the Synthesis of Alpha-Galactosylated Glycoconjugates." *Eur J Biochem*, 191(1):75-83 (1990).

\* cited by examiner

A. Original muscle

B. Muscle 4 days post ischemia

C. Muscle 4 days post ischemia treated with α-gal liposomes

C

COMPOSITIONS AND METHODS FOR WOUND HEALING

This application is the U.S. National stage filing of PCT Application No. PCT/US2010/45747, filed on Aug. 17, 2010, which is a continuation-in-part of, and claims priority to, U.S. patent application Ser. No. 12/542,377, filed on Aug. 17, 2009, that issued on Dec. 27, 2011 as U.S. Pat. No. 8,084,057, which is a continuation-in-part of, and claims priority to, PCT/US2008/008731, filed on Jul. 17, 2008, now abandoned, which claims priority under 35 U.S.C. §119(e) to U.S. provisional Patent Application Ser. No. 60/961,047, filed on Jul. 17, 2007, each of which is herein incorporated by reference in its entirety.

FIELD OF INVENTION

The present invention is related to the field of wound healing. In particular, the present invention provides compositions and methods comprising molecules with linked α-gal epitopes for induction of an inflammatory response localized within or surrounding damaged tissue. In some embodiments, the present invention provides treatments for tissue repair and regeneration in normal subjects and in subjects having impaired healing capabilities, such as diabetic and aged subjects.

BACKGROUND OF THE INVENTION

The inflammatory phase plays a critical role in wound healing regardless of the cause of the tissue damage. In addition to the destroying invading microbes, the inflammatory process is an integral part of the tissue repair process. Neutrophils are the first immune cells to arrive at the wound site where they phagocytose microbial agents and mediate wound debridement. Macrophages migrate into the wound two to three days post injury and become the predominant cell population before fibroblast migration and replication takes place. Compositions and methods to accelerate the pace and/or extent of wound healing are desirable, particularly in individuals with impaired healing capabilities, such as diabetic and aged individuals. Thus, there is a need for methods and compositions that promote healing in both external and internal wounds.

SUMMARY OF THE INVENTION

The present invention is related to the field of wound healing. In particular, the present invention provides compositions and methods comprising molecules with linked α-gal epitopes for induction of an inflammatory response localized within or surrounding damaged tissue and promotion of healing and repair of the injured tissue. In some embodiments, the present invention provides treatments for tissue repair in normal subjects and in subjects having impaired healing capabilities, such as diabetic and aged subjects.

In one embodiment, the present invention contemplates a method, comprising: a) providing; i) a subject having endogenous anti-Gal antibody, wherein the subject has an injured tissue; and ii) a preparation comprising an α-gal epitope having a terminal α-galactosyl; and b) applying said preparation to said tissue under conditions such that healing of said injured tissue is accelerated. In one embodiment, the tissue is an internal tissue. In one embodiment, the terminal α-galactosyl is selected from the group consisting of Galα1-3Gal, Galα1-2Gal, Galα1-6Gal, α-galactose sugar units capable of binding anti-Gal antibodies and α-gal epitope mimicking peptides linked to a macromolecule backbone or to another linker and they are capable of binding the anti-Gal antibody. In one embodiment, the α-gal epitope is soluble. In one embodiment, the α-gal epitope is attached to a molecule selected from the group consisting of a natural or synthetic glycolipid, glycoprotein, proteoglycan and a glycopolymer. In one embodiment, the preparation comprises α-gal liposomes. In one embodiment, the α-gal liposomes further comprise anti-Gal antibodies. In one embodiment, the preparation further comprises an injury care device selected from, but not limited to, the group consisting of syringes, adhesive bands, compression bandages, wound dressings, sponges, gels, ointments, creams, suspensions, solutions, semi-permeable films, plasma clots, fibrin clots and processed allogeneic and xenogeneic tissues used for wound healing and tissue regeneration. In one embodiment, the device comprises physiological compositions including, but not limited to, solutions, suspensions, emulsions, creams, ointments, aerosol sprays, collagen containing substances, stabilizers, drops, matrix-forming substances, foams and/or dried preparation. In one embodiment, the preparation further comprises anti-Gal antibodies bound to said α-gal liposomes. In one embodiment, the injured tissue is selected from the group consisting of skin tissue brain tissue, nerve tissue, eye tissue, gastrointestinal tissue, muscle tissue, heart tissue, cartilage tissue, bone tissue, connective tissue, endocrine glands and/or vascular tissue. In one embodiment, the preparation comprises α-gal liposomes.

In one embodiment, the present invention contemplates a method, comprising: a) providing; i) a diabetic subject having endogenous anti-Gal antibody, wherein said subject has an injured pancreas such that insulin production is impaired; and ii) a preparation comprising an α-gal epitope having a terminal α-galactosyl; and b) applying said preparation to said pancreas, thereby creating regenerated Langerhans Islet cells. In one embodiment, the terminal α-galactosyl is selected from the group consisting of Galα1-3Gal, Galα1-2Gal, Galα1-6Gal, and α-galactose sugar units capable of binding anti-Gal antibodies. In one embodiment, the α-gal epitope is soluble. In one embodiment, the α-gal epitope is bound to a molecule selected from the group consisting of a natural or synthetic glycolipid, glycoprotein, and a glycopolymer. In one embodiment, the preparation comprises α-gal epitope mimicking peptides linked to a macromolecule backbone or to another linker and they are capable of binding the anti-Gal antibody. In one embodiment, the preparation further comprises α-gal liposomes. In one embodiment, the α-gal liposomes further comprise anti-Gal antibodies bound to α-gal liposomes. In one embodiment, the preparation further comprises an injury care device selected from the group consisting of syringes, adhesive bands, compression bandages, wound dressings, sponges, gels, ointments, creams, suspensions, solutions, semi-permeable films, plasma clots, fibrin clots and processed allogeneic and xenogeneic tissues used for wound healing and tissue regeneration. In one embodiment, the device comprises physiological compositions including, but not limited to, solutions, suspensions, emulsions, creams, ointments, aerosol sprays, collagen containing substances, stabilizers, drops, matrix-forming substances, foams and/or dried preparation. In one embodiment, the regenerated Langerhans Islet cells produce insulin.

In one embodiment, the present invention contemplates a method, comprising: a) providing; i) a subject having endogenous anti-Gal antibody and having an injured tissue selected from the group consisting of a peripheral nerve, a spinal cord, and a blood vessel. ii) a device comprising a biodegradable or non-biodegradable sheet comprising a preparation comprising an α-gal epitope having a terminal α-galactosyl; and b) wrapping said sheet around said injured tissue under conditions such that regeneration of said injured tissue is accelerated. In one embodiment, the terminal α-galactosyl is selected from the group consisting of Galα1-3Gal, Galα1-2Gal, Galα1-6Gal and any α-galactose sugar units capable of binding anti-Gal antibodies. In one embodiment, the α-gal epitope is soluble. In one embodiment, the α-gal epitope is bound to a molecule selected from the group consisting of a natural or synthetic glycolipid, glycoprotein, and a glycopolymer. In one embodiment, the preparation comprises α-gal epitope mimicking peptides linked to a macromolecule backbone or to another linker and they are capable of binding the anti-Gal antibody. In one embodiment, the preparation comprises α-gal liposomes. In one embodiment, the preparation further comprises anti-Gal antibodies bound to said α-gal liposomes. In one embodiment, the sheet is selected from the group consisting of a collagen sheet and a synthetic sheet.

In one embodiment, the present invention contemplates a method, comprising: a) providing: i) a subject having endogenous anti-Gal antibody; ii) damaged brain tissue; and iii) a preparation comprising an α-gal epitope having a terminal galactosyl; b) applying said preparation to said damaged brain tissue to produce treated brain tissue. In further embodiments, said terminal α-galactosyl is selected from the group consisting of Galα1-3Gal and Galα1-6Gal. In still further embodiments, said α-gal epitope is part of a molecule selected from the group consisting of a glycolipid, a glycoprotein, proteoglycan and a glycopolymer. In some embodiments, the preparation comprises α-gal epitope mimicking peptides linked to a macromolecule backbone or to another linker and they are capable of binding the anti-Gal antibody. In additional embodiments, said glycolipid comprises α-gal liposomes. In some embodiments, said applying is under conditions such that complement activation within or adjacent to said damaged tissue is enhanced. In further embodiments, said complement activation comprises production of C5a, C4a and C3a. In still further embodiments, said applying is under conditions such that neutrophil recruitment within or adjacent to said injured tissue is enhanced. In additional embodiments, said applying is under conditions such that monocyte and macrophage recruitment within or adjacent to said injured tissue is enhanced. In some embodiments, said applying is under conditions such that repair of said injured tissue is accelerated.

In one embodiment, the present invention contemplates a method, comprising: a) providing: i) a subject having endogenous anti-Gal antibody; ii) damaged skeletal muscle tissue; and iii) a preparation comprising an α-gal epitope having a terminal galactosyl; b) applying said preparation to said damaged skeletal muscle to produce treated skeletal muscle tissue. In further embodiments, said terminal α-galactosyl is selected from the group consisting of Galα1-3Gal and Galα1-6Gal. In still further embodiments, said α-gal epitope is part of a molecule selected from the group consisting of a glycolipid, a glycoprotein, proteoglycan and a glycopolymer. In some embodiments, the preparation comprises α-gal epitope mimicking peptides linked to a macromolecule backbone or to another linker and they are capable of binding the anti-Gal antibody. In additional embodiments, said glycolipid comprises α-gal liposomes. In some embodiments, said applying is under conditions such that complement activation within or adjacent to said damaged tissue is enhanced. In further embodiments, said complement activation comprises production of C5a, C4a and C3a. In still further embodiments, said applying is under conditions such that neutrophil recruitment within or adjacent to said injured tissue is enhanced. In additional embodiments, said applying is under conditions such that monocyte and macrophage recruitment within or adjacent to said injured tissue is enhanced. In some embodiments, said applying is under conditions such that repair of said injured tissue is accelerated.

In one embodiment, the present invention contemplates a method, comprising: a) providing: i) a subject having endogenous anti-Gal antibody; ii) damaged pancreatic tissue; and iii) a preparation comprising an α-gal epitope having a terminal galactosyl; b) applying said preparation to said damaged pancreatic tissue to produce treated pancreatic tissue. In further embodiments, said terminal α-galactosyl is selected from the group consisting of Galα1-3Gal and Galα1-6Gal. In still further embodiments, said α-gal epitope is part of a molecule selected from the group consisting of a glycolipid, a glycoprotein, proteoglycan and a glycopolymer. In additional embodiments, said glycolipid comprises α-gal liposomes. In some embodiments, the preparation comprises α-gal epitope mimicking peptides linked to a macromolecule backbone or to another linker and they are capable of binding the anti-Gal antibody. In some embodiments, said applying is under conditions such that complement activation within or adjacent to said damaged tissue is enhanced. In further embodiments, said complement activation comprises production of C5a, C4a and C3a. In still further embodiments, said applying is under conditions such that neutrophil recruitment within or adjacent to said injured tissue is enhanced. In additional embodiments, said applying is under conditions such that monocyte and macrophage recruitment within or adjacent to said injured tissue is enhanced. In some embodiments, said applying is under conditions such that repair of said injured tissue is accelerated.

In some embodiments, the present invention contemplates a method, comprising: a) providing: i) a subject having endogenous anti-Gal antibody; ii) damaged nerve tissue; and iii) a preparation comprising an α-gal epitope having a terminal galactosyl; b) applying said preparation to said damaged nerve tissue to produce treated nerve tissue. In further embodiments, said terminal α-galactosyl is selected from the group consisting of Galα1-3Gal and Galα1-6Gal. In still further embodiments, said α-gal epitope is part of a molecule selected from the group consisting of a glycolipid, a glycoprotein, proteoglycan and a glycopolymer. In additional embodiments, said glycolipid comprises α-gal liposomes. In one embodiment, the preparation comprises α-gal epitope mimicking peptides linked to a macromolecule backbone or to another linker and they are capable of binding the anti-Gal antibody. In some embodiments, said applying is under conditions such that complement activation within or adjacent to said damaged tissue is enhanced. In further embodiments, said complement activation comprises production of C5a, C4a and C3a. In still further embodiments, said applying is under conditions such that neutrophil recruitment within or adjacent to said injured tissue is enhanced. In additional embodiments, said applying is under conditions such that monocyte and macrophage recruitment within or adjacent to said injured tissue is enhanced. In some embodiments, said applying is under conditions such that repair of said injured tissue is accelerated.

In some embodiments, the present invention contemplates a method, comprising: a) providing: i) a subject having endogenous anti-Gal antibody; ii) damaged liver tissue; and iii) a preparation comprising an α-gal epitope having a terminal galactosyl; b) applying said preparation to said damaged liver tissue to produce treated liver tissue. In further embodiments, said terminal α-galactosyl is selected from the group consisting of Galα1-3Gal and Galα1-6Gal. In still further embodiments, said α-gal epitope is part of a molecule selected from the group consisting of a glycolipid, a glycoprotein, a proteoglycan and a glycopolymer. In additional embodiments, said glycolipid comprises α-gal liposomes. In some embodiments, the preparation comprises α-gal epitope mimicking peptides linked to a macromolecule backbone or to another linker and they are capable of binding the anti-Gal antibody. In some embodiments, said applying is under conditions such that complement activation within or adjacent to said damaged tissue is enhanced. In further embodiments, said complement activation comprises production of C5a, C4a and C3a. In still further embodiments, said applying is under conditions such that neutrophil recruitment within or adjacent to said injured tissue is enhanced. In additional embodiments, said applying is under conditions such that monocyte and macrophage recruitment within or adjacent to said injured tissue is enhanced. In some embodiments, said applying is under conditions such that repair of said injured tissue is accelerated.

In some embodiments, the present invention contemplates a method, comprising: a) providing: i) a subject having endogenous anti-Gal antibody; ii) damaged endocrine gland tissue; and iii) a preparation comprising an α-gal epitope having a terminal galactosyl; b) applying said preparation to said damaged endocrine gland tissue to produce treated endocrine gland tissue. In further embodiments, said terminal α-galactosyl is selected from the group consisting of Galα1-3Gal and Galα1-6Gal. In still further embodiments, said α-gal epitope is part of a molecule selected from the group consisting of a glycolipid, a glycoprotein, proteoglycan and a glycopolymer. In additional embodiments, said glycolipid comprises α-gal liposomes. In some embodiments, the preparation comprises α-gal epitope mimicking peptides linked to a macromolecule backbone or to another linker and they are capable of binding the anti-Gal antibody. In some embodiments, said applying is under conditions such that complement activation within or adjacent to said damaged tissue is enhanced. In further embodiments, said complement activation comprises production of C5a, C4a and C3a. In still further embodiments, said applying is under conditions such that neutrophil recruitment within or adjacent to said injured tissue is enhanced. In additional embodiments, said applying is under conditions such that monocyte and macrophage recruitment within or adjacent to said injured tissue is enhanced. In some embodiments, said applying is under conditions such that repair of said injured tissue is accelerated.

In some embodiments, the present invention contemplates a method, comprising: a) providing: i) a subject having endogenous anti-Gal antibody; ii) damaged bone tissue; and iii) a preparation comprising an α-gal epitope having a terminal galactosyl; b) applying said preparation to said damaged bone tissue to produce treated bone tissue. In further embodiments, said terminal α-galactosyl is selected from the group consisting of Galα1-3Gal and Galα1-6Gal. In still further embodiments, said α-gal epitope is part of a molecule selected from the group consisting of a glycolipid, a glycoprotein, proteoglycan and a glycopolymer. In additional embodiments, said glycolipid comprises α-gal liposomes. In some embodiments, the preparation comprises α-gal epitope mimicking peptides linked to a macromolecule backbone or to another linker and they are capable of binding the anti-Gal antibody. In some embodiments, said applying is under conditions such that complement activation within or adjacent to said damaged tissue is enhanced. In further embodiments, said complement activation comprises production of C5a, C4a and C3a. In still further embodiments, said applying is under conditions such that neutrophil recruitment within or adjacent to said injured tissue is enhanced. In additional embodiments, said applying is under conditions such that monocyte and macrophage recruitment within or adjacent to said injured tissue is enhanced. In some embodiments, said applying is under conditions such that repair of said injured tissue is accelerated.

In some embodiments, the present invention contemplates a method, comprising: a) providing: i) a subject having endogenous anti-Gal antibody; ii) damaged cartilage tissue; and iii) a preparation comprising an α-gal epitope having a terminal galactosyl; b) applying said preparation to said damaged cartilage tissue to produce treated cartilage tissue. In further embodiments, said terminal α-galactosyl is selected from the group consisting of Galα1-3Gal and Galα1-6Gal. In still further embodiments, said α-gal epitope is part of a molecule selected from the group consisting of a glycolipid, a glycoprotein, proteoglycan and a glycopolymer. In additional embodiments, said glycolipid comprises α-gal liposomes. In some embodiments, the preparation comprises α-gal epitope mimicking peptides linked to a macromolecule backbone or to another linker and they are capable of binding the anti-Gal antibody. In some embodiments, said applying is under conditions such that complement activation within or adjacent to said damaged tissue is enhanced. In further embodiments, said complement activation comprises production of C5a, C4a and C3a. In still further embodiments, said applying is under conditions such that neutrophil recruitment within or adjacent to said injured tissue is enhanced. In additional embodiments, said applying is under conditions such that monocyte and macrophage recruitment within or adjacent to said injured tissue is enhanced. In some embodiments, said applying is under conditions such that repair of said injured tissue is accelerated.

In one embodiment, the present invention contemplates a method, comprising: a) providing; i) a subject having endogenous anti-Gal antibody and an injured tissue; and ii) a preparation comprising an α-gal epitope having a terminal α-galactosyl as part of a tissue repair and regeneration preparation; and b) applying said preparation to said injury to produce a treated injured tissue. In one embodiment, the tissue is an internal tissue. In one embodiment, the terminal α-galactosyl is selected from the group consisting of Galα1-3Gal, Galα1-2Gal, Galα1-6Gal or any α-galactose sugar units capable of binding anti-Gal antibodies. In one embodiment, the α-gal epitope is free or part of a molecule selected from the group consisting of a natural or synthetic glycolipid, glycoprotein, proteoglycan and a glycopolymer. In additional embodiments, said glycolipid comprises α-gal liposomes. In one embodiment, the preparation comprises α-gal epitope mimicking peptides linked to a macromolecule backbone or to another linker and they are capable of binding the anti-Gal antibody. In one embodiment, the preparation further comprises an injury care device selected from the group consisting of syringes, adhesive bands, compression bandages, sponges, gels, semi-permeable films, plasma clots, fibrin clots. In one embodiment, the device comprises physiological compositions including, but not limited to, solutions, suspensions, emulsions, creams, ointments, aerosol sprays, collagen containing substances, stabilizers, drops, matrix-forming substances, foams and/or dried preparation. In one embodiment, the applying is under conditions such that complement activation within or adjacent to said injured tissue is enhanced. In one embodiment, the complement activation comprises production of complement fragments C5a, C4a and C3a. In one embodiment, the applying is under conditions such that neutrophil recruitment within or adjacent to said injury is enhanced. In one embodiment, the applying is under conditions such that monocyte and macrophage recruitment within or adjacent to said injured tissue is enhanced. In one embodiment, the applying is under conditions such that stem cell recruitment within or adjacent to said injury is enhanced. In one embodiment, the applying is under conditions such that injury healing and tissue repair and regeneration is accelerated.

In one embodiment, the present invention contemplates a method, comprising: a) providing; i) a subject having endogenous anti-Gal antibody and an injured tissue; and ii) a preparation comprising an α-gal liposomes having glycolipids, glycoproteins with a terminal α-galactosyl and comprising α-gal liposomes as part of a tissue repair and regeneration preparation, and/or α-gal epitope mimicking peptides linked to a macromolecule backbone or to another linker and they are capable of binding the anti-Gal antibody and comprising α-gal liposomes; and b) applying said preparation to said injury to produce a treated injured tissue. In one embodiment, the preparation further comprises an injury care device selected from the group consisting of syringes, adhesive bands, compression bandages, sponges, gels, semi-permeable films, plasma clots, fibrin clots. In one embodiment, the device comprises physiological compositions including, but not limited to, solutions, suspensions, emulsions, creams, ointments, aerosol sprays, collagen containing substances, stabilizers, drops, matrix-forming substances, foams and/or dried preparation. In one embodiment, the preparation further comprises anti-Gal antibodies bound to said α-gal liposomes. In one embodiment, the applying is under conditions such that complement activation within or adjacent to said injured tissue is enhanced. In one embodiment, the complement activation comprises production of complement fragments C5a, C4a and C3a. In one embodiment, the applying is under conditions such that neutrophil recruitment within or adjacent to said injured tissue is enhanced. In one embodiment, the applying is under conditions such that monocyte and macrophage recruitment within or adjacent to said injured tissue is enhanced. In one embodiment, the applying is under conditions such that stem cell recruitment within or adjacent to said injury is enhanced. In one embodiment, the applying is under conditions such that injury healing and tissue repair and regeneration is accelerated.

In one embodiment, the present invention contemplates a method, comprising: a) providing; i) a subject having endogenous anti-Gal antibody and one or more of an injured tissue including, but not limited to, brain tissue, nerve tissue, eye tissue, gastrointestinal tissue, muscle tissue, cartilage tissue, bone tissue, endocrine glands and vascular tissue; ii) a preparation comprising an α-gal epitope having a terminal α-galactosyl as part of a tissue repair and regeneration preparation; and b) applying said preparation to said injured tissue to produce a treated injured tissue. In one embodiment, the terminal α-galactosyl is selected from the group consisting of Galα1-3Gal, Galα1-2Gal, Galα1-6Gal and any α-galactose sugar units capable of binding anti-Gal antibodies. In one embodiment, the α-gal epitope is free or part of a molecule selected from the group consisting of a natural or synthetic glycolipid, glycoprotein, and a glycopolymer. In one embodiment, the preparation comprises α-gal liposomes. In one embodiment, the preparation comprises α-gal epitope mimicking peptides linked to a macromolecule backbone or to another linker and they are capable of binding the anti-Gal antibody. In one embodiment, the preparation further comprises an injury care device selected from the group consisting of syringes, adhesive bands, compression bandages, sponges, gels, semi-permeable films, plasma clots, fibrin clots. In one embodiment, the device comprises physiological compositions including, but not limited to, solutions, suspensions, emulsions, creams, ointments, aerosol sprays, collagen containing substances, stabilizers, drops, matrix-forming substances, foams and/or dried preparation. In one embodiment, the preparation further comprises anti-Gal antibodies bound to said α-gal liposomes. In one embodiment, the applying is under conditions such that complement activation within or adjacent to said injured tissue is enhanced. In one embodiment, the complement activation comprises production of complement fragments C5a, C4a and C3a. In one embodiment, the applying is under conditions such that neutrophil recruitment within or adjacent to said injured tissue is enhanced. In one embodiment, the applying is under conditions such that monocyte and macrophage recruitment within or adjacent to said injured tissue is enhanced. In one embodiment, the applying is under conditions such that stem cell recruitment within or adjacent to said injury is enhanced. In one embodiment, the applying is under conditions such that injury healing and tissue repair and regeneration is accelerated.

In one embodiment, the present invention contemplates a method, comprising: a) providing; i) a subject having endogenous anti-Gal antibody and having diabetes in which insulin production is impaired; and ii) a preparation comprising an α-gal epitope having a terminal α-galactosyl as part of a tissue repair and regeneration preparation; and b) applying said preparation into the pancreas of said subject to induce regeneration of Langerhans Islets and production of endogenous insulin. In one embodiment, the terminal α-galactosyl is selected from the group consisting of Galα1-3Gal, Galα1-2Gal, Galα1-6Gal and any α-galactose sugar units capable of binding anti-Gal antibodies. In one embodiment, the α-gal epitope is free or part of a molecule selected from the group consisting of a natural or synthetic glycolipid, glycoprotein, and a glycopolymer. In one embodiment, the preparation comprises α-gal liposomes. In one embodiment, the preparation comprises α-gal epitope mimicking peptides linked to a macromolecule backbone or to another linker and they are capable of binding the anti-Gal antibody. In one embodiment, the preparation further comprises an injury care device selected from the group consisting of syringes, adhesive bands, compression bandages, sponges, gels, semi-permeable films, plasma clots, fibrin clots. In one embodiment, the device comprises physiological compositions including, but not limited to, solutions, suspensions, emulsions, creams, ointments, aerosol sprays, collagen containing substances, stabilizers, drops, matrix-forming substances, foams and/or dried preparation. In one embodiment, the preparation further comprises anti-Gal antibodies bound to said α-gal liposomes. In one embodiment, the applying is under conditions such that complement activation within or adjacent to said injured tissue is enhanced. In one embodiment, the complement activation comprises production of complement fragments C5a, C4a and C3a. In one embodiment, the applying is under conditions such that neutrophil recruitment within pancreas is enhanced. In one embodiment, the applying is under conditions such that monocyte and macrophage recruitment pancreas is enhanced. In one embodiment, the applying is under conditions such that stem cell recruitment within pancreas is enhanced. In one embodiment, the recruited stem cells differentiate into Langerhans Islet cells. In one embodiment, the Langerhans Islet cells produce insulin.

In one embodiment, the present invention contemplates a method, comprising a) providing; i) a subject having endogenous anti-Gal antibody and having injury in a peripheral nerve, spinal cord, blood vessel or any other tissue: ii) a device comprising a biodegradable or non-biodegradable sheet coated with or containing a preparation comprising an α-gal epitope having a terminal α-galactosyl as part of a tissue repair and regeneration preparation; and b) applying said sheet around said injured nerve, spinal cord, blood vessel, or other tissue to produce a treated injured tissue. In one embodiment, the terminal α-galactosyl is selected from the group consisting of Galα1-3Gal, Galα1-2Gal, Galα1-6Gal and any α-galactose sugar units capable of binding anti-Gal antibodies. In one embodiment, the α-gal epitope is free or part of a molecule selected from the group consisting of a natural or synthetic glycolipid, glycoprotein, and a glycopolymer. In one embodiment, the preparation comprises α-gal liposomes. In one embodiment, the preparation comprises α-gal epitope mimicking peptides linked to a macromolecule backbone or to another linker and they are capable of binding the anti-Gal antibody. In one embodiment, the preparation is part of a injury care device selected from the group consisting of collagen containing sheet, synthetic sheet, or any other sheet that can be wrapped around the injured nerve, spinal cord, blood vessel, or other injured tissue. In one embodiment, the preparation further comprises anti-Gal antibodies bound to said α-gal liposomes. In one embodiment, the applying is under conditions such that complement activation within or adjacent to said injured tissue is enhanced. In one embodiment, the complement activation comprises production of complement fragments C5a, C4a and C3a. In one embodiment, the applying is under conditions such that neutrophil recruitment to the injured tissue is enhanced. In one embodiment, the applying is under conditions such that monocyte and macrophage recruitment to the injured tissue is enhanced. In one embodiment, the applying is under conditions such that stem cell recruitment to the injured tissue is enhanced. In one embodiment, the recruited stem cells differentiate into cells that repair the injured tissue.

In some embodiments, the invention relates to a method, comprising: a) providing: i) a subject having endogenous anti-Gal antibody; ii) a wound; and iii) a preparation comprising an α-gal epitope having a terminal galactosyl; and b) applying said preparation to said wound to produce a treated wound. In further embodiments, said terminal α-galactosyl is selected from the group consisting of Galα1-3Gal, and Galα1-6Gal. In still further embodiments, said α-gal epitope is part of a molecule selected from the group consisting of a glycolipid, a glycoprotein, and a glycopolymer. In additional embodiments, said glycolipid comprises α-gal liposomes. In one embodiment, the preparation comprises α-gal epitope mimicking peptides linked to a macromolecule backbone or to another linker and they are capable of binding the anti-Gal antibody. In some embodiments, said applying is under conditions such that complement activation within or adjacent to said wound is enhanced. In further embodiments, said complement activation comprises production of C5a, C4a and C3a. In still further embodiments, said applying is under conditions such that neutrophil recruitment within or adjacent to said wound is enhanced. In additional embodiments, said applying is under conditions such that monocyte and macrophage recruitment within or adjacent to said wound is enhanced. In some embodiments, said applying is under conditions such that wound closure is accelerated. In further embodiments, the method is used to treat subjects diagnosed with or exhibiting symptoms associated with heart disease and damage, arthritis, osetoarthritis, cartilage repair and diabetes mellitus. In still further embodiments, the disclosed method is used to treat tissue or organ damage in combination with the application of stem cells.

In some embodiments the invention relates to a method, comprising: a) providing; i) a subject having a wound; ii) a wound care device comprising a preparation comprising an α-gal epitope having a terminal α-galactosyl, and iii) an anti-Gal antibody; and b) applying said wound care device to said wound to produce a treated wound. In further embodiments, said terminal α-galactosyl is selected from the group consisting of Galα1-3Gal, Galα1-2Gal and Galα1-6Gal. In still further embodiments, said α-gal epitope is part of a molecule selected from the group consisting of a glycolipid, a glycoprotein, and a glycopolymer. In additional embodiments, said glycolipid comprises α-gal liposomes. In one embodiment, the preparation comprises α-gal epitope mimicking peptides linked to a macromolecule backbone or to another linker and they are capable of binding the anti-Gal antibody. In some embodiments, said preparation is part of a wound care device selected from the group consisting of adhesive bands, compression bandages, gels, semi-permeable films, and foams. In further embodiments, the disclosed method and preparation is used to treat subjects diagnosed with or exhibiting symptoms associated with heart disease and damage, arthritis, osetoarthritis, cartilage repair and diabetes mellitus. In still further embodiments, the disclosed method and preparation is used to treat tissue or organ damage in combination with the application of stem cells.

In some embodiments, the invention relates to a burn care device comprising a preparation comprising an α-gal epitope having a terminal α-galactosyl. In further embodiments, said terminal α-galactosyl is selected from the group consisting of Galα1-3Gal, and Galα1-6Gal. In still further embodiments, said α-gal epitope is part of a molecule selected from the group consisting of a glycolipid, a glycoprotein, and a glycopolymer. In additional embodiments, said glycolipid comprises α-gal liposomes. In one embodiment, the preparation comprises α-gal epitope mimicking peptides linked to a macromolecule backbone or to another linker and they are capable of binding the anti-Gal antibody. In some embodiments, said preparation further comprises anti-Gal antibodies bound to said α-gal liposomes. In further embodiments, said device is in the form of one of the group consisting of adhesive bands, compression bandages, gels, semipermeable films, and foams. In further embodiments, the disclosed device and preparation is used to treat subjects diagnosed with or exhibiting symptoms associated with heart disease and damage, arthritis, osetoarthritis, cartilage repair and diabetes mellitus. In still further embodiments, the disclosed device and preparation is used to treat tissue or organ damage in combination with the application of stem cells.

In some embodiments, the invention relates to a method, comprising: a) providing: i) a subject having endogenous anti-Gal antibody; and ii) damaged cardiac tissue; and iii) a preparation comprising an α-gal epitope having a terminal galactosyl; b) applying said preparation to said damaged cardiac tissue to produce treated cardiac tissue. In further embodiments, said terminal α-galactosyl is selected from the group consisting of Galα1-3Gal, Galα1-2Gal and Galα1-6Gal. In still further embodiments, said α-gal epitope is part of a molecule selected from the group consisting of a glycolipid, a glycoprotein, and a glycopolymer. In additional embodiments, said glycolipid comprises α-gal liposomes. In some embodiments, the preparation comprises α-gal epitope mimicking peptides linked to a macromolecule backbone or to another linker and they are capable of binding the anti-Gal antibody. In some embodiments, said applying is under conditions such that complement activation within or adjacent to said damaged cardiac tissue is enhanced. In further embodiments, said complement activation comprises production of C5a, C4a and C3a. In still further embodiments, said applying is under conditions such that neutrophil recruitment within or adjacent to said damaged cardiac tissue is enhanced. In additional embodiments, said applying is under conditions such that monocyte and macrophage recruitment within or adjacent to said damaged cardiac tissue is enhanced. In some embodiments, said applying is under conditions such that repair of said damaged cardiac tissue is accelerated.

In some embodiments, the invention relates to a method, comprising: providing a subject having endogenous anti-Gal antibody and tissue damaged by diabetes; and a preparation comprising an α-gal epitope having a terminal galactosyl; and applying said preparation to said tissue damaged by diabetes to produce treated tissue. In further embodiments, said terminal α-galactosyl is selected from the group consisting of Galα1-3Gal, Galα1-2Gal, and Galα1-6Gal. In still further embodiments, said α-gal epitope is part of a molecule selected from the group consisting of a glycolipid, a glycoprotein, and a glycopolymer. In additional embodiments, said glycolipid comprises α-gal liposomes. In some embodiments, the preparation comprises α-gal epitope mimicking peptides linked to a macromolecule backbone or to another linker and they are capable of binding the anti-Gal antibody. In some embodiments, said applying is under conditions such that complement activation within or adjacent to said tissue damaged by diabetes is enhanced. In further embodiments, said complement activation comprises production of C5a and C3a. In still further embodiments, said applying is under conditions such that neutrophil recruitment within or adjacent to said tissue damaged by diabetes is enhanced. In additional embodiments, said applying is under conditions such that monocyte and macrophage recruitment within or adjacent to said tissue damaged by diabetes is enhanced. In some embodiments, said applying is under conditions such that repair of said tissue damaged by diabetes is accelerated.

In some embodiments, the invention relates to a method, comprising: providing a subject having endogenous anti-Gal antibody and tissue damaged by osteoarthritis; and a preparation comprising an α-gal epitope having a terminal galactosyl; and applying said preparation to said tissue damaged by osteoarthritis to produce treated tissue. In further embodiments, said terminal α-galactosyl is selected from the group consisting of Galα1-3Gal, Galα1-2Gal and Galα1-6Gal. In still further embodiments, said α-gal epitope is part of a molecule selected from the group consisting of a glycolipid, a glycoprotein, and a glycopolymer. In additional embodiments, said glycolipid comprises α-gal liposomes. In some embodiments, the preparation comprises α-gal epitope mimicking peptides linked to a macromolecule backbone or to another linker and they are capable of binding the anti-Gal antibody. In some embodiments, said applying is under conditions such that complement activation within or adjacent to said tissue damaged by osteoarthritis is enhanced. In further embodiments, said complement activation comprises production of C5a, C4a and C3a. In still further embodiments, said applying is under conditions such that neutrophil recruitment within or adjacent to said tissue damaged by osteoarthritis is enhanced. In additional embodiments, said applying is under conditions such that monocyte and macrophage recruitment within or adjacent to said tissue damaged by osteoarthritis is enhanced. In some embodiments, said applying is under conditions such that repair of said tissue damaged by osteoarthritis is accelerated. In further embodiments, said tissue damaged by osteoarthritis is selected from the group consisting of bone and cartilage.

In one embodiment, the present invention contemplates a method, comprising: a) providing; i) a subject having endogenous anti-Gal antibody, wherein the subject has an injured tissue and wherein the injured tissue is capable of forming a scar; and ii) a preparation comprising an α-gal epitope having a terminal α-galactosyl; and b) applying said preparation to said tissue under conditions such that the scar formation is prevented. In one embodiment, the tissue is an internal tissue. In one embodiment, the terminal α-galactosyl is selected from the group consisting of Galα1-3Gal, Galα1-2Gal, Galα1-6Gal, α-galactose sugar units capable of binding anti-Gal antibodies and α-gal epitope mimicking peptides linked to a macromolecule backbone or to another linker and they are capable of binding the anti-Gal antibody. In one embodiment, the α-gal epitope is soluble. In one embodiment, the α-gal epitope is attached to a molecule selected from the group consisting of a natural or synthetic glycolipid, glycoprotein, proteoglycan and a glycopolymer. In one embodiment, the preparation comprises α-gal liposomes. In one embodiment, the α-gal liposomes further comprise anti-Gal antibodies. In one embodiment, the preparation further comprises an injury care device selected from, but not limited to, the group consisting of syringes, adhesive bands, compression bandages, wound dressings, sponges, gels, ointments, creams, suspensions, solutions, semi-permeable films, plasma clots, fibrin clots. In one embodiment, the device comprises physiological compositions including, but not limited to, solutions, suspensions, emulsions, creams, ointments, aerosol sprays, collagen containing substances, stabilizers, drops, matrix-forming substances, foams and/or dried preparation. In one embodiment, the preparation further comprises anti-Gal antibodies bound to said α-gal liposomes. In one embodiment, the injured tissue is selected from the group consisting of skin tissue brain tissue, nerve tissue, eye tissue, gastrointestinal tissue, muscle tissue, heart tissue, cartilage tissue, bone tissue, connective tissue, endocrine glands and/or vascular tissue. In one embodiment, the preparation comprises α-gal liposomes.

In one embodiment, the present invention contemplates a method, comprising: a) providing; i) a subject comprising an ischemic heart muscle caused by a myocardial infarction, wherein the subject further comprises endogenous anti-Gal antibody; ii) a preparation comprising an α-gal epitope having a terminal α-galactosyl; and b) applying said preparation to said ischemic heart muscle, thereby creating regenerated heart muscle cells in the ischemic tissue. In one embodiment, the ischemic heart muscle comprises injured heart muscle. In one embodiment, the terminal α-galactosyl is selected from the group consisting of Galα1-3Gal, Galα1-2Gal, Galα1-6Gal, and α-galactose sugar units capable of binding anti-Gal antibodies. In one embodiment, the α-gal epitope is soluble. In one embodiment, the α-gal epitope is bound to a molecule selected from the group consisting of a natural or synthetic glycolipid, glycoprotein, and a glycopolymer. In one embodiment, the preparation further comprises of anti-Gal antibodies bound to said α-gal liposomes. In one embodiment, the preparation is administered into said injured heart muscle by injection. In one embodiment, the regenerated heart muscle cells partially or fully restore the contractile activity of the injured heart muscle.

BRIEF DESCRIPTION OF THE DRAWINGS

The following are illustrations of the present invention and are not intended to limit the scope of the invention in any manner.

FIG. 2 shows the components of α-gal liposomes prepared from rabbit red blood cell (RBC) membranes.

FIG. 3 shows the binding of anti-Gal to α-gal liposomes either in an in vitro suspension or in a solid-phase antigen in an enzyme-linked immunosorbent assay (ELISA).

FIG. 4 shows the activation of human complement or rabbit complement by human anti-Gal binding to α-gal epitopes on α-gal liposomes.

FIG. 6A shows untreated skin with the epidermis containing one or two layers of epithelial cells, and the dermis containing fibroblasts and fat cells (×100). FIG. 6B shows skin 12 hours post-injection (×100). FIG. 6C shows skin 12 h post-injection with the injection site at the center of the figure (×100). FIG. 6D shows skin 12 h post-injection (×400). Higher magnification of the infiltrating inflammatory cells indicates that the cells are neutrophils, based on the morphological characteristics of their nuclei. FIG. 6E shows skin 48 h post-injection (×400). The infiltrating inflammatory cells at this time point are mononuclear cells with characteristics of macrophages, as indicated by the kidney shape of many of these cells. FIG. 6F shows skin five days post-injection (×100). Most macrophages assume a round morphology because of internalization of numerous α-gal liposomes. The area in the center of the injection site is devoid of cells and is functioning as an α-gal liposome depot. FIG. 6G shows skin 14 days post-injection (×100) with macrophages still visible in area of the injection site. FIG. 6H shows skin 20 days post-injection (×100). The injection area contains many myofibroblasts differentiating into fibroblasts or muscle cells, and almost no macrophages are observed within the injected area.

FIG. 12A. Heart injected with saline obtained 2 week post implantation. Note the necrotic cardiomyocytes and the infiltrating neutrophils (×100).

FIG. 12B. Heart injected with α-gal liposomes obtained 2 week post implantation. Note the large number of infiltrating macrophages (×100).

FIG. 12C. As FIG. 12B, however the implanted heart was removed after 4 weeks. Note the border between the site of the α-gal liposomes injection (lower half) and the non-injected area which contains migrating macrophages (×200).

FIG. 12D. An area of the myocardium in α-gal liposomes injected hearts which lacks infiltrating cells, 2 weeks post implantation. Note that no nuclei are detected in the dead cardiomyocytes (×100).

FIG. 13A: Muscle fibers in an uninjured skeletal muscle comprising muscle cell syncitia (myotubes), formed by fusion of myoblasts, with nuclei in the periphery of the tubes.

FIG. 13B: Ischemia-induced myotube death after 96 hours, showing the resulting necrosis after sham injection with saline to serve as control to α-gal liposomes injection. Neutrophil infiltration of the necrotic tissue may be observed. Decreased myotube syncitia size is also observed wherein the nuclei of each myotube accumulate in a row. Subsequently, the dead myotubes are phagocytosed by debriding macrophages.

FIG. 13C: Ischemia-induced myotube death after 96 hours, showing improved structure after injection with 10 mg α-gal liposomes (H&E×200).

FIG. 14A. Cells obtained from the subcutaneously implanted PVA sponge, 6 days post implantation. Most cells have the morphology of activated macrophages. The multiple vacuoles represent α-gal liposomes internalized by the macrophages. The bar represents 10 μM (×500).

FIGS. 14B and 14C: Infiltrating macrophage populations also include cells that display an extensive ability to proliferate, i.e., to self renew, resulting in 200-500 cells per colony formed from one cell within a period of 5 days. Note the multiple mitotic cells in FIG. 14B. The frequency of these colony forming cells among cultured macrophages from PVA sponges is 3-5 cells/$10^5$ macrophages. The colonies are representative of similar colonies from infiltrating macrophages in 5 mice.

FIG. 15A: KO mouse peritoneal macrophages were incubated for 1 h at 4° C. with α-gal liposomes (1.0 mg/ml). The proportion of double stained cells representing α-gal liposomes bound to macrophages as measured by flow cytometry is indicated in the upper right corner. Data are representative for 3 independent studies.

FIG. 15B: KO mouse peritoneal macrophages were incubated for 1 h at 4° C. with anti-Gal antibody coated α-gal liposomes. The proportion of double stained cells representing α-gal liposomes bound to macrophages is indicated in the upper right corner. Data are representative for 3 independent studies.

FIG. 15C: Secretion of vascular endothelial growth factor (VEGF) by peritoneal macrophages co-cultured with anti-Gal antibody coated α-gal liposomes (closed columns); non-antibody coated α-gal liposomes (gray columns); or no liposomes (open columns). VEGF was quantified in culture media after 24 h or 48 h (Mean+SD [standard deviation] from the 4 mice/group). VEGF secretion by macrophages incubated with anti-Gal antibody coated α-gal liposomes is significantly higher than in the other two groups at each time point ($p<0.05$).

FIG. 17A: 12 h post injection. Empty areas represent injected liposomes that were dissolved during the staining process (×100). Scale bar=100 mm.

FIG. 17B: 24 h post injection (×100).

FIG. 17C: 24 h post injection of α-gal liposomes and 20 μg cobra venom factor (CVF) (×100).

FIG. 17D: The inset in FIG. 17A, showing recruited neutrophils (×200).

FIG. 17E: The inset in FIG. 17B indicating that most (>85%) of the cells have morphology of macrophages (×200).

FIG. 17F: 24 h post injection of 10 mg KO pig liposomes (i.e. liposomes that lack α-gal glycolipids).

FIG. 17G: 6 days post injection of α-gal liposomes (×100).

FIG. 17H: 14 days post injection of α-gal liposomes (×100).

FIG. 17I: 28 days post injection of α-gal liposomes (×100).

FIG. 17J: The inset in FIG. 17G, indicating that the mass of cells by the injection site is comprised of large macrophages containing multiple vacuoles that represent internalized phagocytozed α-gal liposomes (×200). Scale bar=50 μm FIG. 17K: 96 h post injection. The section is immunostained with HRP-anti-4/F80 which stains macrophages in brown (×400), and counterstained with H&E.

FIG. 17L: Morphology of individual recruited macrophages, 6 days post injection. The multiple vacuoles represent the anti-Gal antibody coated α-gal liposomes internalized by the macrophages (×1000). Scale bar=10 μm.

FIG. 23A: Control wound treated with saline dressing for 3 days. *Panniculus carnosus* is exposed where epidermis and dermis were removed. No significant cell infiltration is observed. (×100)

FIG. 23B: Wound treated for 3 days with α-gal liposomes. Note the multilayered proliferating epidermis at the periphery of the wound and infiltration of macrophages in the regenerating dermis. The platelet plug is present above the healing wound. Arrow marks the wound edge. ×200

FIG. 23C: Day 6 saline treated wound (center of the wound). Regenerating thin dermis over *Panniculus carnosus* is filled with macrophages. No regenerating epidermis is observed. ×200

FIG. 23D: Day 6 wound treated with α-gal liposomes (center of the wound). Note that multi-layered regenerating epidermis covers the entire area of the wound and many macrophages infiltrate the dermis. ×200

FIG. 23E: Day 6 saline treated wound (periphery of the wound). The regenerating epidermis in the lower left area does not cover the entire wound. The dermis is filled with macrophages. ×200

FIG. 23F: Day 6 wound treated with α-gal liposomes (periphery of the wound). The uninjured skin is observed in the right area. The dermis of the wound is filled with macrophages. Arrow marks the wound bed. Pink stratum corneum is observed over the regenerating epidermis. ×200; Scale bar=50 µm.

FIG. 28A: Naive KO mice receiving two i.p. injections of 10 mg α-gal liposomes at 1 week intervals. (Δ)-sera from mice injected with α-gal liposomes; (•)-sera from mice injected with PKM; (○)-sera from mice injected with PKM, were preincubated for 30 min with 1 mg/ml α-gal BSA.

FIG. 28B: Naïve KO mice receiving topical application of α-gal liposomes onto burns for a period of 2 weeks. (Δ)-sera from mice with burns treated topically with α-gal liposomes. Curves of (Δ) and (○) represent no IgG binding. Data from three mice in each group.

DEFINITIONS

Figure 1A:
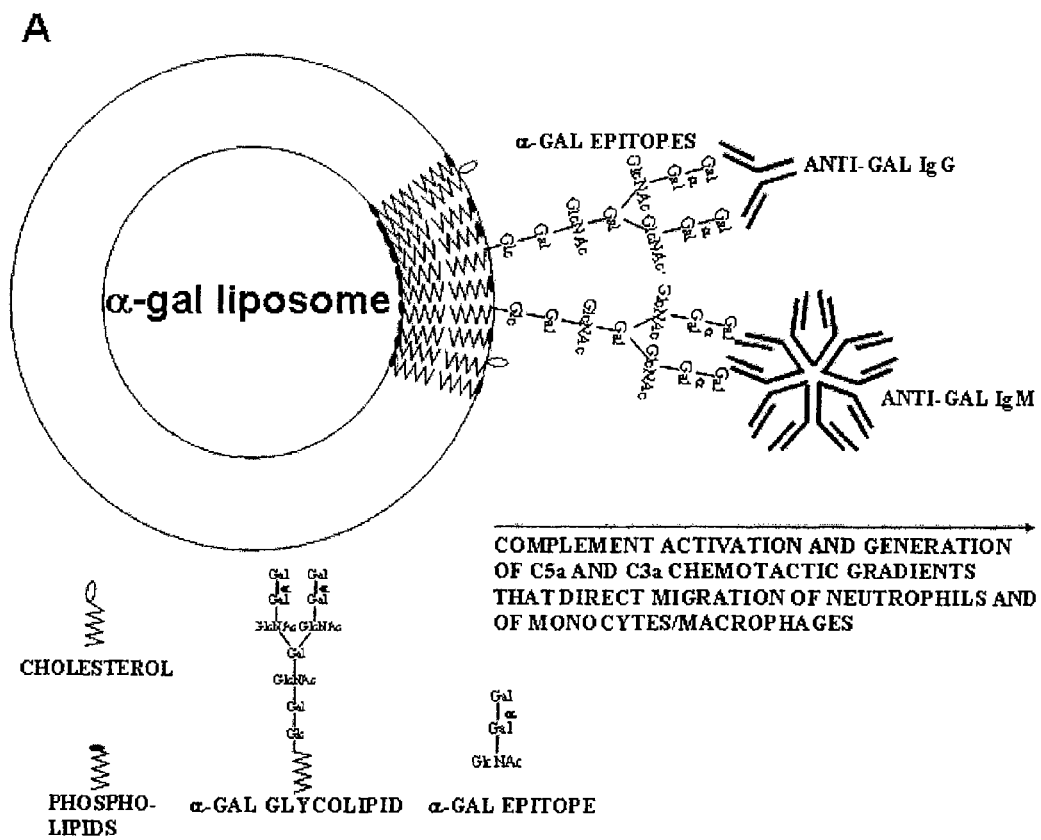
FIG. 1A shows an interaction of an α-gal liposome with anti-Gal IgG and IgM antibodies.

To facilitate an understanding of the present invention, a number of terms and phrases are defined below:

The term "α-gal epitope" as used herein, refers to any molecule, or part of a molecule, with a terminal structure comprising Galα1-3Galβ1-4GlcNAc-R, Galα1-3Galβ1-3GlcNAc-R, or any carbohydrate chain with terminal Galα1-3Gal at the non-reducing end, or any molecule with terminal α-galactosyl unit capable of binding the anti-Gal antibody.

The term "glycolipid" as used herein, refers to any molecule with at least one carbohydrate chain linked to a ceramide, or a fatty acid chain, or any other lipid. Alternatively, a glycolipid maybe referred to as a glycosphingolipid.

The term "α-gal glycolipid" as used herein, refers to any glycolipid that has at least one α-gal epitope on its nonreducing end of the carbohydrate chain.

The term "α-gal epitope mimicking peptides" as used herein, refers to any peptide that is capable of binding the anti-Gal antibody.

The term "α-gal liposomes" as used herein, refers to any liposomes that have α-gal epitopes and are capable of binding the anti-Gal antibody. α-gal liposomes may be of any size including, but not limited to, the range of approximately 50 nanometer (nm) to 100 micrometer (µm)

The term "α-gal ointment" as used herein, refers to any ointment of hydrocarbon base or any other base that contains α-gal epitopes in a free form or α-gal epitopes in α-gal glycolipids, α-gal proteins, or α-gal polymers.

As used herein, the term "purified" refers to molecules (polynucleotides, or polypeptides, or glycolipids) that are removed from their natural environment, isolated or separated. "Substantially purified" molecules are at least 50% free, preferably at least 75% free, more preferably at least 90% and most preferably at least 95% free from other components with which they are naturally associated.

The terms "α1,3-galactosyltransferase," "α-1,3-galactosyltransferase," "α1,3GT," "glycoprotein α-galactosyltransferase 1" and "GGTA1," as used herein refer to any enzyme capable of synthesizing α-gal epitopes. The enzyme is expressed in most mammals with the exception of humans, apes and Old World monkeys. The carbohydrate structure produced by the enzyme is immunogenic in man and most healthy people have high titer natural anti α-gal antibodies, also referred to as "anti-Gal" antibodies. In some embodiments, the term "α1,3GT" refers to a common marmoset gene (e.g., *Callithrix jacchus*—GENBANK Accession No. 571333) and its gene product, as well as its functional mammalian counterparts (e.g., other New World monkeys, prosimians and non-primate mammals, but not Old World monkeys, apes and humans). The term "α1,3GT" is in no way limited to a particular mammal, for example, the term may include mouse α1,3GT (e.g., *Mus musculus*—nucleotides 445 to 1560 of GENBANK Accession No. NM_010283), bovine α1,3GT (e.g., *Bos taurus*—GENBANK Accession No. NM_177511), feline α1,3GT (e.g., *Felis catus*—GENBANK Accession No. NM_001009308), ovine α1,3GT (e.g., *Ovis aries*—GENBANK Accession No. NM_001009764), rat α1,3GT (e.g., *Rattus norvegicus*—GENBANK Accession No. NM_145674) and porcine α1,3GT (e.g., *Sus scrofa*—GENBANK Accession No. NM_213810). Some embodiments of the present invention comprise a functional variant of a mammalian α1,3GT, which differs from the wild type mammalian α1,3GT sequences in, for example, fewer than 1-5% of the residues. α1,3GT variants include but are in no way limited to naturally occurring, functional mammalian α1,3GT variants, as well as non-naturally occurring variants generated by recombinant or other means (e.g., 1, 2, 3, 4 or 5 amino acid substitutions, deletions, or additions, preferably corresponding to a residue from a functional mammalian α1,3GT homolog) are contemplated to find use in the compositions and methods of the present invention. In other embodiments, truncated forms of a mammalian α1,3GT, which retain catalytic activity, are employed (e.g., GGTA1 lacking 90 amino acid N-terminal stem region).

The term "KO mouse" as used herein refers to any mouse in which the α1,3GT gene was knocked out, i.e. disrupted, to prevent synthesis of self α-gal epitopes, thereby enabling production of anti-Gal antibodies by the mouse.

The term "KO pig" as used herein refers to any pig in which the α1,3GT gene was knocked out, i.e. disrupted, to prevent synthesis of self α-gal epitopes.

The term "anti-Gal binding epitope", as used herein, refers to any molecule or part of molecule that is capable of binding in vivo the natural anti-Gal antibody.

The term "isolated" as used herein, refers to any composition or mixture that has undergone a laboratory purification procedure including, but not limited to, extraction, centrifugation and chromatographic separation (e.g., thin layer chromatography or high performance liquid chromatography). Usually such a purification procedures provides an isolated composition or mixture based upon physical, chemical, or electrical potential properties. Depending upon the choice of procedure an isolated composition or mixture may contain other compositions, compounds or mixtures having similar chemical properties.

The term "control" refers to subjects or samples which provide a basis for comparison for experimental subjects or samples. For instance, the use of control subjects or samples permits determinations to be made regarding the efficacy of experimental procedures. In some embodiments, the term "control subject" refers to animals, which receive a mock treatment (e.g., saline).

The term "diabetic" as used here refers to organisms which have a disorder characterized by the insufficient production or utilization of insulin. Insulin is a pancreatic hormone that is needed to convert glucose for cellular metabolism and energy production. In preferred embodiments of the present invention, the term "diabetic patient" refers to patients suffering from diabetes mellitus. The term "diabetic" encompasses both patients with type I diabetes (juvenile onset) and patients with type II diabetes (adult onset). "Type I diabetes" also referred to as "insulin-dependent diabetes" is a form of diabetes mellitus that usually develops during childhood or adolescence and is characterized by a severe deficiency in insulin secretion resulting from atrophy of the islets of Langerhans and causing hyperglycemia and a marked tendency towards ketoacidosis. "Type II diabetes" also referred to as "non-insulin-dependent diabetes" is a form of diabetes mellitus that develops especially in adults (most often in obese individuals) and that is characterized by hyperglycemia resulting from both insulin-resistance and an inability to produce more insulin.

The term "aged" as used herein refer to older human subjects (e.g., middle age and above of 50 years and older, senior citizen and above of 65 years and older, or elderly and above of 80 years and older, etc.). The term "aged" also encompass older nonhuman mammalian subjects at similar stages in their life cycles (e.g., 8-12 years and older for cats and large dogs, 10-15 years and older for small and medium sized dogs, 15-18 months and older for mice, etc.)

The terms "patient" and "subject" refer to a mammal or an animal that is a candidate for receiving medical treatment.

As used herein, the term "wound" refers to a disruption of the normal continuity of structures caused by a physical (e.g., mechanical) force, a biological (e.g., thermic or actinic force, or a chemical means. In particular, the term "wound" encompasses wounds of the skin. The term "wound" also encompasses contused wounds, as well as incised, stab, lacerated, open, penetrating, puncture, abrasions, grazes, burns, frostbites, corrosions, wounds caused by ripping, scratching, pressure, and biting, and other types of wounds. In particular, the term encompasses ulcerations (i.e., ulcers), preferably ulcers of the skin.

As used herein, the term "wound healing" refers to a regenerative process with the induction of an exact temporal and spatial healing program comprising wound closure and the processes involved in wound closure. The term "wound healing" encompasses but is not limited to the processes of granulation, neovascularization, fibroblast, endothelial and epithelial cell migration, extracellular matrix deposition, re-epithelialization, and remodeling.

The term "wound closure" refers to the healing of a wound wherein sides of the wound are rejoined to form a continuous barrier (e.g., intact skin).

The term "granulation" refers to the process whereby small, red, grain-like prominences form on a raw surface (that of wounds or ulcers) as healing agents.

The term "neovascularization" refers to the new growth of blood vessels with the result that the oxygen and nutrient supply is improved. Similarly, the term "angiogenesis" refers to the vascularization process involving the development of new capillary blood vessels.

The term "cell migration" refers to the movement of cells (e.g., fibroblast, endothelial, epithelial, etc.) to the wound site.

The term "extracellular matrix deposition" refers to the secretion by cells of fibrous elements (e.g., collagen, elastin, reticulin), link proteins (e.g., fibronectin, laminin), and space filling molecules (e.g., glycosaminoglycans). As used herein, the term "type I collagen" refers to the most abundant collagen, which forms large well-organized fibrils having high tensile strength.

The term "re-epithelialization" refers to the reformation of epithelium over a denuded surface (e.g., wound).

The term "remodeling" refers to the replacement of and/or devascularization of granulation tissue.

The term "impaired healing capabilities" comprises wounds, which are characterized by a disturbed wound healing process. Examples of wounds with impaired healing capabilities are wounds of diabetic patients and alcoholics, wounds which are infected by microorganisms, ischemic wounds, wounds of patients suffering from deficient blood supply or venous stasis, and ulcers. Particularly preferred wounds are diabetic wounds. Other preferred wounds include wounds of elderly subjects and chronic wounds of subjects of any age.

As used herein, the term "chronic wound" refers to a wound that does not fully heal even after a prolonged period of time (e.g., 2 to 3 months or longer).

The term "diabetic wounds" refers to wounds of mammals and humans suffering from diabetes. An example of a diabetic wound is an ulcer (e.g., *Ulcus cruris arteriosum* or *Necrobiosis lipoidica*).

As used herein, the term "ulcer" (i.e., "ulceration") refers to a local defect or excavation of the surface of an organ or tissue, produced by sloughing of necrotic tissue. The term encompasses various forms of ulcers (e.g., diabetic, neuropathic, arterial, decubitus, dental, perforating, phagedenic, rodent, trophic, tropical, varicose, venereal, etc.), although in preferred embodiments, surface (i.e., skin) ulcers are involved in the present invention. Especially preferred ulcers are diabetic ulcers.

In some embodiments, the present invention provides methods and compositions for "accelerating wound healing," whereby different aspects of the wound healing process are "enhanced." As used herein, the term "enhanced" indicates that the methods and compositions provide an increased rate of wound healing. In preferred embodiments, the term "enhanced" indicates that the wound healing rate and/or a wound healing process occurs at least 10% faster than is observed in untreated or control-treated wounds. In particularly preferred embodiments, the term "enhanced" indicates that the wound healing rate and/or a wound healing process occurs at least 15% faster than is observed in untreated or control-treated wounds. In still further preferred embodiments, the term "enhanced" indicates that the wound healing rate and/or a wound healing process occurs at least 20% (e.g., 50%, 100%, . . . ) faster than wounds untreated or control-treated wounds.

As used herein, the terms "localized" and "local" refer to the involvement of a limited area. Thus, in contrast to "systemic" treatment, in which the entire body is involved, usually through the vascular and/or lymph systems, localized treatment involves the treatment of a specific, limited area. Thus, in some embodiments, discrete wounds are treated locally using the methods and compositions of the present invention.

The term, "VEGF" as used herein, is an art accepted abbreviation for vascular endothelial growth factor.

As used herein, the term "topically" means application to the surface of the skin, mucosa, viscera, etc. Similarly, the terms "topically active drug" and "topically active agent" refer to a substance or composition, which elicits a pharmacologic response at the site of application (e.g., skin), but is not necessarily an antimicrobial agent.

As used herein, the term "medical devices" includes any material or device that is used on, in, or through a patient's body in the course of medical treatment for a disease or injury. Medical devices include, but are not limited to, such items as medical implants, wound care devices, drug delivery devices, and body cavity and personal protection devices. The medical implants include, but are not limited to, urinary catheters, intravascular catheters, dialysis shunts, wound drain tubes, skin sutures, vascular grafts, implantable meshes, intraocular devices, heart valves, and the like.

As used herein, "wound care devices" and "burn care devices" include, but are not limited to conventional materials such as dressings, plasters, compresses, ointments containing the pharmaceuticals, or gels containing the pharmaceuticals that can be used in accordance with the present invention. Thus, it is possible to administer the wound care devices comprising α-gal epitopes or α-gal epitopes and anti-Gal antibodies topically and locally in order to exert an immediate and direct effect on wound healing. The topical administration of wound care devices can be effected, for example, in the form of a solution, an emulsion, a cream, an ointment, a foam, an aerosol spray, a gel matrix, a sponge, drops or washings. Suitable additives or auxiliary substances are isotonic solutions, such as physiological sodium chloride solutions or sodium alginate, demineralized water, stabilizers, collagen containing substances such as Zyderm II or matrix-forming substances such as povidone. To generate a gel basis, formulations, such as aluminum hydroxide, polyacrylacid derivatives, and cellulose derivatives (e.g., carboxymethyl cellulose), fibrin clot, and plasma clots are suitable. These gels can be prepared as hydrogels on a water basis or as oleogels with low and high molecular weight paraffines or Vaseline and/or yellow or white wax. As emulsifier alkali soaps, metal soaps, amine soaps or partial fatty acid esters of sorbitants can be used, whereas lipids can be added as Vaseline, natural and synthetic waxes, fatty acids, mono-, di-, triglycerides, paraffin, natural oils or synthetic fats. The wound care devices comprising α-gal epitopes and anti-Gal antibodies according to the invention can also, where appropriate, be administered topically and locally, in the region of the wound, in the form of liposome/antibody complexes, or complexes between any antigen and its corresponding antibody, or complement activating substances.

Furthermore, the treatment can be effected using a transdermal therapeutic system (TTS), which enables the pharmaceuticals of the present invention to be released in a temporally controlled manner. To improve the penetration of the administered drug through the membrane, additives such as ethanol, urea or propylene glycol can be added in addition to polymeric auxiliaries.

The term "fibrin clot" refers to any mass, mesh, plug comprising isolated fibrinogen mixed with thrombin and thus induced to convert into fibrin that is non globular and forms a clot.

The term "plasma clot" refers to plasma mixed with an agent inducing conversion of fibrinogen within the plasma into non globular fibrin, thereby forming a clot.

The term "soluble" refers to any ability of a compound to completely dissolve within a solution. Usually, but not exclusively, the compound may be a salt that dissociates into a cationic and anionic species. Nonetheless, it would be expected that a fully soluble compound comprises a monomeric species.

The term "physiological composition" or "pharmaceutical composition" as used herein, are clinically acceptable (i.e., for example, antiseptic, sterile, non-inflammatory, non-allergenic) such they can be administered internally and/or externally and may comprise any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such compositions.

DETAILED DESCRIPTION OF THE INVENTION

The present invention is related to the field of wound healing. In particular, the present invention provides compositions and methods comprising molecules with linked α-gal epitopes for induction of an inflammatory response localized within or surrounding damaged tissue. In some embodiments, the present invention provides treatments for tissue repair in normal subjects and in subjects having impaired healing capabilities, such as diabetic and aged subjects.

In some embodiments, the invention relates to methods and compositions for the promotion of wound healing. Macrophages play a major role in the success of wound healing in part by generation of reactive radicals such as nitric oxide and oxygen peroxide, and through the secretion of collagenase and elastase as provided for in Bryant et al., *Prog. Clin. Biol. Res.* 266, 273 (1988) and Knighton et al., *Prog. Clin. Biol. Res.* 299, 217 (1989), both of which are hereby incorporated by reference. Macrophages secrete cytokines and growth factors that are essential in recruitment of macrophages, lymphocytes, mesenchymal stem cells and fibroblasts into the wound site. Cytokines and growth factors also regulate fibroblast and epithelial cell proliferation, as well as proliferation of endothelial cells for revascularization as disclosed in Rappolee et al., *Curr. Top. Microbiol. Immunol.* 181, 87 (1992) and Nathan, *J. Clin. Invest.* 79, 319 (1987), both of which are hereby incorporated by reference. Accordingly, experiments in macrophage-depleted animals have been associated with defects in wound healing as provided for in Leibovich and Ross, *Am. J. Pathol.* 78, 71 (1975), incorporated in its entirety by reference.

Accelerated wound healing and improved repair and remodeling of damaged tissues is contemplated to be achievable by effectively controlling recruitment of monocytes and differentiation of these cells into activated macrophages. Activated macrophages in turn secrete fibrogenic and angiogenic growth factors inducing formation of granulation tissue containing myofibroblasts as described in Frangogiannis, *Curr. Med. Chem.* 13, 1877 (2006), incorporated herein by reference, and angiogenesis associated with local collagen synthesis and re-epithelization as provided for in Stein et al., *Clin. Exp. Allergy* 22, 19 (1992); DiPietro, *Shock* 4, 233 (1995); Clark, *J. Dermatol. Surg. Oncol.* 19, 693 (1993) and Rappolee et al., *Curr. Topics Microbial Immunol.* 181, 87 (1992), all of which are hereby incorporated by reference. Macrophages have key functions in almost every stage of the wound healing, tissue repair and remodeling processes. Upon initiation of the inflammatory stage, macrophages secrete interleukin-1 (IL-1), which induces the rapid recruitment of inflammatory cells from the circulation into the wound as provided for in Dinarello, *FASEB J.* 2, 108 (1988), incorporated in its entirety by reference. As phagocytes, the macrophages aid in the digestion of bacteria and cell debris as described in Aderem et al., *Ann. Rev. Immunol.* 17, 593 (1999), incorporated herein by reference. In later stages, macrophages secrete interleukin-6 (IL-6), which influences endothelial cell proliferation and initiation of angiogenesis as discussed in Mateo et al., *Am. I Physiol.* 266, R1840 (1994), hereby incorporated by reference. Macrophages further coordinate cellular proliferation by production of growth factors such as α and β vascular endothelial cell growth factors (VGEF), epidermal growth factor (EGF), fibroblast growth factor (FGF) and insulin-like growth factor (IGF) as provided for in Singer et al., *New England Journal of Medicine* 341, 738 (1999), incorporated herein by reference. Moreover, local administration of in vitro activated macrophages into ulcerated wounds, or into wounds resulting from infections following open heart surgery, was found to accelerate the wound healing process as described in Danon et al., *Exp. Gerontol.* 32, 633 (1997) and Orensterin et al., *Wound Repair Regen.* 13, 237 (2005), both of which are incorporated in their entirety by reference.

An additional characteristic attributed to recruited macrophage is the ability of a small proportion of them to function as stem cells. It has been reported that monocytes/macrophages include a small population of multipotential stem cells that can proliferate and undergo trans-differentiation into various types of cells, based on microenvironment and on the adjacent cells. Seta et al., *Keio J. Med.* 56:41 (2007). For example, incubation of human macrophages in presence of chicken cardiomyocytes results in differentiation of a small proportion of cells into human cardiomyocytes. Similarly, incubation of human macrophages with rat fetal neurons results in induction of human stem cells among macrophages to differentiate into neurons. Macrophages are capable of recruiting stem cells from the adjacent uninjured tissue or from other sites in the body, and/or macrophages trans-differentiate into stem cells. The recruitment and activation by the treatment of injection of α-gal liposomes into injured tissues results in rapid migration of stem cells into treated injured tissue and in accelerated repair and regeneration of the injured tissue for the restoration of its pre-injury biological activity. As illustrated in FIG. 1, this recruitment and activation is the result of the interaction between the natural anti-Gal antibody and α-gal epitopes on the injected α-gal liposomes and the subsequent Fc/FcγR interaction between macrophages and the anti-Gal bound to α-gal liposomes.

In some embodiments, the present invention provides for compositions and methods for using the anti-Gal antibody for the recruitment and local activation of neutrophils, monocytes and macrophages within and adjacent to wounded tissue. This is achieved by administration of compositions comprising liposomes bearing multiple α-gal epitopes (Galα1-3Galβ1-(3)4GlcNAc-R) as part of the glycolipid component. The anti-Gal antibody, which constitutes 1% of immunoglobulins in humans, apes, Old World primates and birds, interacts specifically with α-gal epitopes. In situ binding of anti-Gal to α-gal epitopes on α-gal glycolipids and to other molecules carrying this epitope, results in local activation of complement and generation of the chemotactic factors C5a, C4a and C3a. These factors direct migration of neutrophils followed by monocytes and macrophages into the injection site. These inflammatory infiltrates are suitable for combating microbes within infected wounds. In addition, the monocytes and macrophages infiltrates are contemplated to bind by their Fcγ receptors, anti-Gal antibodies via the Fc portion of anti-Gal opsonizing the α-gal liposomes, thereby and activating these cells. This in turn induces the uptake of the anti-Gal opsonized α-gal liposomes and the secretion of cytokines and growth factors that accelerate wound healing. As such treatment regimens comprising α-gal liposomes administration within and/or adjacent to a wound are contemplated to result in accelerated healing and improved repair of damaged tissues. Alternatively, topical application of ointment containing α-gal glycolipids (referred to as α-gal ointments) results in similar binding of anti-Gal to α-gal glycolipids, complement activation, chemotactic migration of neutrophils, monocytes and macrophages into the treated area, local secretion of cytokines and growth factors that contribute to accelerated wound healing.

When a wound occurs to the skin, the cells must work to close the breach and re-establish the barrier to the environment. The process of wound healing typically consists of three phases during which the injured tissue is repaired, regenerated, and new tissue is reorganized into a scar. These three phases can be classified as: a) an inflammation phase which begins on day 0 and lasts up to 3 days; b) a cellular proliferation phase from 3 to 12 days; and c) a remodeling phase from 3 days to about 6 months.

In the inflammation phase, inflammatory cells, mostly neutrophils, enter the site of the wound followed by lymphocytes, monocytes, and later macrophages. Stimulated neutrophils release proteases and reactive oxygen species into the surrounding medium, with potential adverse effects on both the adjacent tissues and the invading microorganisms. The proliferative phase consists of laying down new granulation tissue, and the formation of new blood vessels in the injured area. Fibroblasts, endothelial cells, and epithelial cells migrate to the wound site. These fibroblasts produce the collagen necessary for wound repair. In re-epithelialization, epithelial cells migrate from the free edges of the tissue across the wound. This event is succeeded by the proliferation of epithelial cells at the periphery of the wound. In general, re-epithelialization is enhanced by the presence of occlusive wound dressings that maintain a moisture barrier. Remodeling, the final phase of wound healing, is effected by both the replacement of granulation tissue with collagen and elastin fibers and the devascularization of the granulation tissue. Eventually, in most cases, a scar forms over the wounded area.

I. The Role of Inflammatory Cells in Wound Healing and Tissue Repair

Neutrophils are the first immune cells to arrive at the wound site appearing approximately 24 h after injury. They phagocytose bacteria and mediate wound debridement. Macrophages migrate into the wound 48-96 h after injury and become the predominant cells within the inflammatory response in the wound. Studies on depletion of monocytes and/or macrophages in mice by intravascular administration of specific anti-macrophage antibodies have indicated that wound healing is impaired after depletion of these cells as provided for in Leibovich et al., *Am. I Pathol.* 78, 71 (1975), incorporated herein by reference. In contrast, depletion of granulocytes, including neutrophils, through the use of specific anti-granulocyte antibodies does not hamper the inflammatory response and subsequent wound healing and tissue repair as provided for in Leibovich et al., *Am. I Pathol.* 78, 71 (1975), incorporated herein by reference. This result suggests that cells of the monocyte/macrophage lineage are pivotal in orchestrating wound healing and tissue repair and in remodeling following injury. As such the present invention provides compositions and methods for inducing rapid recruitment of macrophages into wounds and injured tissues to accelerate the process of wound healing and tissue repair. Circulating monocytes enter the wound and mature into macrophages and dendritic cells. They secrete interferon-γ (IFNγ), and angiogenic and fibrogenic growth factors. These factors and additional chemokines, cytokines and growth factors are produced after debridement of the injured tissue and are instrumental in the removal of dead cells, localized recruitment of fibroblasts and mesenchimal stem cells, cell proliferation and tissue remodeling to effect wound healing. This tissue repair process occurs in infected wounds, surgical incisions, burns and other traumatized tissues as disclosed in Rappolee et al., *Curr. Top. Microbiol. Immunol.* 181, 87 (1992); Nathan, *J. Clin. Invest.* 79, 319 (1987) and Singer et al., *New England Journal of Medicine* 341, 738 (1999), all of which are hereby incorporated by reference. Major chemoattractants directing migration of neutrophils, monocytes and macrophages are the C5a and C3a fragments of the complement components C5 and C3, which are generated following complement activation by antigen/antibody interactions. These chemotactic factors form a concentration gradient that guides the migration of neutrophils, monocytes and macrophages to the areas with increased concentrations of C5a and C3a.

In some embodiments, the present invention provides for compositions and methods for the recruitment and activation of large numbers of neutrophils, monocytes and macrophages into wounds by local injection of liposomes possessing multiple α-gal epitopes (Galα1-3Galβ1-4GlcNAc-R or Galα1-3Galβ1-3GlcNAc-R) on their glycolipid components, or by topical application of ointment containing α-gal glycolipids. The α-gal epitopes bind the natural anti-Gal antibody, which is the most abundant antibody in humans. This antigen/antibody interaction in turn activates complement forming the degradation products C5a and C3a that serve as effective chemoattractants for inflammatory cells.

II. Anti-Gal Antibodies And α-Gal Epitopes

Anti-Gal is an abundant natural antibody in humans constituting ~1% of all serum immunoglobulins as provided for in Galili et al., *J. Exp. Med.* 160, 1519 (1984), incorporated herein by reference. This antibody interacts specifically with the α-gal epitope (Gala 1-3Galβ1-4GlcNAc-R or Galα1-3Galβ1-3GlcNAc-R) on glycolipids and glycoproteins as disclosed in Galili, *Springer Semin. Immunopathol.* 15, 155 (1993), incorporated in its entirety by reference. Anti-Gal is produced throughout life as a result of antigenic stimulation by bacteria of the gastrointestinal tract as described in Galili et al., *Infect. Immun.* 56, 1730 (1988). The α-gal epitope is synthesized by the glycosylation enzyme α-1,3-galactosyltransferase (a1,3GT) and expressed in very large amounts on the cells of non-primate mammals, prosimians and in New World monkeys as provided for in Galili et al., *J. Biol. Chem.* 263, 17755 (1988), incorporated herein by reference. The α1,3GT gene was inactivated in ancestral Old World primates. Thus humans, apes, and Old World monkeys lack α-gal epitopes and produce high titer anti-Gal antibodies as provided for in Galili et al., *J. Biol. Chem.* 263, 17755 (1988), incorporated herein by reference. Anti-Gal antibodies bind in vivo to α-gal epitopes when administered to humans or Old World monkeys. This is particularly evident in the context of xenotransplantation, where the in vivo binding of anti-Gal to α-gal epitopes on transplanted pig heart or kidney is the main cause for the rapid rejection of such grafts in humans and Old World monkeys as disclosed in Galili et al., *Immunol. Today* 14, 480 (1993) and Collins et al., *J. Immunol.* 154, 5500 (1995), both of which are incorporated in their entirety by reference.

One of the main mechanisms mediating xenograft rejection is the activation of the complement cascade due to anti-Gal binding to α-gal epitopes on the endothelial cells of the xenograft. This results in the destruction of these endothelial cells by the activated complement molecules, causing collapse of the vascular bed and xenograft ischemia followed by its rapid rejection as provided for in Collins et al., *J. Immunol.* 154, 5500 (1995), hereby incorporated by reference. This in situ interaction of anti-Gal with newly introduced α-gal epitopes can be exploited for local activation of the complement system and recruitment of neutrophils, monocytes and macrophages into damaged tissues to accelerate the inflammatory response and subsequent tissue repair. Due to its ubiquitous production in humans, anti-Gal is a superior choice for this purpose.

III. Binding of Anti-Gal Antibody by α-Gal Liposome

Figure 1B:
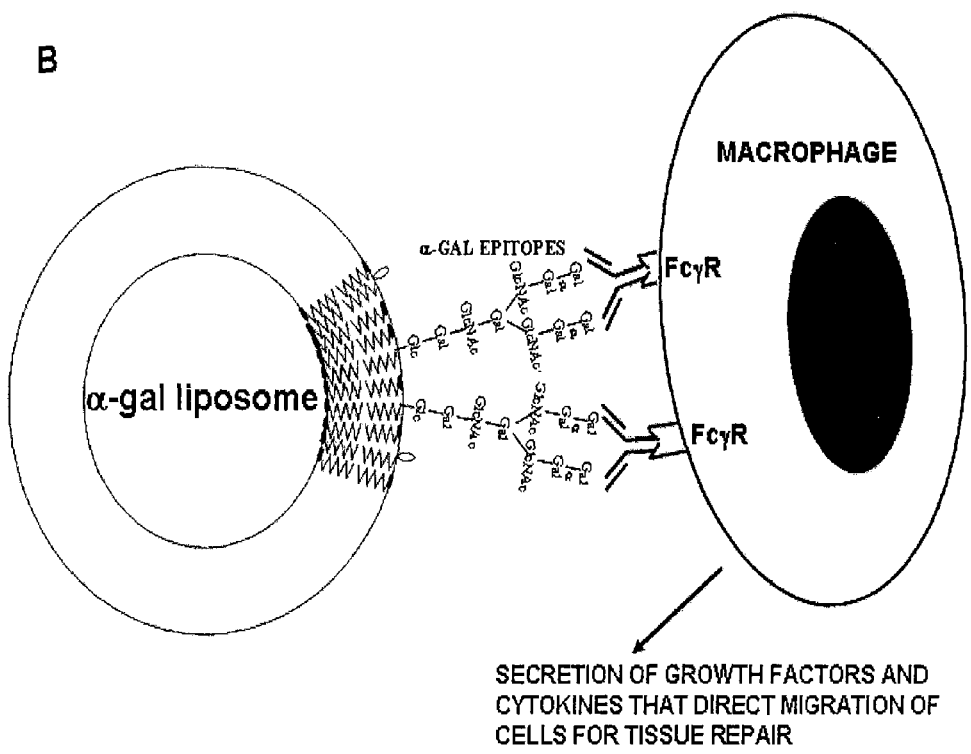
FIG. 1B illustrates an interaction between an anti-Gal coated (opsonized) α-gal liposome and a macrophage.
Figure 2A:
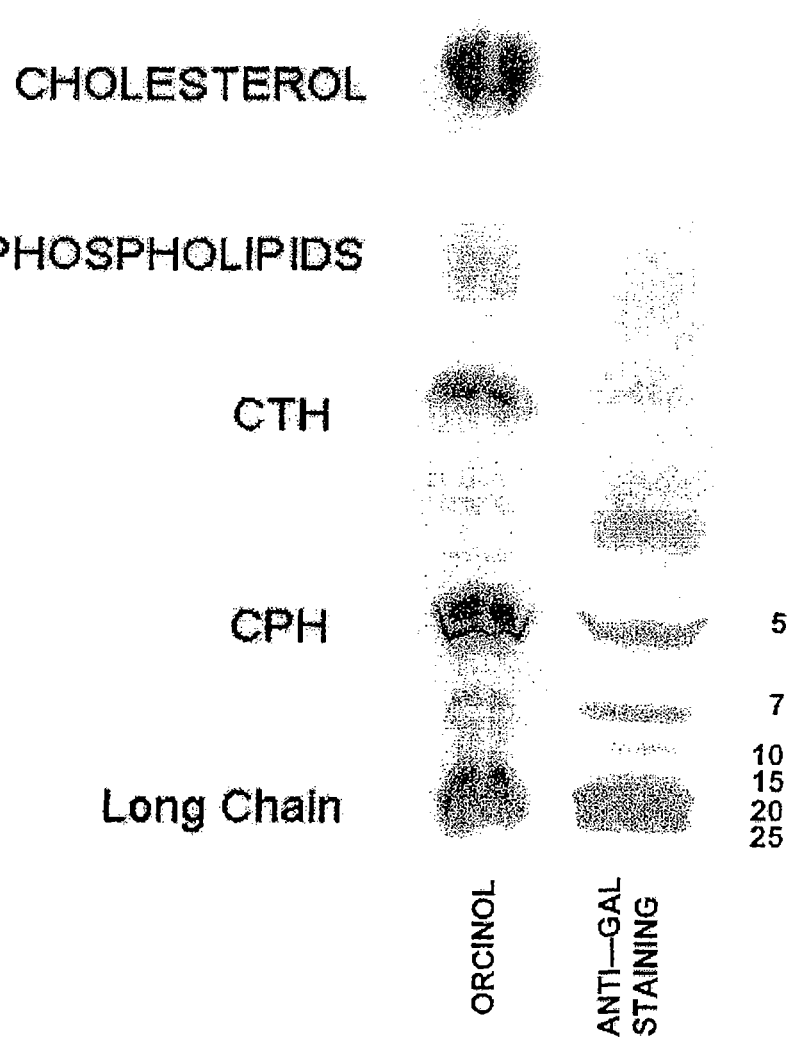
FIG. 2A depicts the separation of rabbit RBC glycolipids, phospholipids and cholesterol by thin layer chromatography (TLC), as demonstrated by nonspecific orcinol staining (left lane) and by immunostaining with an anti-Gal monoclonal antibody (mAb) designated Gal-13 (right lane) (Galili et al., J Biol Chem, 262:4683, 1987). The smallest glycolipids having three carbohydrates (ceramide tri-hexoside [CTH]) lack α-gal epitopes and thus are not stained by the anti-Gal mAb. The number of carbohydrates in each α-gal glycolipid is indicated on the right. The smallest α-gal-containing glycolipid has five carbohydrates (ceramide pentahexoside [CPH]).
Figure 2B:
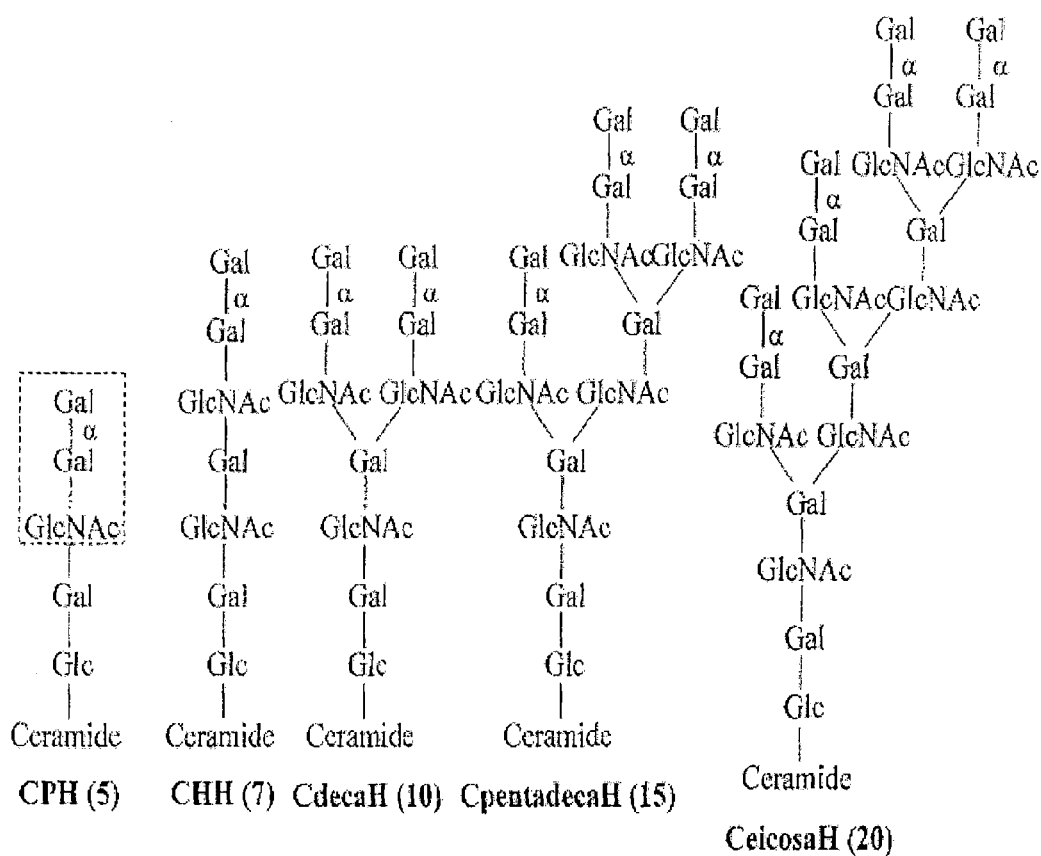
FIG. 2B provides the structures of α-gal glycolipids having five, seven, 10, 15 and 20 carbohydrates, respectively.

Recruitment of neutrophils, monocytes and macrophages into sites of infection or tissue damage is directed by a concentration gradient of fragments of activated complement molecules such as C5a, C4a and C3a. Injection of molecules or particulate material bearing α-gal epitopes is contemplated to result in local interaction between endogenous anti-Gal antibodies and the exogenous α-gal epitopes, followed by activation of the complement system. One example of particulate material carrying multiple α-gal epitopes is α-gal liposomes, which can be prepared from chloroform:methanol extracts of rabbit red blood cell (RBC) membranes as shown in FIGS. 1 and 2. These liposomes are comprised of rabbit RBC glycolipids, phospholipids and cholesterol. Since most rabbit RBC glycolipids have α-gal epitopes, these liposomes carry many of these epitopes. When the α-gal liposomes are injected intradermally or into other tissues, a high local concentration of α-gal epitopes is generated, which is available for binding to anti-Gal antibodies. Both the anti-Gal antibody and complement are contemplated to reach the injection site due to local rupture of capillaries by the injecting needle. The activation of complement and generation of C5a, C4a and C3a fragments, following anti-Gal interaction with α-gal epitopes, results in a local inflammatory reaction that induces capillary dilation, and accumulation of serum proteins at the injection site (including more anti-Gal and complement proteins). This leads to further binding of anti-Gal to the injected α-gal liposomes and activation of complement, ultimately resulting in an amplification of the inflammatory process and the increased formation of chemotactic factors for recruit of additional neutrophils, monocytes and macrophages into the injection site. Other liposomes that bear α-gal epitopes or other molecules carrying one or several α-gal epitopes are also suitable for enhancing the beneficial inflammatory response occurring at the injection site.

The monocytes/macrophages migrating into the injection site bind the anti-Gal coated (opsonized) α-gal liposomes via their Fcγ receptors (FcγR). The interaction of the Fc portion of anti-Gal (upon opsonization of α-gal liposomes) with FcγR on the monocyte and immature macrophage cell surface induces the activation of these cells and the differentiation of the monocytes into mature macrophages. Activated macrophages have been shown to secrete a variety of growth factors and cytokines including for instance: vascular endothelial cell growth factor (VGEF), epidermal growth factor (EGF), fibroblast growth factor (FGF), insulin-like growth factor (IGF), IL-1 and IL-6 as disclosed in DiPietro, *Shock* 4, 233-40 (1995); Rappolee et al., *Curr. Topics Microbial Immunol.* 181, 87-140 (1992) and Singer et al., *New England Journal of Medicine* 341, 738-46 (1999), all of which are hereby incorporated by reference.

The effect of α-gal liposomes on recruitment of macrophages and wound healing is localized to the injection site and has little to no systemic effect. The three components of the exemplary α-gal liposomes, α-gal glycolipids, phospholipids and cholesterol, are not immunogenic and therefore do not elicit a de novo immune response presumably because phospholipids and cholesterol are found in all mammalian species and because α-gal glycolipids in and of themselves do not activate T cells as disclosed in Tanemura et al., *J. Clin. Invest.* 105, 301 (2000). Accordingly, analysis of the antibody response to α-gal liposomes by ELISA (using α-gal liposomes as the solid phase antigen) revealed that antibody titers to α-gal liposomes were not elevated at 35 or 40 days post-injection. Moreover in experiments performed in anti-Gal seropositive mice, administration of α-gal liposomes did not cause abnormal behavior post-injection or increased morbidity or mortality.

Thus, injection of a preparation of α-gal liposomes in water, saline or other excipient into an infected wound, is contemplated to result in anti-Gal binding, activation of complement, generation chemotactic factors, rapid recruitment of neutrophils followed by monocytes and macrophages, phagocytosis of the infectious agent, debridement of the wound, and migration of fibroblasts into the wound. Secretion of epithelial growth factor by the activated macrophages results in epithelization, e.g. proliferation of epithelial cells to close the wound. The destruction of infectious agents and debridement of the wound by the inflammatory cell infiltrate and subsequent migration of fibroblasts and proliferation of epithelial cells is contemplated to accelerate wound healing and tissue repair.

Figure 9:
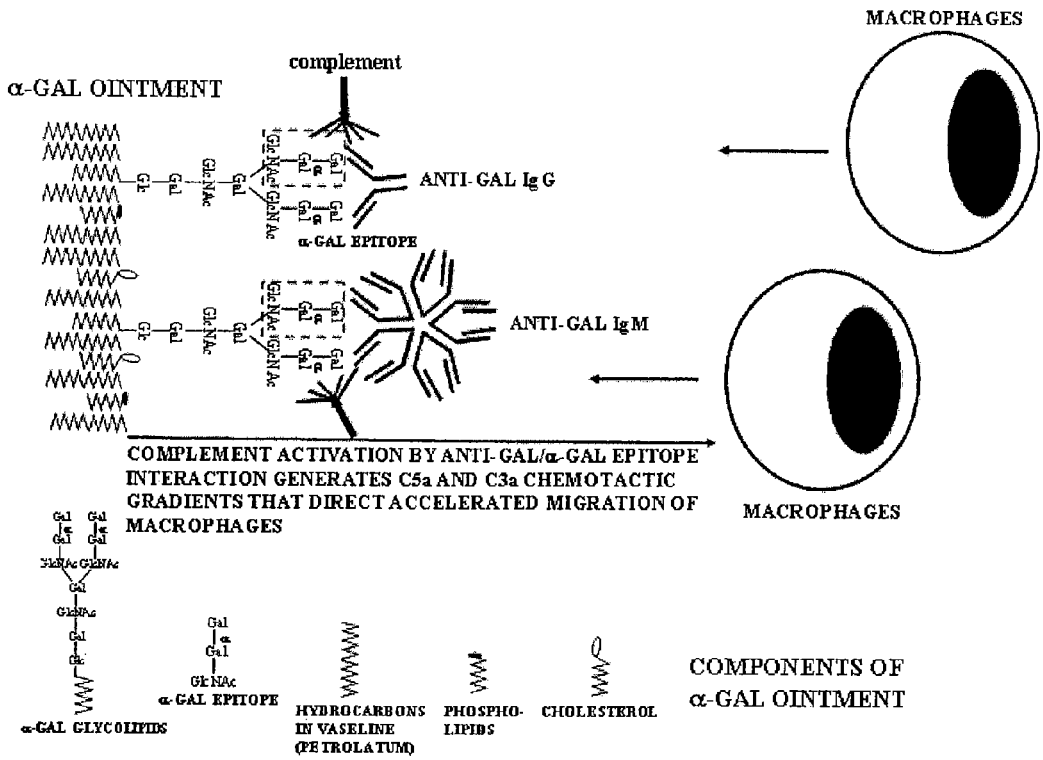
FIG. 9 illustrates one embodiment of an interaction between anti-Gal and α-gal epitopes on α-gal glycolipids applied in the form of α-gal ointment. The α-gal ointment, comprised here of a mixture of α-gal glycolipids (100 mg/ml) and petrolatum ointment (Vaseline), is applied topically on areas of damaged skin such as burns, in which serum proteins including anti-Gal and complement are released from damaged blood vessels. The α-gal epitopes (Galα1-3Galβ1-4GlcNAc-R) indicated on some of the chains in rectangles of broken lines) are present on all rabbit red cell glycolipids that carry 5 or more carbohydrate units (see FIG. 2). The present figure illustrates a representative α-gal glycolipid with 10 carbohydrate units. The fatty tail comprising the ceramide portion of the glycolipid enables mixing of the α-gal glycolipids within petrolatum (Vaseline) containing hydrocarbon chains of >25 carbons. α-Gal glycolipids within the ointment bind anti-Gal and thus, activate complement. The complement cleavage factors C5a and C3a recruit macrophages which mediate the accelerated natural process of wound healing.

A similar accelerated healing of wounds can be achieved by topical application of α-gal ointment onto injured skin areas of various wounds including burns as shown in FIG. 9. The α-gal epitopes of α-gal glycolipids within this ointment bind the anti-Gal antibody, activate complement, generate complement degradation factors C5a and C3a due to cleavage of complement molecules, recruit granulocytes, monocytes and macrophages to the treated site and thus, induce accelerated healing of the injured area.

IV. Wound Healing Applications

The compositions and methods of the present invention are suitable for treating various wounds in normal subjects and in subjects having impaired healing capabilities, such as diabetics, heart disease and/or cardiac surgical subjects, and aged subjects.

In one embodiment, the present invention contemplates a method for inducing rapid recruitment and activation of macrophages by α-gal liposomes that interact with natural anti-Gal antibodies. In one embodiment, the α-gal liposomes accelerate wound healing while reducing scar formation. Although it is not necessary to understand the mechanism of an invention, it is believed that because humans naturally produce anti-Gal antibodies that constitute ~1% of IgG, IgM and IgA immunoglobulins in their serum, topical application of α-gal liposomes may result in accelerated wound healing also in a clinical setting. Galili et al., 1984 "A unique natural human IgG antibody with anti-α-galactosyl specificity" *J. Exp. Med.* 160:1519-1531; Galili, U, 2005 "The α-gal epitope and the anti-Gal antibody in xenotransplantation and in cancer immunotherapy" *Immunology and Cell Biology* 83:674-686; Hamadeh et al. 1995 "Human secretions contain IgA, IgG and IgM anti-Gal (anti-α-galactosyl) antibodies" *Clin. Diagnos. Lab. Immunol.* 2:125-131; and Parker et al., 1994 "Characterization and affinity isolation of xenoreactive human natural antibodies" *J. Immunol.* 153(8):3791-803.

Very high amounts of α-gal epitopes on glycolipids of α-gal liposomes may enhance their interaction with anti-Gal antibodies and induce a strong complement activation. Since there are ~$10^{15}$ α-gal epitopes/mg α-gal liposomes, topical application on wounds is believed to result in a high concentration of α-gal epitopes on a wound surface, thereby allowing for a robust local interaction with anti-Gal antibodies released from damaged capillaries and the ensuing local activation of the complement cascade.

Liposomes that do not express α-gal epitopes have been used in wound healing as vesicles for delivery of substances to wounds that affect wound healing such as superoxide dismutase, hemoglobin, or of genes that encode growth factors. Vorauer-Uhl et al., 2002 "Reepithelialization of experimental scalds effected by topically applied superoxide dismutase: controlled animal studies" *Wound Repair Regen.* 10:366-371; Plock et al., 2009 "Hemoglobin vesicles improve wound healing and tissue survival in critically ischemic skin in mice" *Am J Physiol Heart Circ Physiol.* 297:H905-910; and Jeschke et al., 2007 "The combination of IGF-I and KGF cDNA improves dermal and epidermal regeneration by increased VEGF expression and neovascularization" *Gene Ther.* 14:1235-1242, respectively.

Although it is not necessary to understand the mechanism of an invention, it is believed that the α-gal liposomes deliver multiple α-gal glycolipids in their membranes, rather than within the liposomes, to mediate their therapeutic effects. The data presented herein show that α-gal liposome treatment, when compared to other wound healing treatments, has the distinct advantage of harnessing of at least two immunological mechanisms for accelerating the healing process: i) anti-Gal/α-gal liposome interaction activates complement to produce complement cleavage peptides that induces rapid extravasation of monocytes, conversion of the extravasating monocytes into macrophages, and chemotactic migration into the treated wound; and ii) Fc/FcγR interaction between anti-Gal coated α-gal liposomes and recruited macrophages results in activation these cells and secretion of cytokines that promote wound healing.

These data confirm that anti-Gal/α-gal liposome interaction activates complement using a complement consumption assay. For example, the effect of complement activation on macrophage recruitment was demonstrated in vivo in KO mice by inhibition of macrophage recruitment in the presence of cobra venom factor, a potent inhibitor of complement activation. In addition to the generation of large activated macrophages, activation of these cells led to their production of cytokines. Increased expression of IL1α, IL6, Pdgfb, Fgf2, Csf1, Csf2, Tnf, and VEGF suggested that these genes may be involved in wound healing.

TNFα is considered to be a proinflammatory cytokine that is also involved in induction of early angiogenesis. Wang et al., 1999 "Macrophages are a significant source of type 1 cytokines during mycobacterial infection" *J Clin Invest.* 103 (7):1023-1029; and Arras et al., 1998 "Monocyte activation in angiogenesis and collateral growth in the rabbit hindlimb" *J Clin Invest.* 101(1):40-50. Also observed was that anti-Gal coated α-gal liposomes activated macrophages to secrete VEGF in vitro.

One of the earliest morphological events associated with the anti-Gal/α-gal liposome interaction is redness around an injection site (i.e., for example, at approximately 48 h post injection). Although it is not necessary to understand the mechanism of an invention, it is believed that this redness may reflect local angiogenesis due to secretion of VEGF from activated macrophages and/or vasodilation of capillaries and small blood vessels in the area of this antibody/antigen interaction. It is possible that the vasodilation is induced by complement cleavage peptides in a manner similar to the initiation of an immune mediated inflammatory response due to antibodies binding to invading bacteria.

In one embodiment, the present invention contemplates that rapid recruitment and/or activation of macrophages by anti-Gal/α-gal liposome immune complexes leads to accelerated wound healing. For example, by comparing the extent of epidermis regeneration in α-gal liposome treated wounds to that in control wounds, this treatment is believed to decrease the healing time by ~50%. The data presented herein demonstrate histologic observations of macrophages wherein α-gal liposome treated wounds at 72 h was associated with regeneration of epidermis on day 6. One possible mechanism for this effect is that anti-Gal/α-gal liposome interaction may induce a rapid recruitment of the macrophages and the activation of these cells to produce cytokines that mediate wound healing. These observations are consistent with the skin burn healing data, also presented herein.

Although it is not necessary to understand the mechanism of an invention, it is believed that an increased production of cytokines by activated macrophages may promote healing in association with reduced hyperplasia in skin tissues and a decrease in scar formation in healing wounds. Formation of scar tissue, i.e. of a dense connective tissue lacking skin appendages, is a physiologic default mechanism for wound healing that occurs after the closure of the wound with regenerating epidermis. A rapid anti-Gal mediated activation of recruited macrophages may secrete cytokines that promote tissue healing thereby leading to a restoration of the cellular components of normal skin, prior to the initiation of the scar formation process. The histological data showing long term recovery (i.e., for example, day 28) strongly suggests that the α-gal liposome treatment does not induce hyperplasia and formation of scars in the skin tissues during the healing process.

Activation of macrophages in wounds has been demonstrated by application of immunomodulating substances such as carrageenan and/or BCG. Kelley et al., 1988 "Influence of hypercholesterolemia and cholesterol accumulation on rabbit carrageenan granuloma macrophage activation" *Am J. Pathol.* 131:539-546; and Aguiar-Passeti et al., 1997 "Epithelioid cells from foreign-body granuloma selectively express the calcium-binding protein MRP-14, a novel down-regulatory molecule of macrophage activation" *J Leukoc Biol.* 62:852-858. However, these treatments also result in a non-beneficial prolonged inflammatory immune responses that may be manifested as a chronic granulomas.

Figure 28:
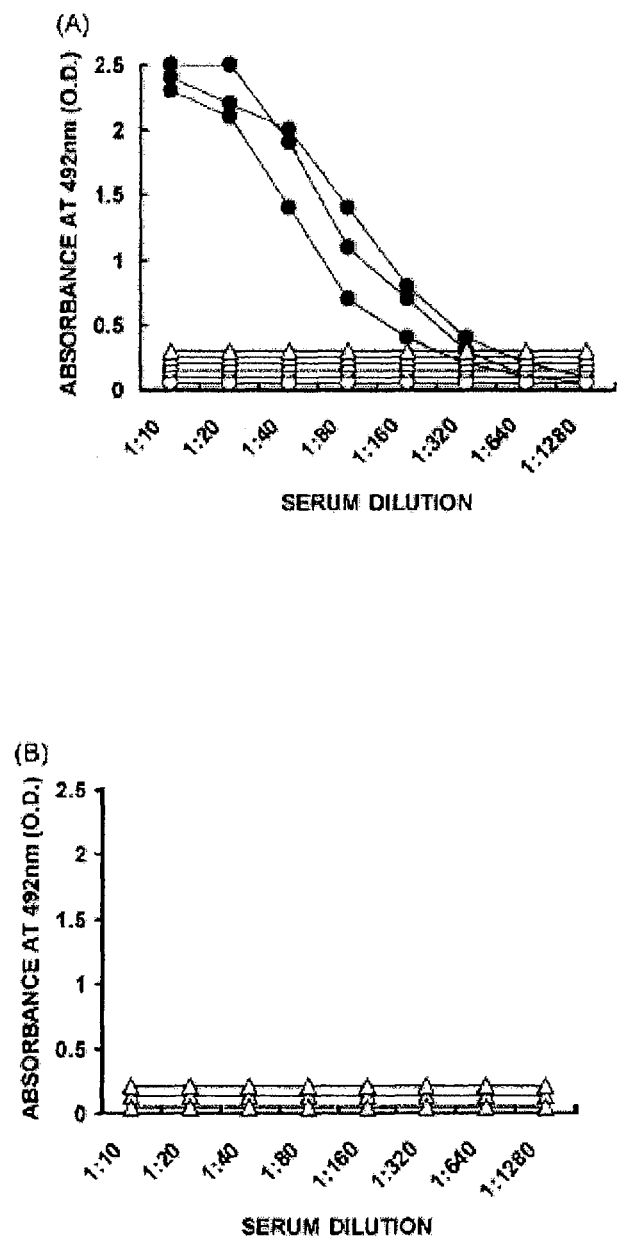
FIG. 28 presents exemplary data showing a representative analysis of an immune response to α-gal liposomes. Anti-liposomes IgG antibodies were measured by ELISA in wells coated with to α-gal liposomes as solid phase antigen. KO mice immunized with PKM served as positive control.

Subsequent to α-gal liposome treatment, however, no chronic granuloma formation was observed in wound healing, for example, by at least one month after initiation of α-gal liposome treatment. Although it is not necessary to understand the mechanism of an invention, it is believed that this implies that the rapid recruitment and activation of macrophages is not followed by any additional immune response to the treating substance. It is believed that α-gal liposomes lack immunogenicity because they do not contain any antigenic proteins capable of activating T cells. Tanemura et al., 2000 "Differential immune responses to α-gal epitopes on xenografts and allografts: implications for accommodation in xenotransplantation" *J. Clin. Invest.* 105:301-310. The data presented herein confirms that no antibody response was observed in α-gal liposome treated KO mice, whereas mice immunized with pig kidney membranes (PKM) (positive control) readily produced antibodies that bound to the α-gal liposomes. See, FIG. 28A. The PKM-induced antibodies are exclusively anti-Gal as indicated by their complete neutralization (i.e. lack of binding to the α-gal liposomes) by α-gal BSA (i.e. synthetic α-gal epitopes linked to BSA). Topical application of 10 mg α-gal liposomes on burns for 2 weeks also did not induce any antibody response. See, FIG. 28B. Since IgG response requires both T helper and B cells activation, these data imply that α-gal liposomes treatment does not elicit a new immune response.

The α-gal epitope itself, like other antigens comprised of carbohydrate chains of the complex type (e.g. blood group A and B antigens), does not activate T cells. In the absence of T cell help, the α-gal epitope also does not elicit a B cell immune response. Galili, U., 2004. "Immune response, accommodation and tolerance to transplantation carbohydrate antigens" *Transplantation* 78:1093-1098. Moreover, the interaction between FcγR on the recruited macrophages and anti-Gal coating the α-gal liposomes results in the rapid internalization of these liposomes due to effective phagocytosis and their elimination from the wound. Following the removal of liposomes, the recruited macrophages disappear within 3-4 weeks and do not elicit a chronic immune response or a granuloma within the treated wound.

Treatment with α-gal liposomes in the clinical setting is of potential significance. Decreasing the healing time of wounds will reduce morbidity as well as decrease the costs associated with acute and chronic wound treatment, which are expected to increase significantly in the coming years. Sen et al., 2009 "Human skin wounds: a major and snowballing threat to public health and the economy" *Wound Repair Regen.* 17:763.

Observations suggesting that the accelerated wound healing may be observed in human patients with wounds treated with α-gal liposomes include, but are not limited to: i) anti-Gal antibodies are present in very large amounts in all humans that are not severely immunocompromised; ii) anti-Gal antibodies in human serum effectively binds to α-gal liposomes and induces complement activation; iii) human anti-Gal antibodies immunocomplexed with α-gal epitopes readily binds to FcγR on macrophages; and iv) cultured human macrophages activated in vitro by hypotonic shock were found to accelerate wound healing in patients with deep sternal wounds and with ulcers. Orenstein et al., 2005 "Treatment of deep sternal wound infections post-open heart surgery by application of activated macrophage suspension" *Wound Repair Regen.* 13:237-242; and Danon et al., 1997 "Treatment of human ulcers by application of macrophages prepared from a blood unit" *Exp Gerontol.* 32:633-641.

Another advantage of administering α-gal liposomes on wound dressings is an ease of use when compared to injection of activated macrophages into wounds. Topical adminsitrations do not require specialized equipment and facilities for in vitro culturing of macrophages. It is further possible that the treatment with α-gal liposomes in humans may be even more effective than the KO mice data described herein as complement activity in human serum is many fold higher than that in mouse serum. Galili et al., 2007 "Intratumoral injection of α-gal glycolipids induces xenograft-like destruction and conversion of lesions into endogenous vaccines" *J. Immunol.* 178:4676-4687. Anti-Gal is believed to be present in all individuals who are not severely immunocompromized, including diabetic patients and elderly individuals. Galili et al., 1995 "Increased anti-Gal activity in diabetic patients transplanted with fetal porcine islet cell clusters" *Transplantation* 59:1549-1556; and Wang et al., 1995 "Variations in activity of the human natural anti-Gal antibody in young and elderly populations" *J. Gerontol. (Med. Sci.)* 50A: M227-M233. Consequently, the effective recruitment and activation of macrophages by α-gal liposomes may "jumpstart" the healing process in chronic wounds of diabetic patients and elderly individuals who display impaired wound healing.

α-gal liposomes are believed to be highly stable and their α-gal epitopes do not alter their structure during prolonged storage. α-gal epitopes, in contrast to biologically active proteins, have no folding or tertiary structures leading to their robust stability. Furthermore, α-gal epitopes do not undergo oxidation for prolonged periods and can be stored for years without losing activity.

This conclusion can be inferred from studies on blood group antigens. The structure of the α-gal epitope is very similar to that of blood group A and B antigens. Galili et al., 1985 "Human natural anti-α-galactosyl IgG. II. The specific recognition of a (1-3)-linked galactose residues" *J. Exp. Med.* 162: 573-582; Galili et al., 2002 "Anti-Gal A/B, a novel anti-blood group antibody identified in recipients of ABO incompatible kidney allografts" *Transplantation* 74:1574-1580. Because of their stability, these blood group antigens can be detected in >2000 yr old Egyptian mummies. Crainic et al., 1989 "ABO tissue antigens of Egyptian mummies" *Forensic Sci Int.* 43:113-124. Thus, if α-gal liposomes are found to be effective in accelerating wound healing in humans, they can be stored for prolonged periods and delivered to wounds in many forms including sprays, hydrogels, on wound dressings, in suspension, or incorporated into devices and dressings that are currently used for treating injuries. Repair and regeneration of internal injured tissues has been suggested to be dependent on effective local recruitment and activation of macrophages. Duffield et al., 2005 "Selective depletion of macrophages reveals distinct, opposing roles during liver injury and repair" *J Clin Invest.* 115:56-65. Therefore, it is possible that delivery of α-gal liposomes to such injuries (e.g. ischemic tissue and trauma injuries) may result in the accelerated repair and regeneration of the biological activity of the injured tissue, while avoiding irreversible scar formation.

A. Surgical Incisions

In a preferred embodiment, compositions comprising α-gal liposomes are used to enhance wound healing in surgical incision sites that have been damaged as a result of ischemia. Injection of α-gal liposomes into the area surrounding the sutures and ischemic tissue enhances recruitment of neutrophils, monocytes and macrophages into the surgical incision site ultimately resulting in improved wound healing. In this way, the present invention is suitable for shortening the time required for healing of wounds and repair of damaged tissues following surgery. A specific non-limiting example is the removal of a colon carcinoma and reconnection of the colon wall at the site of tumor resection.

B. Cardiac Tissue

In another embodiment, compositions comprising α-gal liposomes are used to treat tissue. While not limiting the scope of the invention in any way, one example contemplated by the invention is the treatment of skeletal muscle damaged due to physical trauma or heart muscle damaged due to ischemia. Injection of α-gal liposomes into the injured or damaged muscle tissue enhances recruitment of neutrophils, monocytes and macrophages into the injured muscle ultimately resulting in improved tissue repair. In particular the inflammatory cell infiltrate recruits stem cells or myoblasts, which subsequently differentiate into functional cardiac myocytes in treated heart muscle, or fuse and differentiate into functional skeletal muscle fibers in treated skeletal muscle. In this way the biomechanical function of the damaged muscle is restored.

In preferred embodiments, the compositions and methods of the present invention are used to promote healing due to cardiac tissue damage in both normal subjects and in subjects having impaired healing capabilities. For example, the heart is comprised of myocardium tissue. This tissue may be damaged or otherwise compromised during cardiac trauma, disease or related events including but not limited to cardiac surgery, coronary heart disease, cardiomyopathy, cardiovascular disease, ischemic heart disease, myocardial infarction, heart failure, hypertensive heart disease, inflammatory heart disease and valvular heart disease. Mortality rates for cardiac surgical procedures continue to be a cause for concern. For example, repairs of congenital heart defects are currently estimated to have 4-6% mortality rates. One non-limiting example of wounds that may receive benefit from the compositions and methods of the present invention are infected deep sternum incisions that are observed in an appreciable number of open-heart surgery patients. Injection of α-gal glycolipid preparations (e.g., α-gal liposomes) into the infected area of the sternum enhances recruitment of neutrophils, monocytes and macrophages into the surgical incision site ultimately resulting in improved wound healing.

In another embodiment α-gal liposomes are injected into cardiac muscle injured by ischemia. These injected α-gal liposomes bind in situ the endogenous natural anti-Gal antibody. This antigen/antibody interaction of α-gal liposomes/anti-Gal results in local activation of the complement system and generation of the chemotactic cleavage complement peptides C5a, C4a and C3a. These chemotactic factors direct the migration of macrophages into the injection site. Some of the macrophages have the potential of becoming stem cells. The macrophages further bind the anti-Gal coated α-gal liposomes via their Fcγ receptors (FcγR) are activated by this interaction. This activation results in the secretion of a variety of cytokines growth factors. In addition, the activated macrophages induce local angiogenesis and generate a microenvironment that may be conducive to the recruitment of stem cells from adjacent uninjured myocardium or from other sites in the body. Stem cells recruited by the α-gal liposomes treatment receive instructive cues from uninjured cardiomyocytes, from the cytoskeleton of the heart muscle and from the microenvironment within the heart muscle and develop into cardiomyocytes that repopulate the injured myocardium. Ultimately the treatment with α-gal liposomes injected into the injured heart muscle result in repair and regeneration of the heart muscle and restoration of the heart muscle function.

C. Nerve Tissue

Moreover, injection of α-gal liposomes into nerves damaged by physical or other trauma, or because of nerve degeneration, enhances recruitment of neutrophils, monocytes and macrophages. The activated macrophages debride the damaged nerve tissue and secrete nerve growth factors that induce axonal regeneration and restoration of nerve pulse conductivity via the regenerating nerve. This is contemplated to result in partial or complete restoration of function of the treated nerve.

In one embodiment, the present invention contemplates compositions and methods to recruit stem cells, for healing and/or repairing damaged or injured brain tissue. In one embodiment, α-gal liposomes are injected intracranially into injured brain areas. In one embodiment, the brain is a human brain. In one embodiment, the brain injury comprises damage including, but not limited, that following ischemic infarction. In one embodiment, the α-gal liposomes are injected at any volume that is suitable for injection into the injured brain tissue and at a concentration ranging between 0.01 and 500 mg/ml. Although it is not necessary to understand the mechanism of an invention, it is believed that the interaction between the injected α-gal liposomes and the anti-Gal antibody activates complement and the generated chemotactic complement cleavage peptides recruit monocytes and macrophages to the injection site. The macrophages are activated by Fc/FcγR interaction with anti-Gal coated α-gal liposomes and secrete cytokines and growth factors that promote healing of the injured brain tissue and recruit stem cells. These stem cells proliferate and differentiate in to brain cells that repair and regenerate the injured brain tissue.

D. Burns

In further embodiments, compositions comprising α-gal glycolipids and/or α-gal epitopes are applied to skin burns. Their interaction with the anti-Gal antibody, leaking to the burn surface together with other serum proteins, results in complement activation recruitment of neutrophils, monocytes and macrophages and ultimately resulting in accelerated healing of the burn.

Figure 27:
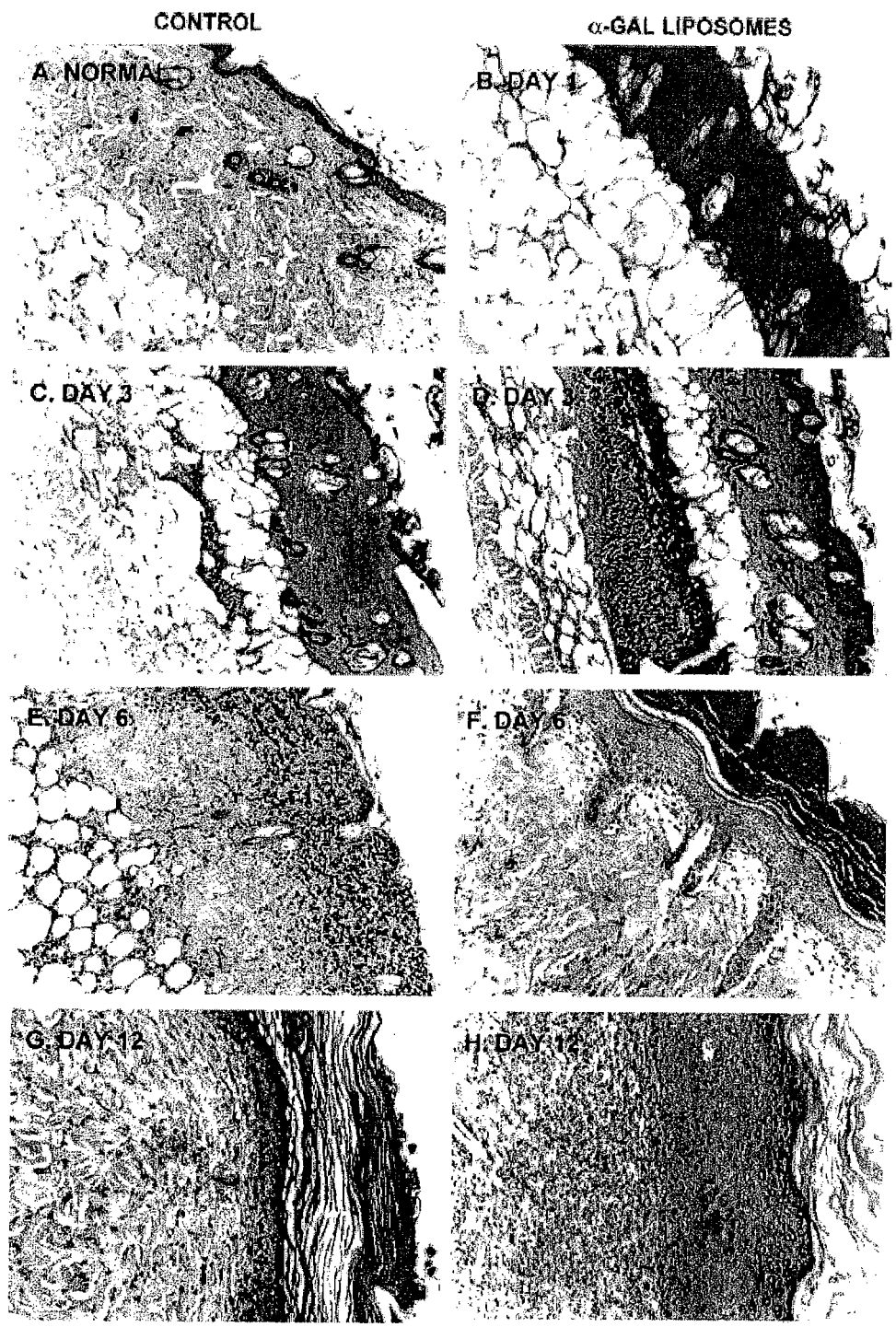
FIG. 27 presents exemplary photomicrographs of the histological (H&E) characteristics of skin burns covered with spot bandages that were coated with 10 mg α-gal liposomes, or with control bandages coated with saline. The burns were examined at various time points as pairs obtained from the same mouse and are representative of five mice at each time point. (A) is an exception presenting normal noninjured KO mouse skin (×200).

The data presented herein was collected in accordance with Example 26. Normal mouse skin displays an epidermis comprised of 2-3 layers of epithelial cells, the underlying dermis stained pink, and the hypodermis containing multiple fat cells. See, FIG. 27A. As in second degree burns in humans, the thermal injury in mouse skin destroys both epidermis and dermis, whereas damage to the hypodermis is minimal. See, FIG. 27B. No significant differences between experimental (α-gal liposomes) and control (saline) treatments are observed 1 day after injury (not shown).

On Day 3, the number of neutrophils migrating into the hypodermis of burns treated with α-gal liposomes was several fold higher than in control burns. See, FIGS. 27C and 27D. Mononuclear cells with morphology of macrophages are detected only in the α-gal liposomes treated burns.

On Day 6, α-gal liposomes treated burns display extensive regeneration of epidermis as 50-100% re-epithelialization of the surface areas with newly formed epidermis. See, FIG. 27F. However, epidermis regeneration in control burns is only marginal on Day 6. See, FIG. 27E. Recruited neutrophils in α-gal liposomes treated burns are found on Day 6 on the surface of the regenerating epidermis, whereas many mononuclear cells with macrophage morphology are detected in the dermis. See, FIG. 27F. In contrast, neutrophils are found mostly within the outer region of the injured dermis in saline treated burns and the number of macrophages is relatively low. See, FIG. 27E. In both treatments, the dermis region is filled with eosinophilic material which may reflect local secretion of collagen.

The accelerated healing of the α-gal liposomes treated burns, is dose dependent. Treatment for 6 days with bandages coated with 1.0 mg instead of 10 mg α-gal liposomes results on average in 23% regeneration of the epidermis instead of 70% observed with the higher dose. No significant differences are observed in healing of burns treated with 0.1 mg α-liposomes and healing of control burns treated with saline.

On Day 9, regenerating epidermis covers on average 25% of burn surface in control burns and 85% of surface area in α-gal liposomes treated burns. By Day 12, epidermis regeneration is complete in both groups. See, Table 1.

TABLE 1

Summary of histological characteristics in burns treated with α-gal liposomes

| Days post treatment | Treatment of burn | [a]number of neutrophils | [a]number of macrophages | [b]% of epidermis regeneration |
|---|---|---|---|---|
| [c]3 | Saline control | 132 + 18 | 0 | 0 |
|  | α-gal liposomes | 520 + 87 | 41 + 27 | 7 + 2.8 |
| [c]6 | Saline control | 173 + 47 | 24 + 16 | 6 + 4.1 |
|  | α-gal liposomes | Neutrophils above the epidermis | 84 + 35 | 70 + 23 |
| [c]9 | Saline control | 235 + 95 | 37 + 12 | 25 + 11 |
|  | α-gal liposomes | No visible neutrophils | 105 + 10 | 85 + 14 |
| [c]12 | Saline control | No visible neutrophils | 21 + 5.3 | 100 |
|  | α-gal liposomes | No visible neutrophils | 96 + 26 | 100 |

TABLE 1-continued

Summary of histological characteristics in burns treated with α-gal liposomes

| Days post treatment | Treatment of burn | [a]number of neutrophils | [a]number of macrophages | [b]% of epidermis regeneration |
|---|---|---|---|---|
| [d]3 in WT[e] mouse | Saline control | 124 + 26 | 17 + 7.1 | 0 |
| | α-gal liposomes | 134 + 48 | 21 + 9.6 | 0 |
| [d]6 in WT mouse | Saline control | 141 + 33 | 39 + 16 | 0 |
| | α-gal liposomes | 153 + 64 | 37 + 13 | 8 + 7.3 |

[a]Number of infiltrating cells was determined in histological sections by counting cells within a rectangular area marked in the microscope lens at magnification of ×400. The rectangle with a size corresponding to 100 × 200 μm was placed to include both dermis and hypodermis. Neutrophils were identified by segmented nuclei and macrophages were tentatively identified by the kidney or oval shaped nuclei and large size of the cells.
[b]% of epidermis regeneration was determined histologically by the proportion of the burn surface covered with the newly formed epidermis.
[c]Mean + Standard Deviation from 5 mice per group;
[d]Mean + Standard Deviation from 4 mice per group.
[e]WT = Wild Type

E. Diabetes

In an additional embodiment, the disclosed α-gal liposome can be combined in compositions with at least one anti-Gal antibody. The mixture of these antigen and antibody will result in increased recruitment of neutrophils, monocytes and macrophages to the injured area. Such treatment is ideal, for example, for aged individuals or subjects with advanced diabetes patients where poor vascularization prevents sufficient anti-Gal antibody from reaching injured areas. Alternatively, such treatment may be applicable to non-primate mammals lacking the anti-Gal antibody. The applied immune complexes activate complement and thus accelerate wound healing.

In some embodiments, the local anti-Gal mediated activation of complement and subsequent recruitment of activated macrophages into an injection site is achieved by employing a variety of natural or synthetic macromolecules carrying multiple α-gal epitopes. Various commercially available glycolipids (Dextra Laboratories, Ltd., United Kingdom) are suitable for use in the compositions and methods of the present invention for generation of α-gal liposomes. These glycolipids include but are not limited to: i) Gala-3Gal glycolipids: α1-3 galactobiose (G203); linear B-2 trisaccharide (GN334); and Galili pentasaccharide (L537). Various other glycoconjugates with α-gal epitopes available from Dextra include for instance: Galα1-3Galβ1-4Glc-BSA (NGP0330); Galα1-3Galβ1-4(3-deoxyGlcNAc)-HAS (NGP2335); Galα1-3Galβ1-4GlcNAcβ1-HDPE (NGL0334); and Galα1-3Gal-BSA (NGP0203). Several non-limiting examples of additional macromolecules with α-gal epitopes that are suitable for injection and subsequent in situ binding to anti-Gal antibodies and local activation of complement include: mouse laminin with 50-70 α-gal epitopes as disclosed in Galili, *Springer Seminars in Immunopathology* 15, 155 (1993), incorporated herein by reference; multiple synthetic α-gal epitopes linked to BSA as disclosed in Stone et al., *Transplantation* 83, 201 (2007), hereby incorporated by reference; GAS914 produced commercially by Novartis and disclosed in Zhong et al., *Transplantation* 75, 10 (2003), incorporated herein by reference; the α-gal polyethylene glycol conjugate TPC as disclosed in Schirmer et al., *Xenotransplantation* 11, 436 (2004), hereby incorporated by reference, and α-gal epitope-mimicking peptides linked to a macromolecule backbone as disclosed in Sandrin et al., *Glycoconj. J.* 14, 97 (1997), hereby incorporated by reference. Injection or topical application of such macromolecules results in local interaction with the pre-formed anti-Gal antibody present in all humans, activation of complement, recruitment of inflammatory cells into the injection site and differentiation of these cells thereby effecting improvements in the duration and quality of wound healing.

In still further embodiments a glycoprotein carrier such as the human alpha1-acid glycoprotein (α1-AG) is utilized. α1-AG is abundant in human serum, non-immunogenic in humans, and can be obtained commercially in purified form. α1-AG is a small glycoprotein (e.g., 40 kDa) with five N-linked carbohydrate chains, each with 2 or more antennae with the terminal structure sialic acid-Galβ1-4GlcNAc-R as disclosed in Schmid et al., *Biochemistry* 13, 2694-2697 (1973), incorporated herein by reference. To synthesize the α-gal epitopes on the α1-AG the sialic acid is first removed to expose the penultimate N-acetyllactosamine (Galβ1-4GlcNAc-R). Next the appropriate carbohydrate is added to this backbone to synthesize the α-gal epitope. Briefly, neuraminidase is used to remove the terminal sialic acid, followed by the addition of an α1-3Gal unit using a galactosyltransferase (e.g., recombinant α1,3 galactosyltransferase) and uridine diphosphate-galactose as the sugar donor as disclosed in Galili, *Cancer Immunol. Immunother.* 53, 935-945 (2004), hereby incorporated by reference.

F. Osteoarthritis (OA)

In preferred embodiments, the methods and compositions of the present invention are used to reduce the symptoms associated with osteoarthritis (OA), a disease that may also be referred to as degenerative arthritis. Traditionally, treatment for osteoarthritis is limited to pain relievers including but not limited to non-steroidal anti-inflammatory drugs (NSAIDS), corticosteroids, COX-2 selective inhibitors and topical creams. In more severe cases of OA the subject receives either injections of local anesthetics such as lidocaine or undergoes joint replacement surgery for the affected area. In a further embodiment, injection of α-gal liposomes into the synovial cavity, or into damaged cartilage within injured bones enhances recruitment of neutrophils, monocytes and macrophages into the synovial cavity or cartilage ultimately resulting in tissue repair. In particular, macrophages activated by the binding of α-gal liposome/anti-Gal antibody complexes mediate debridement of the damaged cartilage and through secretion of growth factors and cytokines direct migration of chondroblasts into the damaged cartilage. The chondroblasts in turn secrete collagen and other cartilage matrix proteins and polysaccharides, resulting in repair and remodeling of the damaged articular or meniscus cartilage within the treated joint. Similarly, macrophages activated by the binding of α-gal liposome/anti-Gal antibody complexes mediate debridement of the damaged bone and through secretion of growth factors and cytokines recruit osteoclasts and osteoblasts into the injection site for repair and remodeling of the damaged bone.

In a further embodiment, injection of α-gal liposomes into the synovial cavity, or into damaged cartilage within injured bones enhances recruitment of neutrophils, monocytes and macrophages into the synovial cavity or cartilage ultimately resulting in tissue repair. In particular, macrophages activated by the binding of α-gal liposome/anti-Gal antibody complexes mediate debridement of the damaged cartilage and through secretion of growth factors and cytokines direct migration of chondroblasts into the damaged cartilage. The chondroblasts in turn secrete collagen and other cartilage matrix proteins and polysaccharides, resulting in repair and remodeling of the damaged articular or meniscus cartilage within the treated joint. Similarly, macrophages activated by the binding of α-gal liposome/anti-Gal antibody complexes mediate debridement of the damaged bone and through secretion of growth factors and cytokines recruit osteoclasts and osteoblasts into the injection site for repair and remodeling of the damaged bone.

G. Diabetes

In preferred embodiments, the present invention is used to promote healing in tissue damage as a result of diabetes in both normal subjects and in subjects having impaired healing capabilities. Diabetes can cause many complications, including but in no way limited to acute complications such as hypoglycemia, ketoacidosis, or non-ketotic hyperosmolar coma, long-term complications including but not limited to cardiovascular disease, chronic renal failure, retinal damage, blindness, nerve damage and microvascular damage. Poor healing of many superficial wounds due to diabetes can lead to many diseases including but not limited to gangrene, which may require amputation. In the developed world, diabetes is the most significant cause of adult blindness in the non-elderly and the leading cause of non-traumatic amputation in adults, and diabetic nephropathy is the main illness requiring renal dialysis in the United States. The α-gal liposomes of the present invention may be preferably used in wound care devices in patients with diabetes, in order to induce effective wound healing by local activation of complement as a result of anti-Gal antibody binding to α-gal liposomes. In still another embodiment, the invention relates to the use of α-gal liposomes in wound care devices applied to a wound in a subject following either diabetic complications or the natural progression of the disease.

In another embodiment, α-gal liposomes are used for injection into the pancreas in diabetic patients, in order to restore the formation of Langerhans Islets in the pancreas. These islets contain cells that secrete insulin. Injection of α-gal liposomes at a concentration ranging between 0.01 and 500 mg/ml. The injection is performed by ultrasound endoscopy, or by laparoscopy, or any other type of injection, into the pancreas tissue of diabetic patients induces the recruitment and activation of macrophages that promote tissue repair. Some of these macrophages have stem cell potential and can differentiate into Langerhans Islet cells. In addition, the activated macrophages secrete cytokines and growth factors that promote recruitment of stem cells which give rise within the pancreas to formation of Langerhans Islets, which secrete several hormones and include, but are not limited to, insulin.

For example, in some patients with Type I diabetes and in some of the patients with Type II diabetes the Langerhans Islets have been destroyed. In one embodiment, the present invention contemplates restoring biologically active Langerhans Islets in the pancreas of these patients. It is believed that such restoration would thereby provide endogenous insulin and cure the state of diabetes. In one embodiment, α-gal liposomes at a concentration ranging between 0.01 and 500 mg/ml are injected into the pancreas by a device enabling endoscopy ultrasound, or by laparoscopy, or by any other procedure which enables for direct injection of the α-gal liposomes into the pancreas. The interaction between the injected α-gal liposomes and the anti-Gal antibody activates complement and the generated chemotactic complement cleavage peptides recruit monocytes and macrophages to the injection site. The macrophages are activated by Fc/FcγR interaction with anti-Gal coated α-gal liposomes and secrete cytokines and growth factors that recruit stem cells. These stem cells and/or stem cells originating from macrophages proliferate and differentiate into Langerhans Islet cells that form the islets and secrete endogenous insulin.

H. Nerve System

In some embodiments, the methods and compositions of the present invention are used to restore structure and/or function to injured tissues of the central and peripheral nerve system. In one embodiment, the present invention contemplates treating brain tissue that is injured as a result of conditions including, but not limited to, ischemia (i.e., for example, infarct), or trauma. Although it is not necessary to understand the mechanism of an invention, it is believed that injection of α-gal liposomes into the injured brain tissue promotes recruitment and activation of macrophages which transdifferentiate into neurons and/or recruit and activate stem cells. It is also believed that the activated macrophages secrete cytokines and growth factors that may promote repair of the injured brain tissue. α-gal liposomes recruits and induces stem cell migration from adjacent uninjured brain tissue, or from other site in the body, or are the result of transdifferentiation from macrophages to the injured brain tissue. These stem cells are believed to differentiate into brain cells that replace the injured tissue, based on cues from normal brain cells, matrix and microenvironment. Ultimately, α-gal liposomes injection into the injured brain tissue restores partially or completely the structure and function of the treated tissue.

In another embodiment, injection of α-gal liposomes into nerves damaged by physical trauma, or by other types of trauma, or because of nerve degeneration, enhances recruitment of neutrophils, monocytes and macrophages into the injured area of the nerve. The activated macrophages debride the damaged nerve tissue and secrete nerve growth factors that recruit stem cells and induce axonal regeneration and restoration of nerve pulse conductivity via the regenerating nerve. This is contemplated to result in partial or complete restoration of function of the treated nerve.

I. Musculoskeletal

In preferred embodiments the methods and compositions of the present invention are used to restore structure and function injured parts of the musculoskeletal system. In one embodiment the present invention can be used to treat skeletal muscle injured due to physical trauma or to ischemia. Injection of α-gal liposomes into the injured muscle tissue enhances recruitment of neutrophils, monocytes and macrophages into the injured muscle. The recruited macrophages are activated by Fc/FcγR interaction with anti-Gal coated α-gal liposomes and secrete cytokines and growth factors that promote repair of the injured muscle tissue, by recruiting stem cells. A proportion of the macrophages also has the potential of stem cells. The stem cells recruited by macrophages or originating from macrophages differentiate into myoblasts that fuse into myotubes which repair the injured muscle and restore its biological activity.

In a further embodiment, injection of α-gal liposomes into the synovial cavity, or into damaged cartilage in joints enhances recruitment of neutrophils, monocytes and macrophages into the synovial cavity or cartilage ultimately resulting in tissue repair. In particular, macrophages activated by the binding of α-gal liposome/anti-Gal antibody complexes mediate debridement of the damaged cartilage and through secretion of growth factors and cytokines direct migration of stem cells that differentiate into chondroblasts within the damaged cartilage. The chondroblasts in turn secrete collagen and other cartilage matrix proteins, polysaccharides and proteoglycans, resulting in repair and regeneration of the damaged articular or meniscus cartilage within the treated joint. Similarly, macrophages activated by the binding of α-gal liposome/anti-Gal antibody complexes mediate debridement of the damaged bone and through secretion of growth factors and cytokines recruit osteoclasts and osteoblasts into the injection site for repair and regeneration of the damaged bone.

J. Vascular System

In some embodiments, the present invention contemplates compositions and methods for the recruitment of stem cells, resulting in repair and regeneration of the blood vessel wall. For example, α-gal liposomes may be administered to patients with damaged blood vessels or having an anastomoses. In one embodiment, the injured blood vessel may be surrounded by a wound care device containing α-gal liposomes at a concentration ranging between 0.01 and 500 mg/ml. This device can be in the form of a gel, plasma clot or fibrin clot surrounding part or the whole injured blood vessel. Alternatively, a collagen sheet or any biodegradable or non-biodegradable sheet containing the α-gal liposomes or having on its surface α-gal liposomes and which can be shaped into a tube around the injured blood vessel can be used to apply α-gal liposomes around the injured blood vessel. Although it is not necessary to understand the mechanism of an invention, it is believed that the interaction between the injected α-gal liposomes and the anti-Gal antibody activates complement and the generated chemotactic complement cleavage peptides recruit monocytes and macrophages to the injection site. The macrophages are activated by Fc/FcγR interaction with anti-Gal coated α-gal liposomes and secrete cytokines and growth factors that promote the repair of the injured blood vessel wall. These secreted cytokines and growth factors also recruit stem cells that proliferate and differentiate into cells that enable the regeneration of the intact blood vessel wall. Some of the recruited macrophages, which have stem cell potential, also may trans-differentiate into cells that repair the injured blood vessel.

K. Gastrointestinal System

In one embodiment, the present invention contemplates compositions and methods for recruiting stem cells, resulting in repair and regeneration of the gastrointestinal wall. In one embodiment, the patient comprises an ulcer and/or other injuries to the gastrointestinal tract. The treatment methods described herein are applicable to any damage to the wall at any part of the gastrointestinal tract. In one embodiment, an injured gastrointestinal area may be injected with α-gal liposomes at a concentration ranging between 0.01 and 500 mg/ml. Although it is not necessary to understand the mechanism of an invention, it is believed that the interaction between the injected α-gal liposomes and the anti-Gal antibody activates complement and the generated chemotactic complement cleavage peptides recruit monocytes and macrophages to the injection site. The macrophages are activated by Fc/FcγR interaction with anti-Gal coated α-gal liposomes and secrete cytokines and growth factors that recruit stem cells and promote the repair of the injured tissue. The recruited stem cells proliferate and differentiate into cells that replace the injured cells and repair the damaged gastrointestinal wall at the injection site.

L. Epidermal Wound Healing

1. In Vitro Interaction of Anti-Gal Coated α-Gal Liposomes with KO Mouse Macrophages Induces VEGF Secretion α-gal liposomes were generated using rabbit red blood cells (RBC) that provide multiple glycolipids with α-gal epitopes (i.e., for example, α-gal glycolipids). As previously shown, incubation of rabbit RBC membranes with chloroform and methanol results in extraction of phospholipids, cholesterol and multiple α-gal glycolipids. Galili et al., 2007 "Intratumoral injection of α-gal glycolipids induces xenograft-like destruction and conversion of lesions into endogenous vaccines" *J. Immunol.* 178:4676-4687. Rabbit RBC have the highest concentration of α-gal glycolipids among mammals, ranging in size from 5 to 40 carbohydrates, and having one, two or multiple branches, each capped with an α-gal epitope. Sonication in saline of the dried organic extract from rabbit RBC membranes results in formation of liposomes constructed of a membrane of phospholipids and cholesterol and multiple α-gal glycolipids anchored in that membrane. Because of the multitude of α-gal epitopes on these liposomes (i.e., for example, $\sim 10^{15}$ α-gal epitopes/mg liposomes), they have been designated α-gal liposomes and were found to interact effectively with anti-Gal produced by KO mice. Abdel-Motal et al., 2009 "Mechanism for increased immunogenicity of vaccines that form in vivo immune complexes with the natural anti-Gal antibody" *Vaccine* 27:3072-3082; and Galili et al., 2010 "Accelerated healing of skin burns by anti-Gal/α-gal liposomes interaction" *Burns* 36:239-251.

Figure 15:
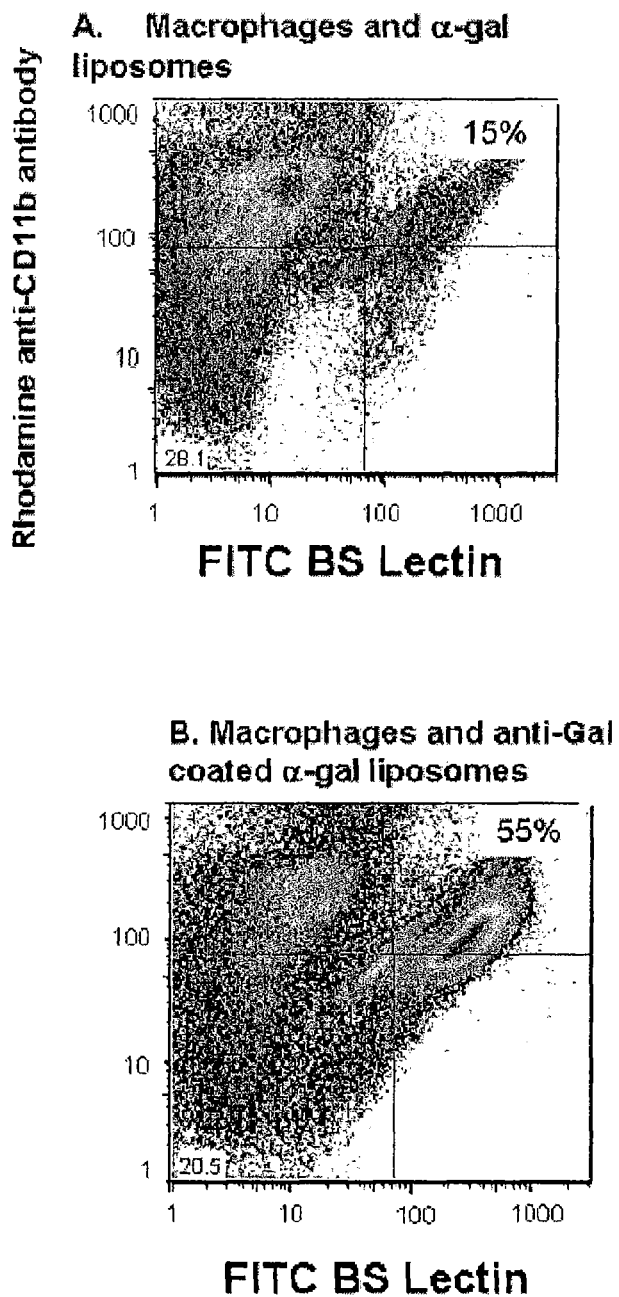
FIG. 15. Exemplary binding of anti-Gal antibody coated α-gal liposomes to macrophages induces macrophage activation.
Figure 15:
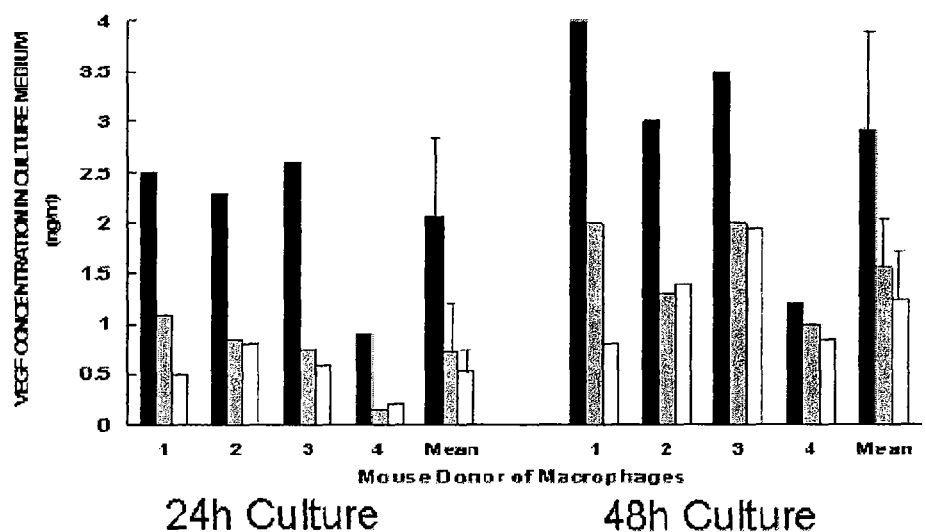

The ability of anti-Gal/α-gal liposomes to interact with and activate KO mouse macrophages was determined. Such activation was documented by measuring VEGF secretion. For these experiments, α-gal liposomes pre-coated with KO mouse anti-Gal antibodies were incubated with KO mouse peritoneal macrophages. Non-antibody coated α-gal liposomes incubated with macrophages served as controls. Liposome binding to the macrophages was determined by flow cytometry following double staining of fluorescein (green) coupled *Bandeiraea simplicifolia* IB4 lectin (BS lectin-binding specifically to α-gal epitopes and rhodamine (red) coupled anti-CD11b Ab (specific for macrophages). Galili et al., 1985 "Human natural anti-α-galactosyl IgG. II. The specific recognition of α(1-3)-linked galactose residues" *J. Exp. Med.* 162:573-82; and Galili et al., 1987 "Evolutionary relationship between the anti-Gal antibody and the Galα1-3Gal epitope in primates" *Proc. Natl. Acad. Sci.* (USA) 84:1369-1373. Non-antibody coated α-gal liposomes adhered to ~15% of the KO mouse macrophages. See, FIG. 15A. However, binding increased by ~4-fold when the liposomes were coated with anti-Gal antibody (55%). See, FIG. 15B.

These data are similar to those observed using a system in which tumor cells coated with mouse or human anti-Gal antibodies bound to macrophages via Fc/FcγR interaction. LaTemple et al., 1999 "Increased immunogenicity of tumor vaccines complexed with anti-Gal: Studies in knockout mice for α1,3galactosyltranferase" *Cancer Res.* 59:3417-3423; and Manches et al., 2005 "Anti-Gal mediated targeting of human B lymphoma cells to antigen-presenting cells: a potential method for immunotherapy with autologous tumor cells" *Haematologica* 90:625-634.

VEGF secretion was quantified in peritoneal macrophage cultures co-cultured with anti-Gal coated or non-antibody coated α-gal liposomes to determine whether macrophages were activated by the anti-Gal/α-gal liposome complexes. Macrophages co-cultured with anti-Gal coated α-gal liposomes produced 2-4 fold more VEGF than the same macrophages incubated with α-gal liposomes lacking anti-Gal antibody. See, FIG. 15C. The latter macrophages produced low levels of VEGF similar to that secreted by macrophages cultured in the absence of liposomes. These findings support the assumption that interaction between the Fc portion of anti-Gal antibody bound to α-gal liposomes and FcγR on macrophages activates these cells to produce and secrete tissue healing cytokines.

2. Recruitment of Macrophages into Skin Sites Injected with α-Gal Liposomes

Studies on the in vivo interactions between anti-Gal antibodies with α-gal liposomes require animal models that lack self expressed α-gal epitopes and can generate anti-Gal antibodies. A mouse model that lacks α-gal epitopes is the α1,3galactosyltransferase (α1,3GT) knockout mouse (KO mice). Thall et al., 1995 "Oocyte Gal α1,3Gal epitopes implicated in sperm adhesion to the zona pellucida glycoprotein ZP3 are not required for fertilization in the mouse" *J. Biol. Chem.* 270:21437-21440. These mice produce anti-Gal antibodies in titers comparable to those attained in humans following immunization with pig kidney membranes (PKM). Anti-Gal produced in the immunized mice displays characteristics (i.e., for example, classes and subclasses) similar to human anti-Gal antibodies. Abdel-Motal et al., 2006 "Increased immunogenicity of HIV gp120 engineered to express α-gal epitopes" *J. Virol.* 80:6943-6951.

Figure 16:
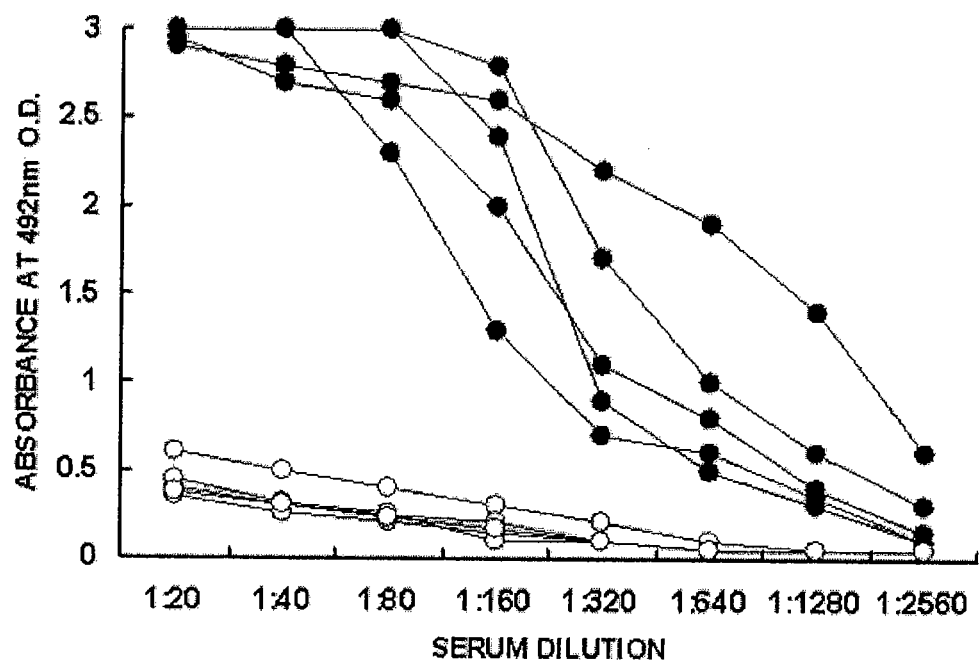
FIG. 16 presents exemplary data showing binding of anti-Gal IgG in KO mouse serum to α-gal liposomes (●), or to KO pig liposomes (○) coating ELISA wells. Each curve represents serum from an individual mouse. The same sera were studied for IgG binding to both types of liposomes.

The effect of anti-Gal/α-gal liposome interaction on localized recruitment of macrophages was studied in vivo in anti-Gal antibody producing KO mice injected subcutaneously with 10 mg α-gal liposomes in 0.1 ml saline. Control liposomes were generated using KO pig RBC that lack α-gal epitopes due to targeted disruption of the α1,3GT gene in these knockout pigs. Byrne et al., 2008 "Proteomic identification of non-Gal antibody targets after pig-to-primate cardiac xenotransplantation" *Xenotransplantation* 15:268-276. As with KO mice, αGT KO pigs completely lack α-gal glycolipids, therefore liposomes produced from their RBC membranes completely lack α-gal epitopes. Because KO pig liposomes lack α-gal epitope they do not bind IgG antibodies in KO mouse serum, as indicated in ELISA wells coated with KO pig liposomes. See, FIG. 16. The marginal binding of IgG antibodies at the lowest dilutions is likely to be nonspecific binding of serum IgG to the ELISA wells. In contrast, anti-Gal in these sera readily binds to α-gal liposomes coating ELISA wells. This binding is detectable (>1.0 O.D.) even at serum dilutions of 1:160, whereas no such binding was observed at the lowest dilution (1:20) in wells coated with aGT KO pig liposomes. Previous studies by flow cytometry demonstrated a similar interaction of anti-Gal IgG and IgM antibodies with α-gal liposomes incubated in KO mouse serum. Galili et al., 2010 "Accelerated healing of skin burns by anti-Gal/α-gal liposomes interaction" *Burns* 36:239-251.

Figure 17:
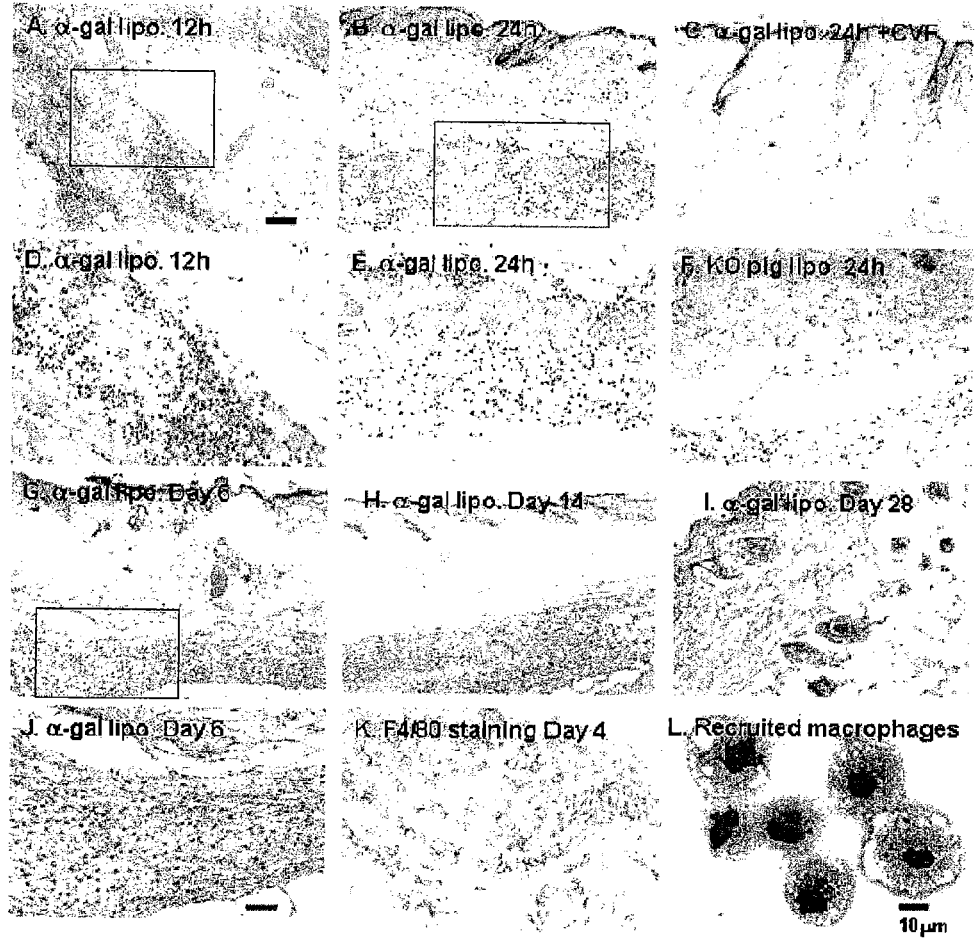
FIG. 17 presents exemplary photomicrographs of in vivo recruitment of cells following subcutaneous injection of 10 mg α-gal liposomes in KO mouse skin. Specimens stained with hematoxylin and eosin (H&E). For the purpose of orientation, the epidermis is shown in the upper areas of FIGS. 17B, 17C, 17G, 17H and 17H. Each figure is representative of 5 mice/group.
Figure 18:
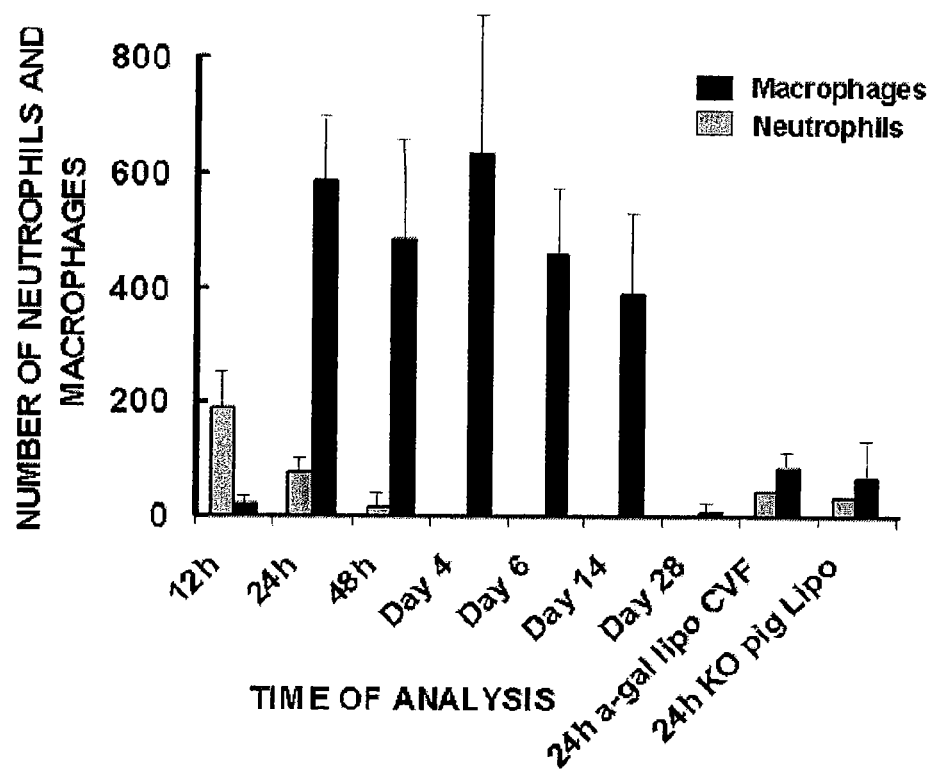
FIG. 18 presents exemplary data showing the recruitment of neutrophils (grey columns) and macrophages (closed columns) by 10 mg liposomes injected subcutaneously in 0.1 ml suspension into KO mice. α-gal lipo CVF-α-gal liposomes were co-injected with 20 μg cobra venom factor (inhibits complement activity). "KO pig lipo" are liposomes produced from α1,3GT knockout pig red blood cells (liposomes that lack α-gal epitopes). Number of infiltrating cells was determined in histological sections by counting cells within a rectangular area marked in a microscope lens at magnification of ×400, corresponding to 100×200 μm area. The differences in number of macrophages in day 1 (24 h) to day 14 are not significant. Mean+SD from 5 mice/group.

Skin specimens were obtained from euthanized mice at various time points after subcutaneous injection of 10 mg α-gal liposomes were fixed and stained with hematoxylin and eosin (H&E). Injection sites where liposomes were dissolved by ethanol and removed during the staining process are visualized a "empty" areas. See, FIGS. 17A, 17C, 17F, and 17G. The data demonstrate that within 12 h, the injection site in the hypodermis was surrounded by neutrophils. See, FIGS. 17A and 17D. Most of the neutrophils disappeared by 24 h and were subsequently replaced by infiltrating macrophages. See, FIGS. 17B, 17E, and FIG. 18. These cells were confirmed to be macrophages using F4/80 antibody, which specifically binds to macrophages. See, FIG. 17K. Macrophage recruitment appears to be highly dependent on activation of the complement cascade, as low macrophage recruitment was observed 24 h after co-injection of α-gal liposomes and cobra venom factor (CVF-20 μg), which inhibits complement activation. See, FIG. 17C and FIG. 18. The significance of α-gal epitope expression on liposomes for induction of rapid recruitment of macrophages through complement activation is further strengthened by failure of 10 mg KO pig liposomes to induce recruitment within 24 h post injection. See, FIG. 17F and FIG. 18.

Inspection of α-gal liposome injection sites after 4 and 6 days revealed a gradual increase in the size of macrophages and the formation of large clusters of these cells with almost no intercellular space. See, FIGS. 17K and 17J, respectively. Individual macrophages inspected after 6 days were very large (20-30m) and contained multiple vacuoles that represented the internalized α-gal liposomes. See, FIG. 17L. This morphology of infiltrating macrophages was observed up to 14 days post injection. See, FIG. 17H. However, by 3-4 weeks, all macrophages have disappeared and the injected skin displayed normal histology. See, FIG. 17I and FIG. 18. Parallel studies in mice injected subcutaneously with saline did not show evidence of recruitment of cells into the injection site at any time point (data not shown).

Figure 19:
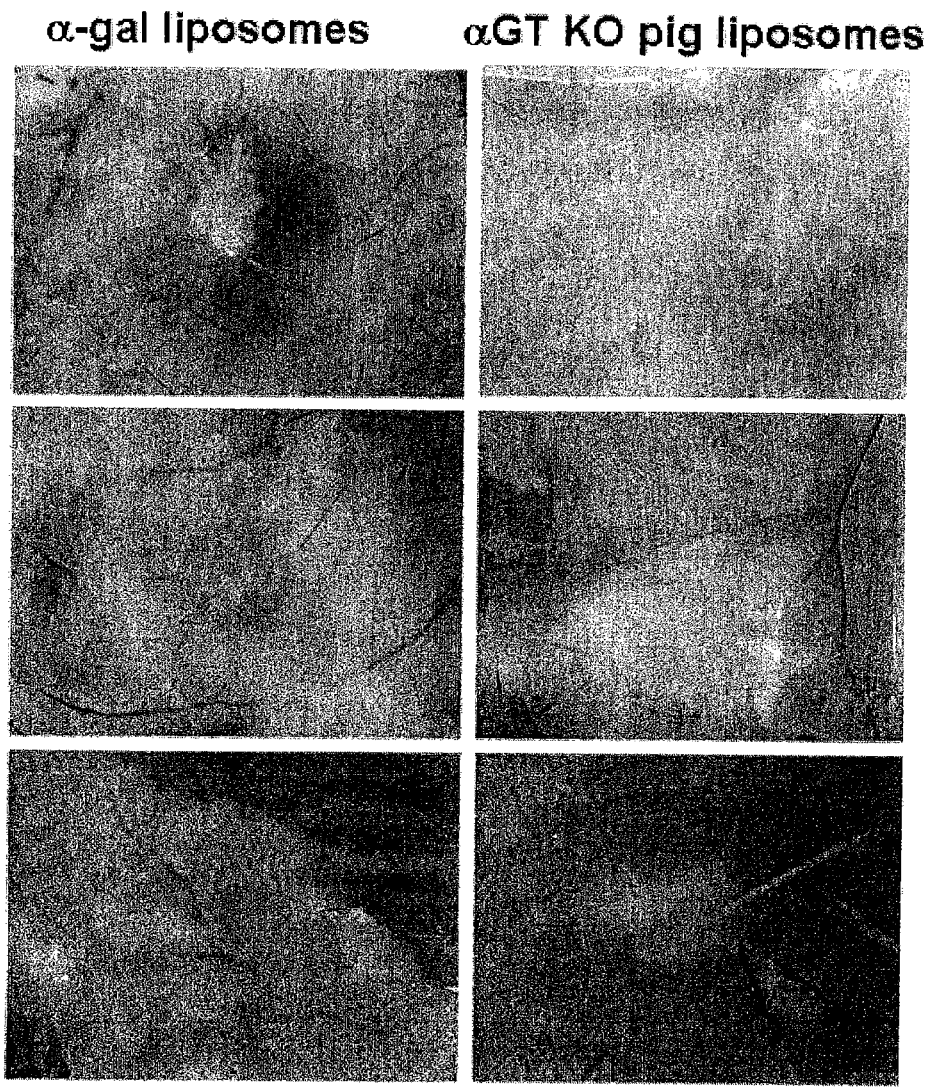
FIG. 19 presents exemplary photomicrographs showing redness adjacent to subcutaneous injection sites of α-gal liposomes (left column), or KO pig liposome (right column) in KO mice, viewed 48 h post injection (×4). The injected liposomes appear as white areas viewed from the basal side of the skin. Note the redness caused by vasodilation and/or angiogenesis near the α-gal liposome injected areas, but not by the KO pig liposome injected areas.

Subcutaneous injection of anti-Gal/α-gal liposomes resulted in changes in gross morphology shortly after the injection, as viewed from the hypodermis side of the skin. Two days post injection, redness was observed around the site of α-gal liposome injection, whereas no such redness was observed in injection sites of KO pig liposomes. See, FIG. 19. Subcutaneous injection of saline resulted in no induction of local redness (data not shown). Although it is not necessary to understand the mechanism of an invention, it is believed that the redness observed following α-gal liposome injection may be associated with local vasodilation of capillaries induced by complement cleavage products generated following anti-Gal/α-gal liposome interaction. It is also believed that some of the "redness" was due to angiogenesis and sprouting of new capillaries as a result of local secretion of VEGF by activated macrophages.

3. In Vivo Induction of Cytokine Gene Expression by Injected α-Gal Liposomes

The above in vitro studies showing that macrophages that interact with α-gal liposomes suggested that these cells might be activated following the Fc/FcγR interaction with anti-Gal antibody coating these liposomes. Macrophages migrating into an injection site of α-gal liposomes were assayed to determine if genes encoding cytokines that promote wound healing were being activated. To test this, KO mice were injected subcutaneously with 10 mg α-gal liposomes or with saline as control. After 48 h, the skin at the injection site was harvested, RNA extracted, mRNA was isolated and cDNA was synthesized and subjected to quantitative real time PCR (q-RT-PCR) with primers specific for 11 cytokine genes known to be produced by activated macrophages. GADPH was used as a control housekeeping gene for normalizing the cDNA. Gene expression in α-gal liposome injected KO mouse skin was calculated and expressed as relative fold change in comparison to saline injected skin specimens normalized to GAPDH expression.

Figure 20:
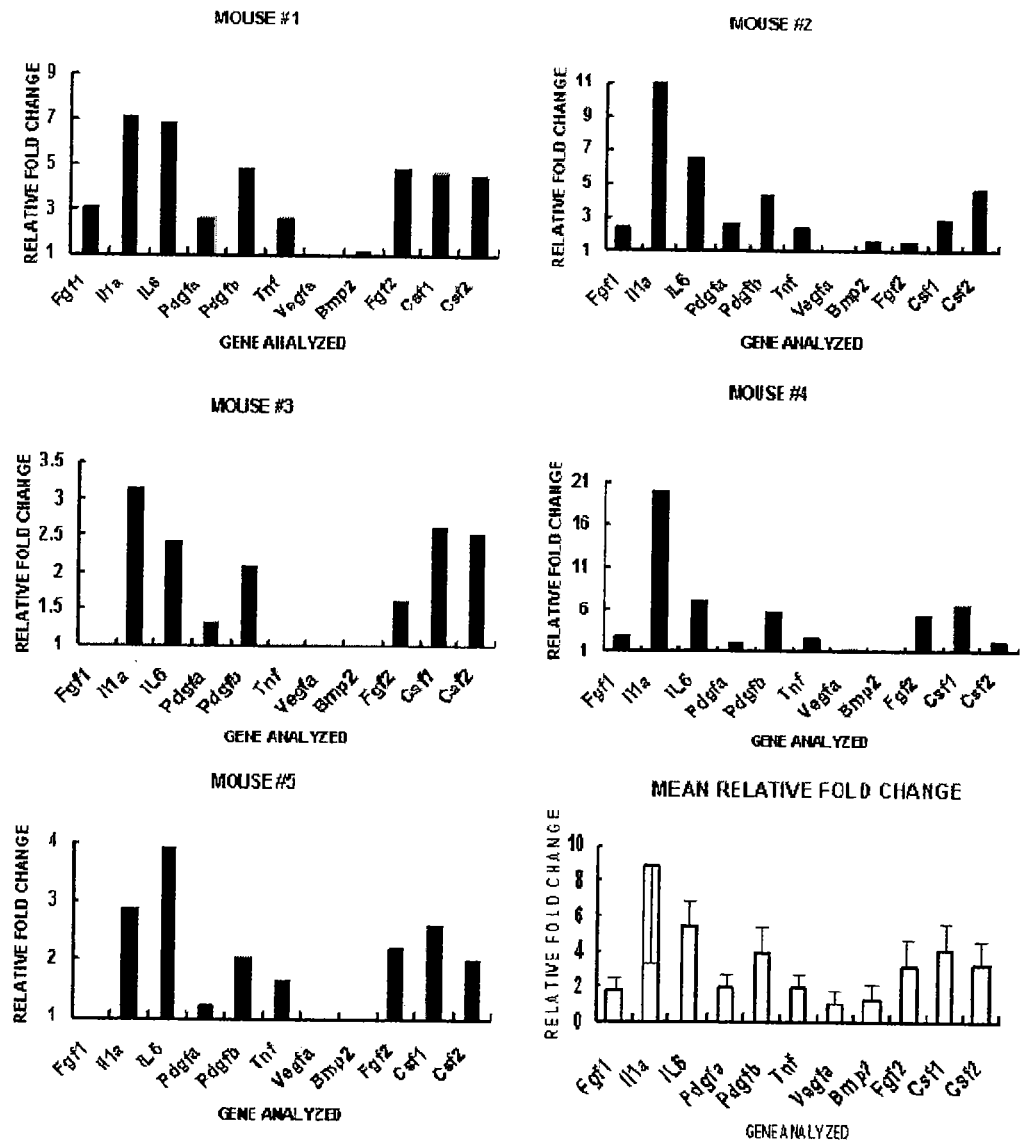
FIG. 20 presents exemplary data showing the activation of cytokine gene expression in macrophages as measured by quantitative real time polymerase chain reaction (q-RT-PCR) as fold-changes in expression of the various cytokine genes. RNA extracts were taken from 5 KO mice injected in the skin with α-gal liposomes and harvested after 48 h, compared to saline injected skin as control. The bottom right figure represents the Mean+SD, except for Il1a where the mean−SD is presented.

Although there was a mouse to mouse variation, in the five skin specimens tested, six of the assayed genes: Il1a, IL6, Pdgfb, Fgf2 Csf1 and CsJ2 displayed >3 fold increase in expression compared to controls. Activation of these wound healing promoting cytokines genes was observed in mice injected with α-gal liposomes. See, FIG. 20. These data coincide with the observed extensive recruitment of macrophages into the injection site. See, FIG. 18. These data strongly suggest that these activated genes are expressed in macrophages recruited by anti-Gal/α-gal liposome interaction.

Figure 21:
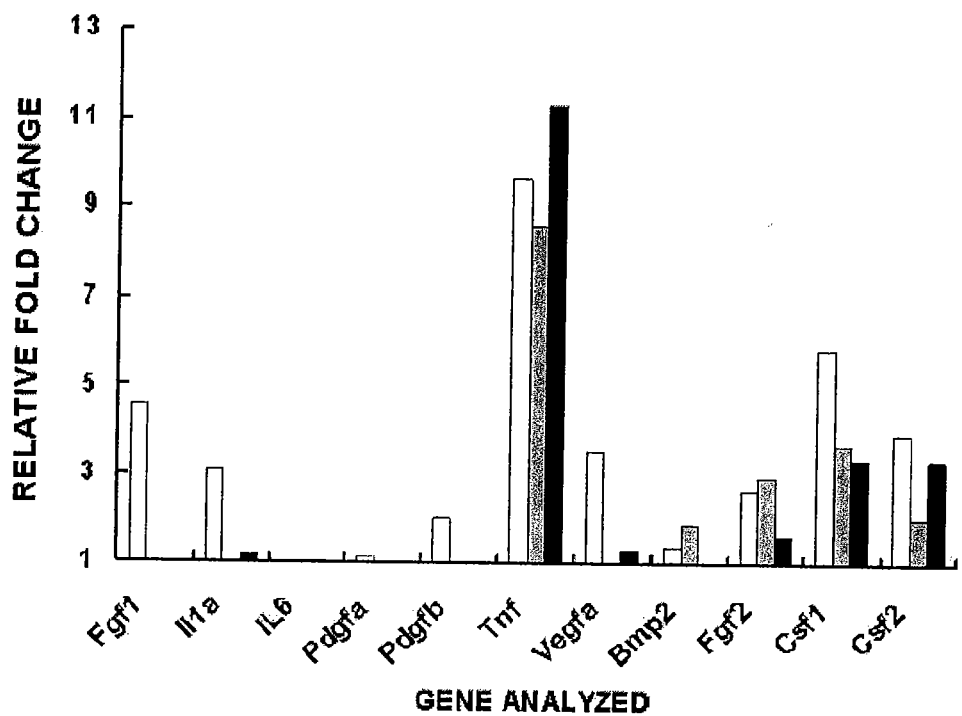
FIG. 21 presents exemplary data showing the activation of cytokine gene expression in macrophages as measured by q-RT-PCR as fold changes in cytokine gene expression. Peritoneal macrophages were harvested 24 h post i.p. injection of 30 mg α-gal liposomes and compared to peritoneal macrophages from saline injected KO mice as a control.

In vivo activation of macrophage cytokine genes was further studied in a relatively pure macrophage population interacting with α-gal liposomes. Macrophages were recruited to the peritoneal cavity of KO mice 5 days post i.p. injection of thioglycolate. These mice were then injected i.p. with 30 mg α-gal liposomes. Control mice were injected with saline instead of α-gal liposomes (3 mice/group). After 24 h, the macrophages were harvested, their RNA extracted and subjected to q-RT-PCR to test for cytokine gene expression. Similar to the observations in activated skin macrophages, peritoneal macrophages activated by anti-Gal/α-gal liposome immune complexes increased expression of the Csf1 and Csf2 genes. See, FIG. 21. However, the most activated gene in all 3 mice, 24 h post injection, was the Tnf gene that displayed 9-11 fold amplification. Since this gene did not display a significant increased expression in skin macrophages assayed at 48 h post injection. These findings suggest that expression of cytokine genes may be altered in various time points.

4. α-gal Liposome Treatment Accelerates Epidermal Healing of Skin Wounds

The above observations on accelerated recruitment of macrophages and activation of these cells following ant-Gal/α-gal liposome interaction suggested that topical application of these liposomes on wounds might induce accelerated healing. To test this, anesthetized KO mice were given excisional skin wounds (~3×6 mm oval excision) in which epidermis, dermis and upper part of the hypodermis were removed from the abdominal flank. The wounds were treated with 10 mg α-gal liposomes, KO pig liposomes (lacking α-gal epitopes), or saline on a 10×10 mm pad of spot bandages used as wound dressing. The gross appearance of the wound was documented on various days and the wound area removed from euthanized mice and subjected to histological analysis. Wound healing was determined by the percent of wound surface covered by regenerating epidermis.

Figure 22:
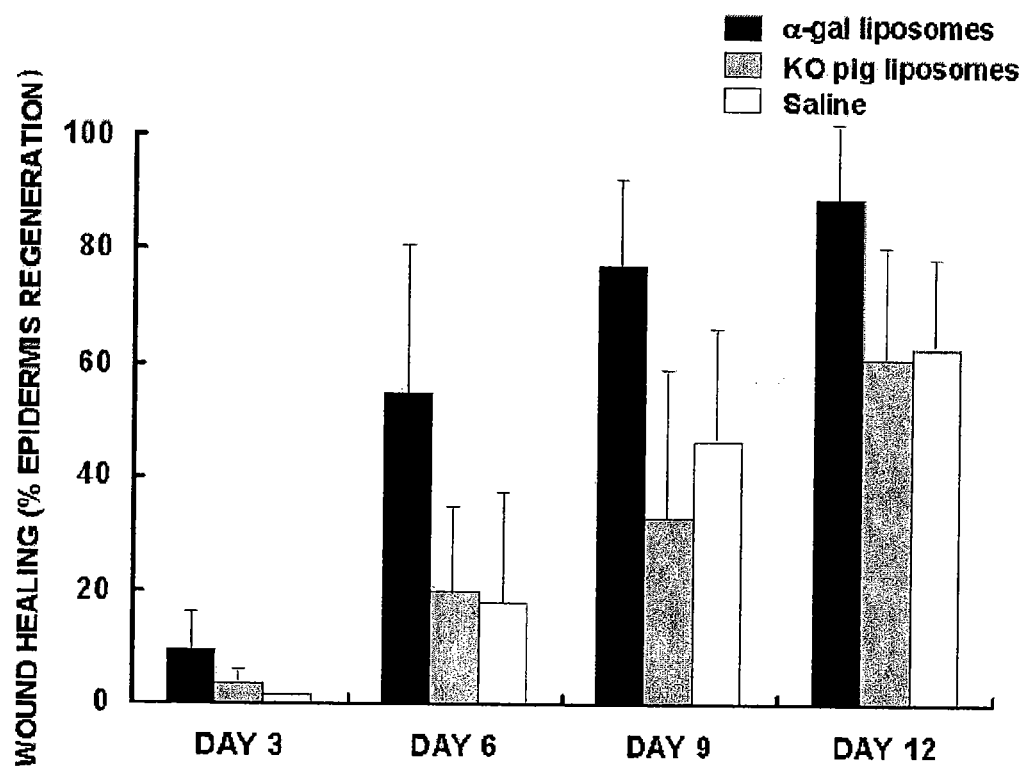
FIG. 22 presents exemplary wound healing data taken at different time points after epidermal excisional wound formation and topical application of a dressing covered with either: i) 10 mg α-gal liposomes (closed columns); ii) 10 mg KO pig liposomes lacking α-gal epitopes (grey columns); or iii) saline (open columns). Extent of wound healing is described as % of the wound area covered with regenerating epidermis. Data presented as Mean+SD from >5 mice/group ($p<0.05$). On day 6, n=20 for mice with wounds treated with α-gal liposomes or with saline.
Figure 23:
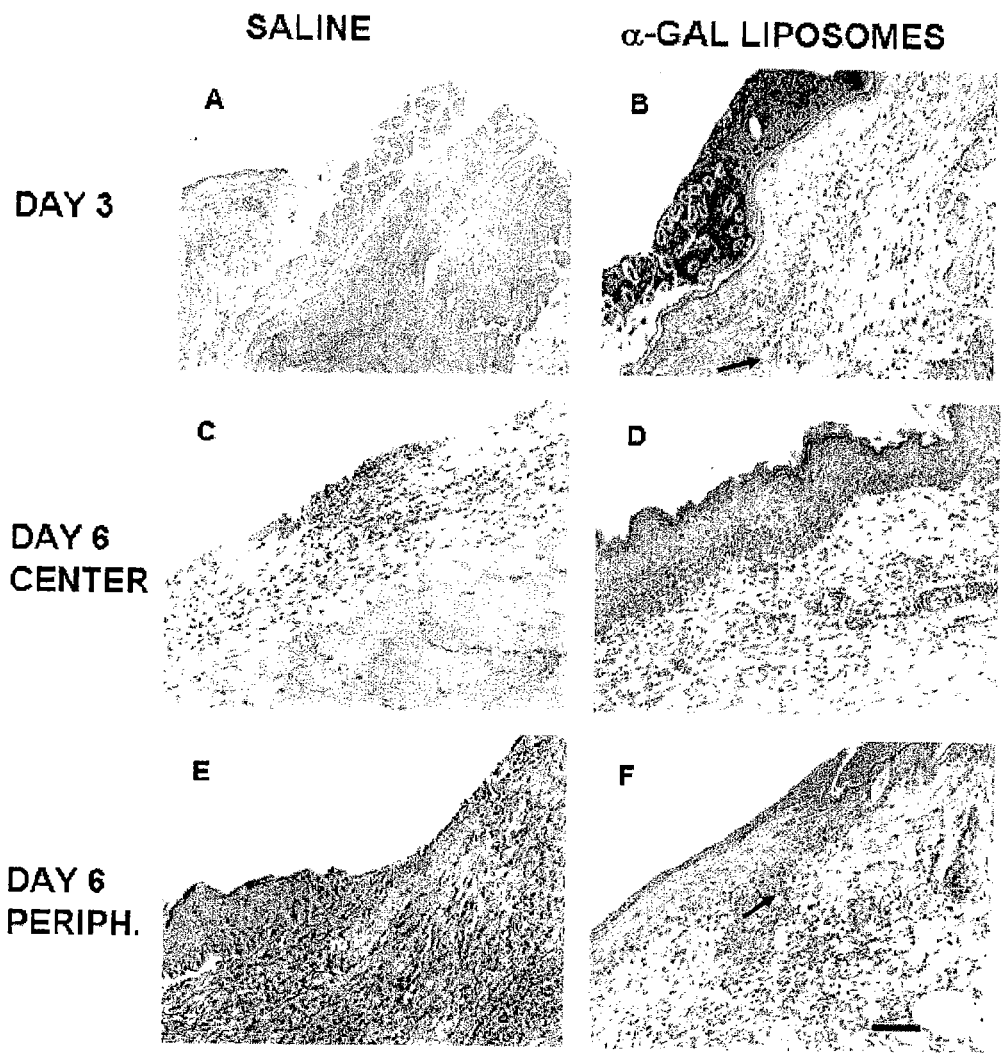
FIG. 23 presents exemplary micrographs showing healing of representative excisional wounds treated with spot bandages covered with 10 mg α-gal liposomes, or with saline (hematoxylin and eosin [H&E]). Specimens are representative of 7 mice treated with α-gal liposome (complete wound closure) and of 20 mice treated with saline.

The data was evaluated by histological analysis and by gross appearance on day 6 in specific cohorts of mice. Control wounds treated for 3 days with bandages that had saline displayed no evidence of regeneration of the epidermis and no significant infiltration of macrophages into the wound. See, FIGS. 22 and 23A, respectively. In contrast, wounds treated with α-gal liposomes for 3 days displayed extensive infiltration of mononuclear cells with macrophage morphology and which form a characteristic granulation tissue. See, FIG. 23B. These α-gal liposome treated wounds also exhibited a distinct initiation of epidermis regeneration, as indicated by the multilayered large epidermal cells observed over the newly formed dermis at border of the injured area. See, FIG. 22 and FIG. 23B. The regenerating epidermis covered, on average, 15% of the wound, whereas control wounds treated with KO pig liposomes or with saline displayed only a residual epidermis regeneration. See, FIG. 22.

By day 6, control saline treated wounds displayed extensive infiltration of macrophages into the regenerating dermis and initial regeneration of the epidermis See, FIGS. 23C and 23E, respectively. However, at this time point, the regeneration of the epidermis is observed only at the periphery of the wound, whereas at the center of the wound, the dermis remains exposed. See, FIG. 23C. The leading edge of the regenerating epidermis on day 6, in saline treated wounds is shown. See, FIG. 23E.

Figure 24:
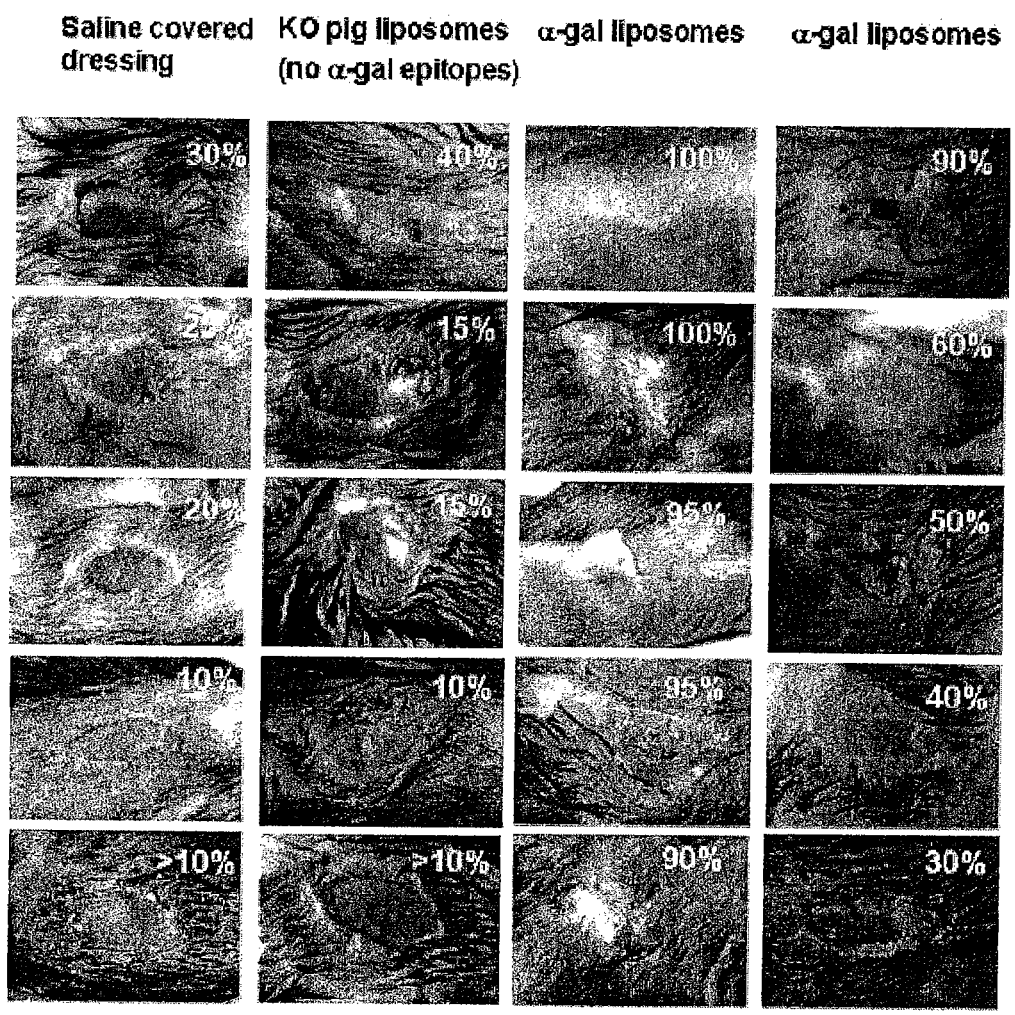
FIG. 24 presents exemplary micrographs showing the gross appearance of day 6 excisional wounds treated with dressing (spot bandages) covered with: saline (First Column: wounds); KO pig liposomes (Second Column: 5 wounds); or α-gal liposomes (Third and Fourth Columns: 10 wounds). The extent of wound healing is evaluated by the estimated proportion (%) of the wound covered with regenerating epidermis (i.e., % of healing) is indicated within each figure. ×2-4.

In wounds treated for 6 days with saline or with KO pig liposomes, the regenerating epidermis covers only ~20% of the wound surface. In contrast, the extent of epidermis regeneration in wounds treated with α-gal liposomes was much higher on day 6 and reached an average of ~60% of the wound surface. See, FIG. 22 and FIG. 23. Further, on day 6~35% of mice treated with α-gal liposomes displayed complete closure of the wound by regenerating epidermis. See, FIG. 23 and FIG. 24. In the other 65% of the mice, the regenerating epidermis covered ~30-80% of the wound. The data show that α-gal liposome regenerated epidermis is thicker than endogenous epidermis (4-8 layers of epithelial cells vs. 2 layers, respectively), suggesting a highly proliferative state of epidermal cells. See, FIGS. 23D and 23F. Also, in many α-gal liposome treated wounds examined on day 6 the dermis was thicker than that in saline treated wounds, suggesting accelerated regeneration of the dermis. Compare, FIG. 23D with 23C. By day 9, only ~40% of the surface of saline or aGT KO pig liposome treated wounds was covered by regenerating epidermis. In comparison, most of α-gal liposome treated wounds showed complete epidermal closure with some displaying between approximately 60-90% regeneration. See, FIG. 24.

After 12 days of treatment, on average, ~60% of wound surface in saline and KO pig liposome treated wounds were covered by the regenerating epidermis whereas most of the α-gal liposome treated wounds were completely covered by epidermis. Overall, the regeneration of epidermis in wounds treated with α-gal liposomes is approximately twice as fast as the physiologic regeneration of saline treated wounds. The similar rate of epidermis regeneration between saline treated and KO pig liposome treated wounds strongly suggests that accelerated regeneration in these studies is dependent on α-gal epitope presentation on the liposomes.

5. Regeneration of Dermis in Wounds as Evaluated by Trichrome Staining

Figure 25:
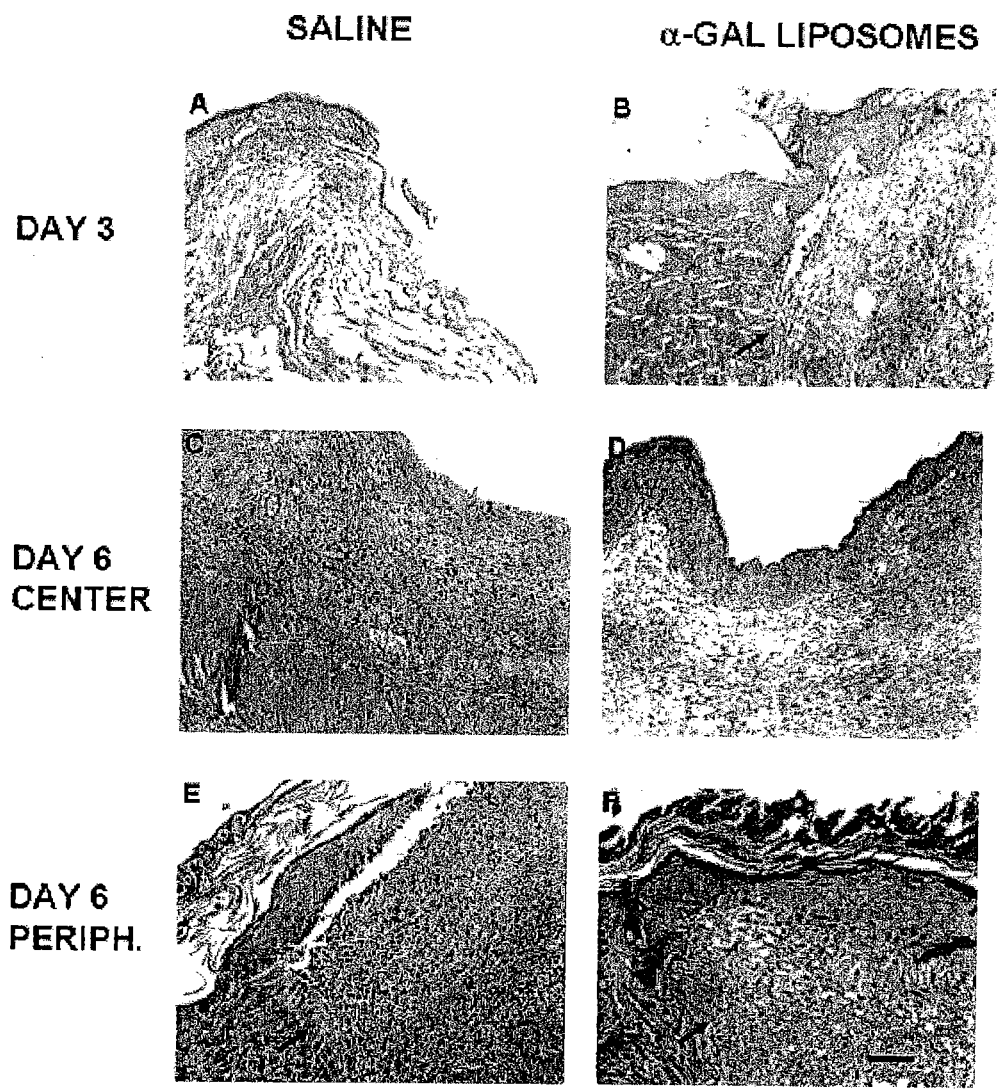
FIG. 25 presents exemplary photomicrographs showing Trichrome staining of regenerating dermis in the skin wounds treated with dressing (spot bandages) covered with saline (A, C and E) or with α-gal liposomes (B, D and F), as detailed in FIG. 22. In this staining, collagen is blue and the various cells are purple. The border of the wound bed between uninjured and regenerating tissues is marked with arrows in 25B, 25E and 25F. Magnification in 25A is ×100, in 25B-F ×200. Scale bar in 25F is 50 µm. Specimens are representative of 7 mice treated with α-gal liposome (complete wound closure) and of 20 mice treated with saline.
Figure 26:
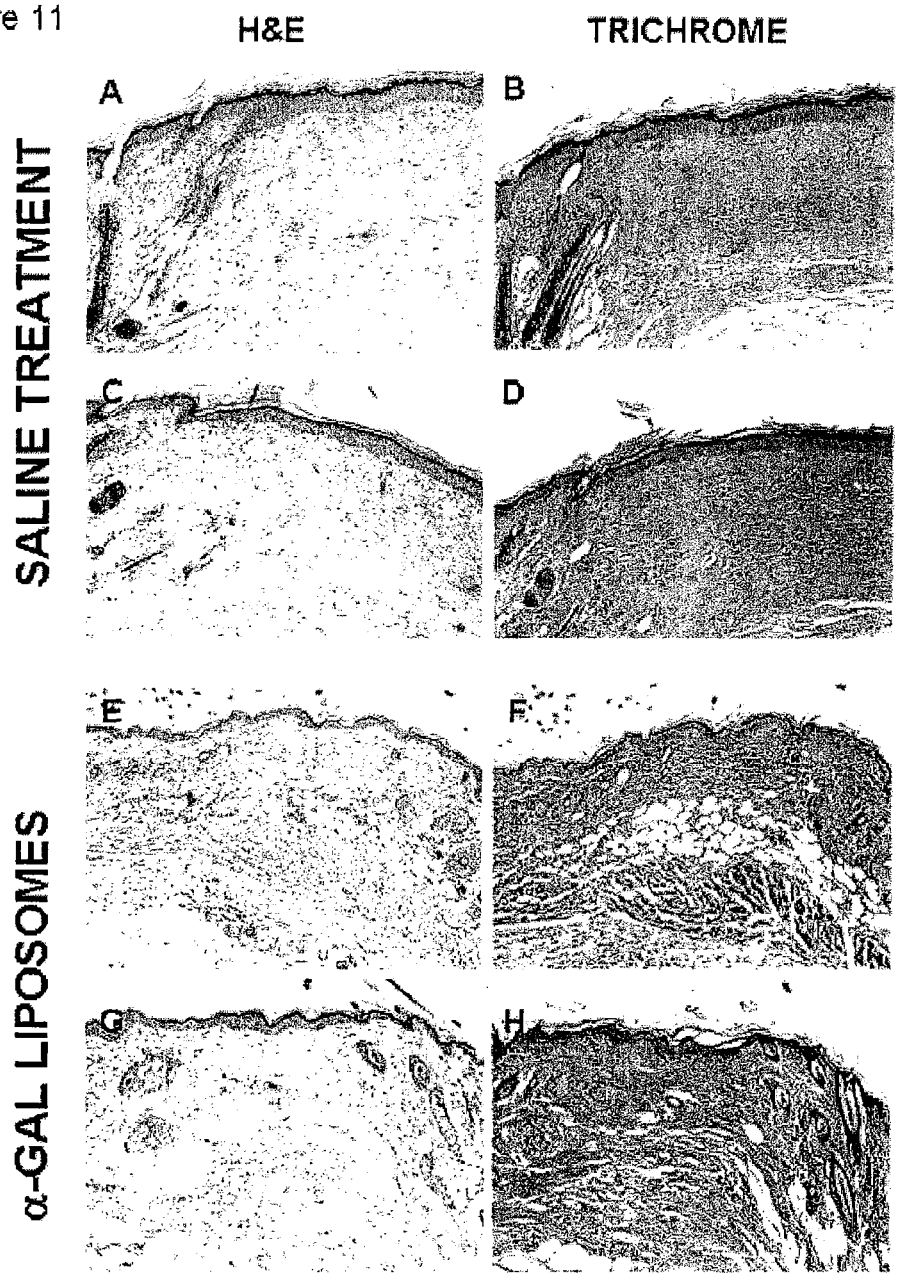
FIG. 26 presents exemplary photomicrographs showing that α-gal liposome treatment decreases scar formation. H&E—(A, C, E and G) and Trichrome staining—(collagen stained blue in B, D, F and H) of wounds treated for 28 days with saline or with α-gal liposomes, as indicated. Saline treated wounds develop a scar characterized by dense connective tissue due to multiple fibroblasts (the two specimens in A, B and C, D) and no skin appendages such as hair and sebaceous glands. In contrast, α-gal liposomes treated wounds (the two specimens in E, F and G, H) display restoration of normal skin histology, including thin epidermis, loose connective tissue in the dermis and appearance of hair and sebaceous glands, as well as fat cells in the hypodermis. Scale bar in C is 100 µm (×100). Specimens are representative of 5 mice/group.

Evaluation of connective tissue (i.e. dermis and hypodermis) regeneration in the wound can be performed following Trichrome staining. Trichrome stains the collagen fibers of the connective tissue within the dermis and hypodermis blue whereas epidermal and dermal residing cells are stained purple. α-gal liposomes treated wounds display regenerating dermis within 3 days post wounding. See, FIG. 25B. In contrast, no evidence for regeneration is observed in the saline treated wounds. See, FIG. 25A. Connective tissue of the dermis and hypodermis of the control wound is loose likely due to the lack of regeneration and/or fluid accumulation following injury. In the α-gal liposome treated wounds, initiation of dermal recovery is evidenced by the collagen fibers appearing beneath the regenerating epidermis. See, FIG. 25B. The uninjured dermis surrounding the wound is characterized by blue staining of collagen that is much denser than the newly formed collagen in the regenerating dermis. The presented histology suggests that collagen secreting fibroblasts are among the first cells recruited within 72 h post injury into wounds treated with α-gal liposomes.

Day 6, control wounds show newly formed dermis that contains multiple macrophages. See, FIGS. 25C and 25E. A distinct border between the newly formed dermis and the uninjured dermis in day 6 control wounds is present. Newly formed dermis filled with many cells is also observed in wounds treated with α-gal liposomes on day 6. See, FIGS. 25D and 25F. Some of the cells residing in the regenerating dermis are fibroblasts depositing collagen. Many of the other cells forming the granulation tissue in this dermis are likely macrophages that have been recruited into the wound.

6. α-gal Liposome Treatment Reduces Scar Formation

Accelerated healing of wounds by α-gal liposomes could result in hyperplasia of the epidermis and/or scar formation in the dermis. To investigate this, wounds were treated for one month with saline or an α-gal liposome dressing (5 mice/ group). Control wounds treated for one month with saline coated bandages displayed wide areas of dense dermis devoid of skin appendages, characteristic of scar formation. In addition, the regenerating epidermis in these control wounds is thicker than normal epidermis and has >5 layers of cells. See, FIGS. 26A-D. This scar formation is the physiologic default mechanism for filling the injured area with dense connective tissue and with epidermis that is thicker than in uninjured skin.

In contrast, epidermis in α-gal liposome treated wounds group displayed normal thickness of 2 cell layers and the density of collagen in the dermis based on Trichrome staining is normal. See, FIGS. 26E-H. Much of the healed wounds treated with α-gal liposomes also contained regenerating appendages such as hair follicles and sebaceous glands. It is notable that wounds treated with α-gal liposomes or with saline contain no granulomas at one month and that most macrophages have disappeared from the wound site.

V. Wound Care Devices

In some embodiments, the invention relates to the use of α-gal liposomes in wound care devices for aged subjects in order to induce effective wound healing by local activation of complement as a result of anti-Gal antibody binding to α-gal lipososmes. In still another embodiment, the invention relates to the use of α-gal liposomes in wound care devices applied to a wound in a subject following trauma. While not limiting the scope of the present invention, one example of a use for the present invention is the treatment of a subject recovering from a car accident resulting in injuries to said subject.

In one embodiment, a wound care device comprises an injury care device selected from the group consisting of syringes, adhesive bands, compression bandages, sponges, gels, semi-permeable films, plasma clots, fibrin clots. In one embodiment, the device comprises physiological compositions including, but not limited to, solutions, suspensions, emulsions, creams, ointments, aerosol sprays, collagen containing substances, stabilizers, drops, matrix-forming substances, foams and/or dried preparation.

VI. Pharmaceutical Compositions

The present invention further contemplates pharmaceutical compositions capable of: i) delivering α-gal epitopes; or ii) administering compositions that interact with α-gal epitopes. The pharmaceutical compositions of the present invention may be administered in a number of ways depending upon whether local or systemic treatment is desired and upon the area to be treated. Administration may be topical, pulmonary (e.g., by inhalation or insufflation of powders or aerosols, including by nebulizer; intratracheal, intranasal, epidermal and transdermal), oral, and/or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 µg to 100 g per kg of body weight, once or more daily, to once every 20 years.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: kDa (kilodalton); rec. (recombinant); N (normal); M (molar); mM (millimolar); µM (micromolar); mol (moles); mmol (millimoles); µmol (micromoles); nmol (nanomoles); pmol (picomoles); g (grams); mg (milligrams); ps (micrograms); ng (nanograms); l or L (liters); ml (milliliters); µl (microliters); cm (centimeters); mm (millimeters); µm (micrometers); nm (nanometers); C (degrees Centigrade); α1,3GT (α1,3 galactosyltransferase); BSA (bovine serum albumin); ELISA (enzyme linked immunosorbent assay); HRP (horseradish peroxidase) IFNγ (interferon-γ); knockout (KO); mAb (monoclonal antibody); OD (optical density); OPD (ortho phenylene diamine); PBS (phosphate buffered saline); RBC (rabbit red blood cells);

Example 1

Production of α-Gal Liposomes and Binding of Anti-Gal

Exemplary α-gal liposomes are generated from extracts of rabbit red blood cell (RBC) membranes. These membranes are used since they contain glycolipids carrying from one to more than seven α-gal epitopes per molecule as disclosed in Eto et al., *Biochem.* (Tokyo) 64, 205, (1968); Stellner et al., *Arch. Biochem. Biophys.* 133, 464 (1973); Dabrowski et al., *J. Biol. Chem.* 259, 7648 (1984) and Hanfland et al., *Carbohydr. Res.* 178, 1 (1988), all of which are hereby incorporated by reference. However, α-gal liposomes may be produced from any natural or synthetic source of α-gal glycolipids upon addition of phospholipids in the presence or absence of cholesterol, after processing as described herein. As a non-limiting example, rabbit RBC are used at a volume of 0.25 liter packed cells. The RBC are lysed by repeated washes with distilled water. The rabbit RBC membranes are then mixed with a solution of 600 ml chloroform and 900 ml methanol for 20 h with constant stirring to dissolve the membrane glycolipids, phospholipids and cholesterol into the extracting solution. In contrast, proteins are denatured and are precipitating within and upon the membranes. Subsequently, the mixture is filtered to remove non-solubilized fragments and denatured proteins. The extract contains the rabbit RBC phospholipids, cholesterol and glycolipids, dissolved in the organic solution of chloroform and methanol (FIG. 2A). With the exception of the glycolipid ceramide tri-hexoside (CTH) having the structure Galα1-4Galβ1-4Glc-Cer, the glycolipids extracted from rabbit RBC membranes generally have 5 to more than 25 carbohydrate units in their carbohydrate chains with one or several branches, all of which are capped with α-gal epitopes. Rabbit RBC glycolipids were also reported to have 30, 35 and even 40 carbohydrate units with α-gal epitopes on their branched carbohydrate chains as provided for in Honma et al., *J. Biochem.* (Tokyo) 90, 1187 (1981), incorporated in its entirety by reference. The extract containing glycolipids, phospholipids and cholesterol is subsequently dried in a rotary evaporator. The amount of dried extract is approximately 300 mg per 0.25 liter of packed rabbit RBC.

Thirty ml of saline is added to the dried extract, which is then subjected to sonication in a sonication bath. This sonication process results in conversion of the extract into liposomes comprised of α-gal glycolipids, phospholipids and cholesterol, as schematically illustrated in FIG. 1A. Generally, α-gal liposomes may be of any size including, but not limited to, the range of 50 nanometer (nm) to 100 micrometer (m). Preferably, α-gal liposomes may have a size in the range of 0.1-20 µm, with an average size controlled by the length and intensity of the sonication process. Because the α-gal epitopes of many of the α-gal glycolipids protrude out of the liposomes, these epitopes readily interact with anti-Gal antibodies. This interaction results in activation of the complement cascade by anti-Gal binding to α-gal liposomes and the generation of C5a and C3a complement fragments, which in turn, form a chemotactic gradient that directs the migration of neutrophils, monocytes and macrophages from the circulation and from the peri-vascular space into the site of the α-gal liposome depot. The inflammatory cell infiltrate is readily observed in the histological sections of FIG. 6. The neutrophils and macrophages are capable of destroying microbial agents such as bacteria, viruses or fungi in the region of the injected α-gal liposomes. Macrophages have Fcγ receptors (FcγR) that bind to the Fc portion of IgG molecules that have bound to antigen. In this way, anti-Gal IgG molecules that bind to α-gal epitopes on the α-gal liposomes, also bind to FcγR on the recruited macrophages, as schematically illustrated in FIG. 1B. This interaction results in activation of the macrophage, internalization of the α-gal liposomes and secretion of a wide variety of growth factors, cytokines and chemokines to orchestrate the healing and remodeling of damaged tissue in part by recruiting fibroblasts and mesenchimal stem cells and stimulate proliferation of epithelial cells.

Figure 3A:
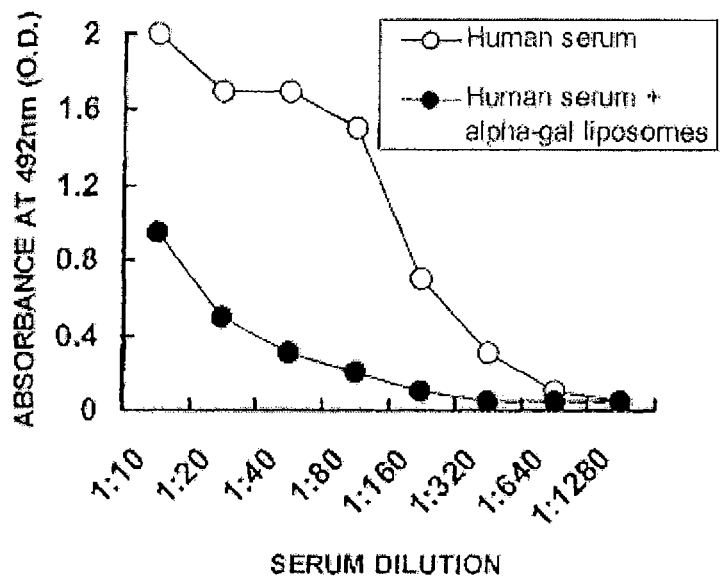
FIG. 3A shows a graph of the binding of anti-Gal to α-gal liposomes in suspension as demonstrated by neutralization of anti-Gal in human serum. Serum was incubated with 10 mg/ml α-gal liposomes for 2 h at 37° C. Subsequently, the serum was placed in ELISA wells (in serial two-fold dilutions starting at a serum dilution of 1:10) coated with synthetic α-gal epitopes linked to bovine serum albumin (α-gal BSA) as the solid-phase antigen. The anti-Gal within the serum that was not neutralized by the α-gal liposomes bound to the α-gal BSA-coated wells. Binding of anti-Gal to α-gal BSA was determined by the subsequent binding of rabbit anti-human IgG coupled to horseradish peroxidase (HRP) and color development with O-phenylene diamine (OPD). Human serum incubated in the presence (●) or absence (○) of α-gal liposomes is shown.

The specific binding of anti-Gal of human and mouse origin to the exemplary α-gal liposomes is graphically depicted in FIG. 3. Specifically, FIG. 3A shows the binding of anti-Gal to α-gal liposomes in suspension. When tested for binding to synthetic α-gal epitopes linked to bovine serum albumin (α-gal BSA) as solid-phase antigen, binding at a level higher than 1.0 optical density (OD) could be observed at serum dilutions of up to 1:80. However, if the serum was pre-incubated for 2 h at 37° C. with 10 mg/ml of α-gal liposomes, subsequent binding to the solid-phase α-gal BSA was less than 1.0 OD even at the lowest serum dilution of 1:10. This indicates that much of the serum anti-Gal binds to α-gal liposomes in suspension and therefore it is neutralized and is unavailable for the subsequent binding to the α-gal BSA as solid-phase antigen in the ELISA.

Figure 3B:
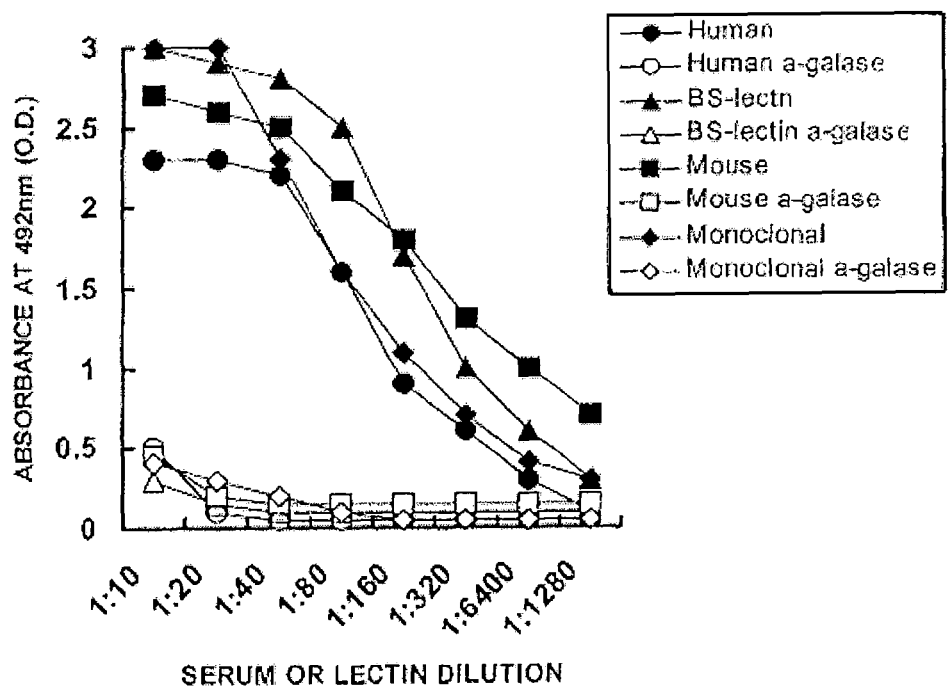
FIG. 3B shows a graph of the binding of serum anti-Gal to α-gal liposomes as solid-phase antigen. α-Gal liposomes (100 μg/ml) in phosphate buffered saline (PBS) were dried in ELISA wells. After blocking with 1% BSA in PBS, the α-gal epitopes on α-gal liposomes in control wells were specifically removed from the glycolipids carbohydrate chains by incubation for 1 h at 37° C. with 10 units/ml recombinant α-galactosidase (α-galase). Anti-Gal readily binds to α-gal epitopes on the α-gal liposomes, and is evident even at a serum dilution of 1:320 (●). Elimination of the terminal α-galactosyl unit by α-galactosidase results in complete elimination of the binding even at a serum dilution of 1:20 (○). Anti-Gal binding was evident in KO mouse serum dilution of 1:1280 (■), whereas treatment of α-gal liposomes with α-galactosidase resulted in elimination of >99% of anti-Gal binding (□). Similarly, the anti-Gal monoclonal antibody (mAb) M86 bound effectively to the α-gal liposomes (◇). No significant binding was observed in wells treated with α-galactosidase (○). The lectin *Bandeiraea simplicifolia* IB4 (BS lectin with starting concentration of 10 μg/ml) that binds specifically to α-gal epitopes was observed to bind to α-gal liposomes (▲), but not to these liposomes after they were treated with α-galactosidase (△).

Similarly FIG. 3B shows the binding of human and mouse anti-Gal to α-gal liposomes that serve as a solid-phase antigen in an ELISA. The α-gal liposomes were plated as 50 μl aliquots of a 100 μg/ml suspension in phosphate buffered saline (PBS) in ELISA wells and dried overnight. The drying results in the firm adhesion of the α-gal liposomes to the wells. The wells were subsequently blocked with 1% BSA in PBS. Human serum, α1,3galactosyltransferase (α1,3GT) knockout (KO) mouse serum containing anti-Gal antibody, and mouse monoclonal anti-Gal as disclosed in Galili et al., *Transplantation* 65, 1129 (1998), hereby incorporated by reference, were added to the wells. The α1,3GT KO mouse serum contains anti-Gal antibodies upon immunization of the mouse with pig kidney membranes as provided for in Tanemura et al., *J. Clin. Invest.* 105, 301 (2000), hereby incorporated by reference. After 2 h incubation, the wells were washed and binding of anti-Gal to α-gal liposomes was determined by the addition of the corresponding horseradish peroxidase (HRP) coupled anti-human, or anti-mouse secondary antibody followed by color reaction with ortho phenylene diamine (OPD). Anti-Gal readily binds to α-gal liposomes, with 1.0 OD value at a serum dilution of 1:160 (●). The specificity of the anti-Gal/α-gal liposome interaction was demonstrated be eliminating anti-Gal binding upon treatment of the α-gal liposomes coating the ELISA wells with recombinant α-galactosidase as disclosed in Stone et al., *Transplantation* 83, 201 (2007), incorporated herein by reference (○). The α-galactosidase enzyme cleaves the terminal galactose unit from the α-gal epitope, thereby destroying this epitope. Following such enzymatic treatment, the binding of anti-Gal to the liposomes could not be detected. The anti-Gal specific binding to α-gal liposomes was also demonstrated using serum from immunized KO mice (■), whereas treatment of the α-gal liposomes with α-galactosidase eliminated anti-Gal binding (□). Specific binding of α-gal epitopes by α-gal liposomes was also observed using an anti-Gal mAb from hybridoma cell supernatants (♦). As expected, the anti-Gal mAb did not bind to α-gal liposomes after treatment with α-galactosidase (◊). Similar specific binding to α-gal liposomes was observed with the α-gal epitope reactive lectin *Bandeiraea simplicifolia* IB4 (BS lectin) (▲) as provided for in Wood et al., *Arch. Biochem. Biophys.* 198, 1 (1979), incorporated herein by reference. The binding of this lectin was also abolished by treatment with α-galactosidase (Δ). These observations clearly demonstrate that the α-gal liposomes produced by sonication of chloroform/methanol extracts from rabbit RBC membranes, readily bind to anti-Gal antibodies. Although it is not necessary to understand the mechanism of an invention, it is believed that binding of anti-Gal to α-gal liposomes occurs in vivo at the injection site in subjects possessing anti-Gal antibodies.

Example 2

Binding of Anti-Gal to α-Gal Liposomes Induces Complement Activation

Figure 4A:
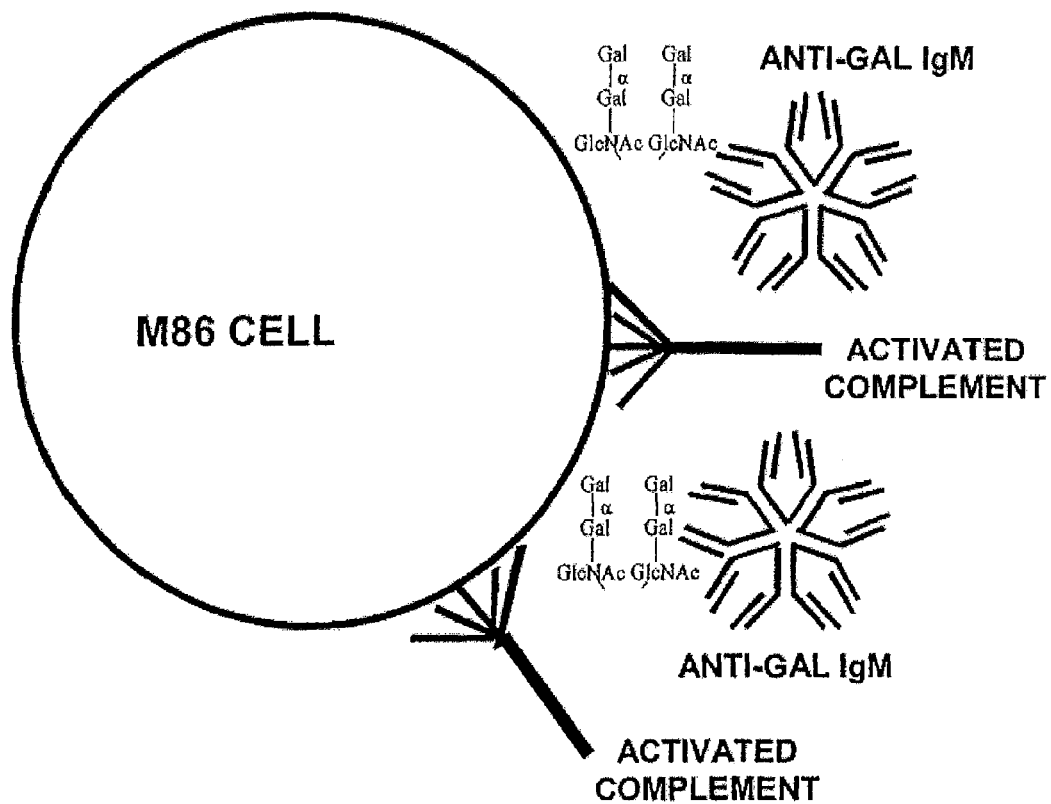
FIG. 4A shows a schematic for complement activity involving the lysis of the anti-Gal producing hybridoma cells M86.
Figure 4B:
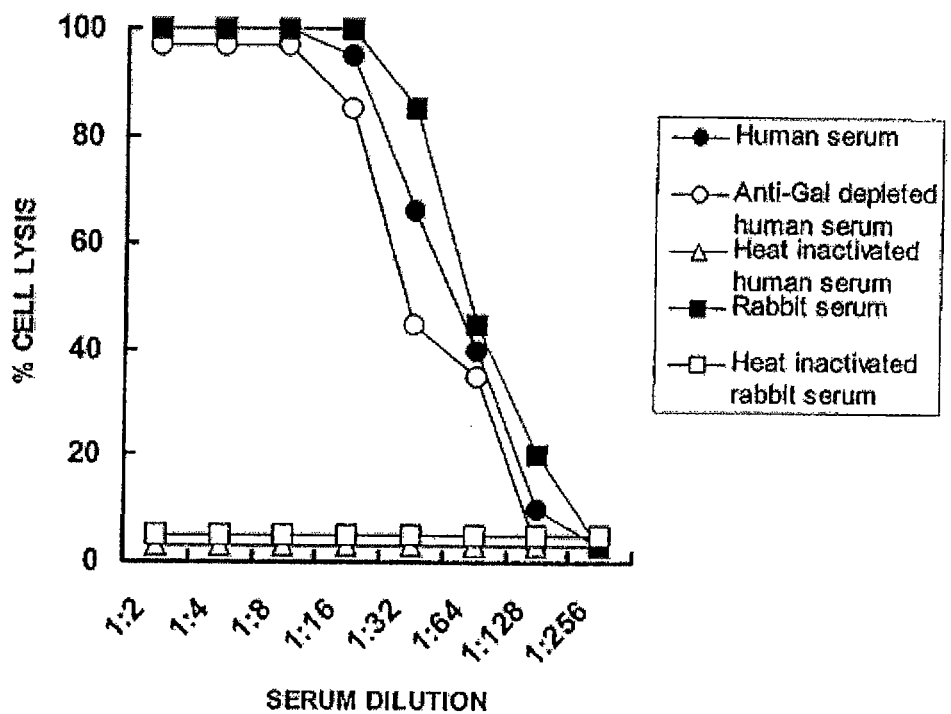
FIG. 4B provides a graph of showing the lysis of M86 cells by complement after incubation at 37° C. for 1 h.

This example describes the activation of complement within serum as a result of the binding of serum anti-Gal antibodies to α-gal epitopes on α-gal liposomes. Complement activation was observed herein by measuring the consumption of complement (e.g., loss of complement ability to lyse cells with bound antibodies). The binding of anti-Gal to α-gal epitopes on α-gal liposomes results in complement consumption due to conversion of the activated complement into complement fragments. The hybridoma cell line M86, which secretes an anti-Gal mAb, was used as a readout system for measuring complement mediated cytolysis (e.g., presence of complement in the serum). Since M86 cells express α-gal epitopes, the anti-Gal IgM mAb they produce bind to the α-gal epitopes on the hybridoma cell surface as schematically illustrated in FIG. 4A. When complement is added, it is activated by the anti-Gal bound to α-gal epitopes on the M86 cells, ultimately resulting in complement mediated lysis of the M86 cells as provided for in Galili et al., *Transplantation* 65, 1129 (1998), hereby incorporated by reference. Incubation of M86 cells with human serum at various dilutions, for 1 h at 37° C. (●) results in more than 40% lysis of the M86 cells even at a serum dilution of 1:64 (FIG. 4B). Lysis of M86 cells does not require exogenous anti-Gal since these cells have autologous anti-Gal bound to the α-gal epitopes of the cell surface. Thus, human serum depleted of anti-Gal also induces M86 lysis, due to the complement activity present in human serum (○). Anti-Gal depletion can be achieved by incubation of the human serum with glutaraldehyde fixed RBC, which express an abundance of α-gal epitopes. The adsorption of anti-Gal on fixed rabbit RBC was performed on ice to prevent complement activation during the adsorption process. Rabbit serum (which lacks anti-Gal like serum from all other nonprimate mammals) has complement and thus can lyse more than 40% M86 cells even at a dilution of 1:64. Incubation at 56° C. for 30 min of both human serum (Δ) and rabbit serum (□) results in inactivation of complement and hence loss of lytic activity (FIG. 4B).

Figure 4C:
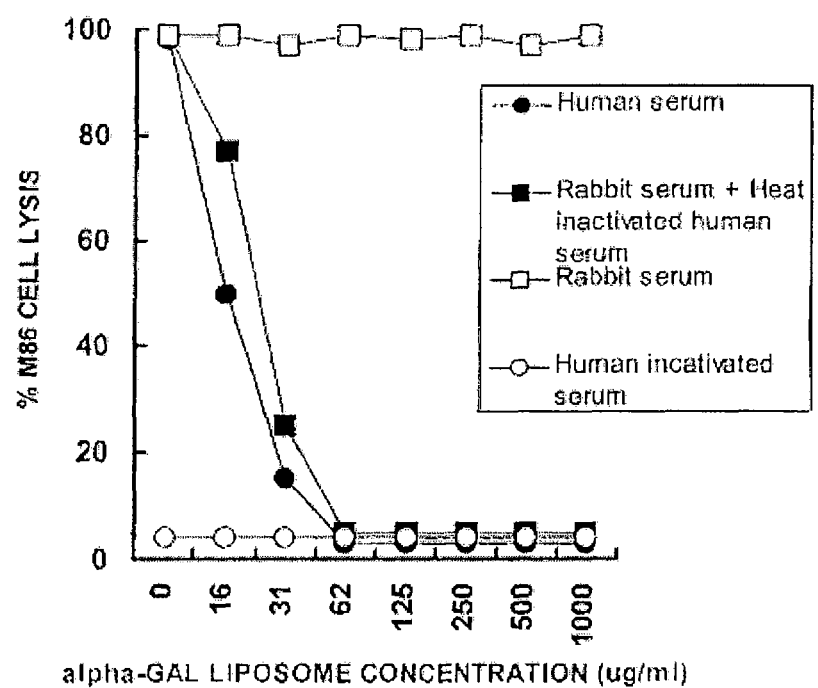
FIG. 4C provides a graph showing that interaction of human serum anti-Gal with α-gal liposomes results in complement consumption as measured by a loss of serum lytic activity. Human serum at a dilution of 1:10 was co-incubated with α-gal liposomes at various concentrations of the liposomes for 2 h at 37° C.

Addition of α-gal liposomes to the human serum diluted 1:10 for 30 min at 37° C., prior to addition of M86 cells, resulted in the loss of complement mediated cytolysis of the M86 cells even at a concentration of 62 μg/ml of the α-gal liposomes (FIG. 4C). Loss of lytic activity is presumed to occur as a result of the consumption of serum complement due to anti-Gal binding to α-gal liposomes. Thus, subsequent addition of M86 cells and incubation of the mixture for 1 h at 37° C. results in no significant M86 cell cytolysis, whereas in the absence of α-gal liposomes the complement in human serum lyses 100% of the M86 cells. Similarly, the complement in normal rabbit serum diluted 1:10 lyses more than 95% of M86 cells. However if the rabbit serum is incubated with α-gal liposomes and with heat inactivated human serum, no significant M86 lysis is observed when these cells are added to suspensions containing 62 μg/ml of α-gal liposomes. This lack of cell lysis is the result of the rabbit complement consumption due to the human anti-Gal binding to the α-gal liposomes and inactivation of the rabbit complement, prior to the addition of M86 cells. These data indicate that binding of anti-Gal to α-gal liposomes in vivo will also result in complement activation and therefore to the generation of C5a and C3a chemotactic factors, which is always part of the complement activation process.

Example 3

Induction of Monocyte and Macrophage Migration

Figure 5:
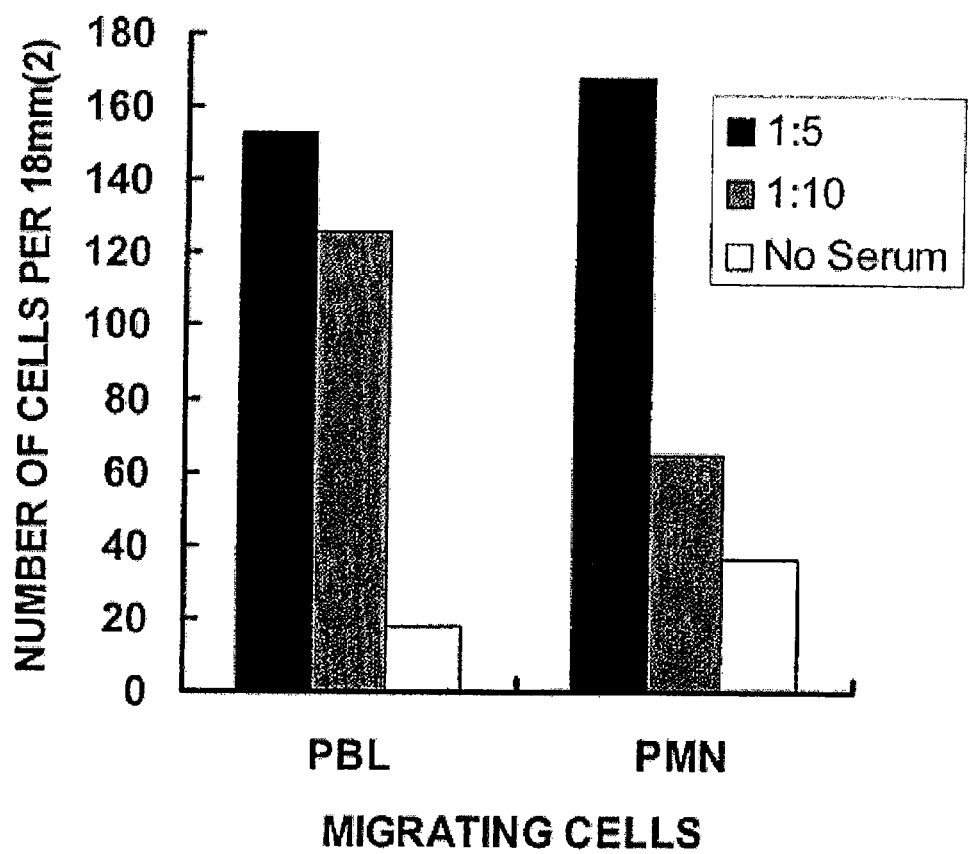
FIG. 5 shows the migration of human monocytes and neutrophils, or of mouse macrophages in response to chemotactic gradients generated by complement activation following anti-Gal binding to α-gal liposomes. The analysis was performed in a Boyden chamber system. This system includes two chambers, with the lower chamber containing human serum mixed with α-gal liposomes and the upper chamber containing various peripheral blood mononuclear cells (PBMC) or polymorphonuclear cells (PMN). The two chambers are separated by a porous filter (e.g., 8 μm pores), which permits the migration of cells between the chambers. The size of the migration area is 18 mm$^2$. After 24 h at 37° C. the filters were washed and stained, and the number of cells migrating toward the lower chamber were counted. The study was performed with 1×10$^6$ cells/ml in the upper chamber and serum diluted 1:5 and 1:10, mixed with 1 mg/ml of α-gal liposomes, in the lower chamber. Open columns indicate the number of migrating cells in the absence of serum; closed columns indicate the number of migrating cells with serum dilution 1:5; and gray columns indicate the number of migrating cells with serum dilution 1:10.

This example describes the chemotactic gradient generated by complement activation as a result of serum anti-Gal binding to α-gal liposomes. The generation of complement C5a and C3a chemotactic factors was assessed by monitoring the migration of monocytes and macrophages in a Boyden chamber. This system includes two chambers, a lower chamber containing serum mixed with α-gal liposomes and an upper chamber containing various white blood cells. The two chambers are separated by a porous filter that permits the migration of cells from the upper to the lower chamber via pores within the filter. At the end of a 24 h incubation period at 37° C. the filters are stained and the number of migrating cells (e.g., within lower chamber) is counted. The study was performed with $10^6$ cells/ml in the upper chamber and serum diluted 1:5 (black columns) or 1:10 (gray columns) and mixed with 1 mg/ml of α-gal liposomes in the lower chamber. A negative control solution in the lower chamber contained medium and α-gal liposomes, in the absence of serum, in order to assess the random migration of cells (open columns). As shown in FIG. 5, incubation of human peripheral blood lymphocytes (PBL) or polymorphonuclear cells (PMN) in the upper chamber and α-gal liposomes in the absence of serum in the lower chamber did not induce significant cell migration. However when serum and α-gal liposomes were mixed together in the lower chamber, extensive migration of mononuclear cells and neutrophils was observed toward the lower chamber. The morphology of the migrating cells in the PBL population indicated that the majority of the migrating cells were monocytes.

Example 4

Intradermal Recruitment of Neutrophils, Monocytes and Macrophages

In vivo studies on the effect of α-gal liposomes were performed in α-1,3galactosyltransferase knockout (KO) mice as provided for in Thall et al., *J. Biol. Chem.* 270, 21437-21442 (1995), incorporated in its entirety by reference, since these are the only non-primate mammals capable of producing anti-Gal antibodies. All other non-primate mammals express α-gal epitopes and thus do not produce anti-Gal antibodies. In order to monitor the in vivo effect of anti-Gal interaction with injected α-gal liposomes, KO mice producing anti-Gal (e.g., KO mice pre-immunized with 50 mg pig kidney membranes resulting in the induction of anti-Gal titers similar to those observed in humans) were injected intradermally with 1.0 mg α-gal liposomes in 0.1 ml saline.

Figure 6:
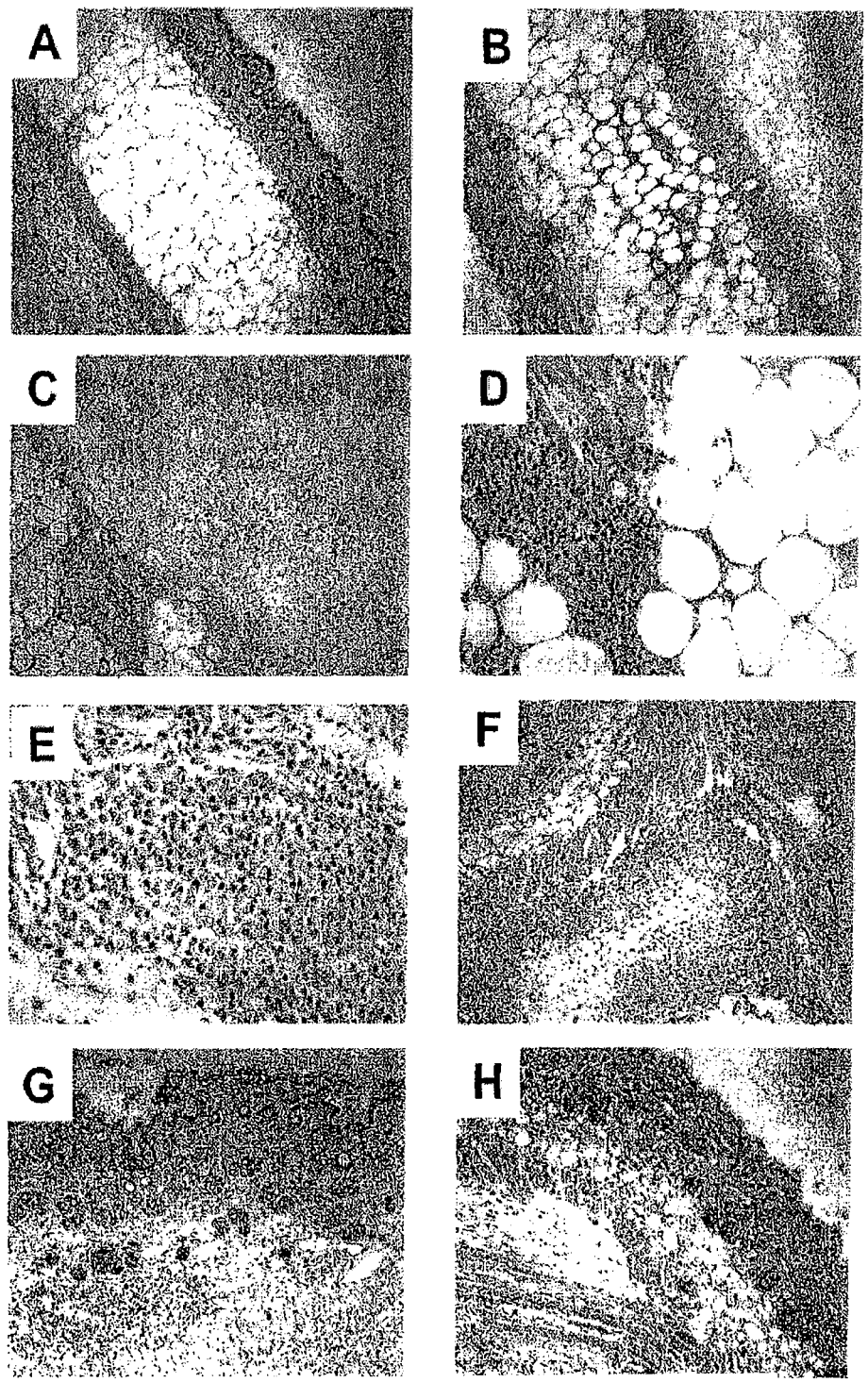
FIG. 6 depicts the in vivo induction of local inflammation by intradermal injection of α-gal liposomes in KO mice. The KO mice were immunized three times intraperitoneally with a homogenate of 50 mg pig kidney membranes to induce anti-Gal production. The KO mice were injected intradermally with 1 mg α-gal liposomes suspended in 0.1 ml saline, and euthanized at different time points post-injection. Skin specimens at the injection site were removed, sectioned, stained with hematoxyllin-eosin (H&E) and inspected microscopically. Some of the sections include the epidermis layer as point of reference.

Skin specimens from the injection site were obtained at different time points, fixed, stained with hematoxyllin-eosin (H&E) and inspected under a light microscope. FIG. 6A depicts normal skin prior to injection of α-gal liposomes. The epidermis comprises of one to two layers of epithelial cells. The dermis contains fibroblasts under the epidermal layer, fat cells as a deeper layer and an underlying narrow layer of muscle cells and fibroblasts. No inflammatory cells are observed in the normal skin (×100). FIG. 6B depicts the skin 12 h after injection of 1.0 mg α-gal liposomes. The intradermal injection site is identified as the area with the least amount of cells, under the muscle cell layer. Note that at this early time point the injection area is filled with neutrophils that surround the injected site both within the fat cell layer and within the side adjacent to the epidermis (×100). FIG. 6C also depicts the skin 12 h post-injection. The α-gal liposome depot of the injection site is shown in the center of image, which is bordered on the left by the fat cell layer. The α-gal liposome injection site has a low density of dermal cells. However, by 12 h post-injection, the injection site has become populated by infiltrating inflammatory cells presumably recruited by the injected α-gal liposomes bind to anti-Gal antibody and complement activation. A higher magnification of the infiltrating cells within the fat cell area in FIG. 6D (×400) indicates that the infiltrating cells are neutrophils. The extensive migration of neutrophils into the α-gal liposome injection site is followed by migration of monocytes and macrophages, which are recruited by the locally produced complement chemotactic factors. FIG. 6E depicts the α-gal liposome injection site 48 h post-injection. As shown in this higher magnification (×400) most of the infiltrating inflammatory cells in the injection site are mononuclear cells with nuclear features resembling macrophages (e.g., kidney shaped nuclei). These cells are evident in the injection site already 24 h post-injection. The characterization of these cells as macrophages is further described in Example 6 below. FIG. 6F depicts the α-gal liposome injection site 5 days post-injection. By this time the injection site is filled with large round macrophages, reflecting the local activation of the infiltrating macrophages due to the interaction of the anti-Gal opsonized α-gal liposomes. Only the center of the injection site is devoid of macrophages, and likely functions as an α-gal liposome depot. The epidermis in this figure is shown in the upper left corner. As shown in FIG. 6G, infiltrating macrophages are detectable in the injection site as late as 14 days post-injection. As shown in FIG. 6H, macrophages completely disappear from the injection site by day 20 post-injection. The injection site at that stage is rich with fibroblasts and muscle cells, which are contemplated to have originated from myofibroblasts recruited by the macrophages activated by the anti-Gal opsonized α-gal liposomes. Nonetheless an understanding of the mechanism is not necessary in order to make and use the present invention. The histological analysis presented in FIG. 6 indicates that intradermal injection of α-gal liposomes is suitable for induction of a local inflammatory response. The localized inflammatory response is detectable within 12 h and is accompanied by extensive neutrophils infiltration, followed by a second wave of infiltrating monocytes and macrophages within 24-48 h post-injection. In skin wounds accompanied by microbial infection, the neutrophils and the macrophages recruited by the interaction between anti-Gal and the injected α-gal liposomes are contemplated to mediate the destruction of the infectious agent. In addition, the various growth factors, cytokines and chemokines secreted by the activated macrophages are contemplated to mediate wound healing and repair of the damaged tissue. Nonetheless an understanding of the mechanism(s) is not necessary in order to make and use the present invention.

Example 5

α-Gal Liposomes do not Elicit an Immune Response

Figure 7:
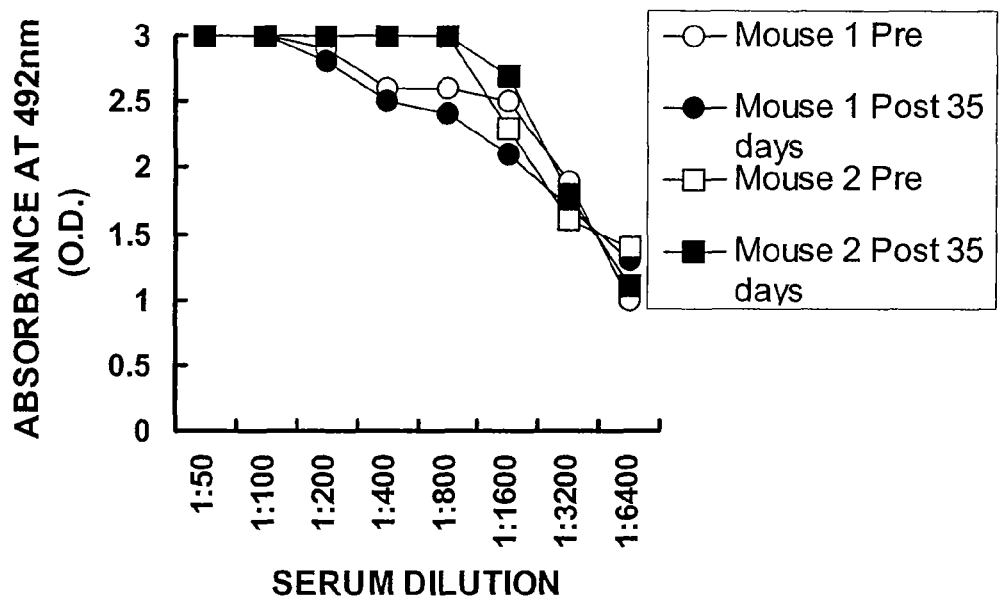
FIG. 7 provides a graph depicting the lack of antibody response to injected α-gal liposomes. The antibody response was measured in an ELISA with 50 μl of α-gal liposomes at concentration of 100 μg/ml dried in each well (solid phase antigen). The dried α-gal liposomes were subsequently blocked with 1% BSA in PBS. Serum samples from two representative mice obtained before and 35 days post intradermal injection (○, ● and □, ■), were tested for IgG binding to α-gal liposomes. No significant differences are observed in anti-α-gal liposomes IgG antibody activity in serum from mice obtained post α-gal liposome injection (closed symbols).

Although α-gal liposomes readily bind in vitro and in vivo to anti-Gal antibodies, they do not elicit an immune response against the injected α-gal liposomes as determined by ELISA. To demonstrate this, 50 μl of a solution containing α-gal liposomes at a concentration of 100 μg/ml were dried in ELISA wells to serve as a solid phase antigen. Serum samples from two representative mice obtained before (○ and □) and 35 days post intradermal injection (● and ■, respectively) were tested for IgG binding to α-gal liposomes. A humoral immune response against components of the α-gal liposomes should result in increased IgG binding to α-gal liposome-coated wells in post-injection serum (e.g., higher activity as compared to pre-injection serum). As shown in FIG. 7, the binding of IgG antibodies to α-gal liposomes 35 days post-injection was similar or lower to that observed prior to injection. Thus administration of α-gal liposomes does not elicit a deleterious humoral immune response against the injected material, despite their ability to recruit neutrophils, monocytes and macrophages to the injection site.

Example 6

Figure 8:
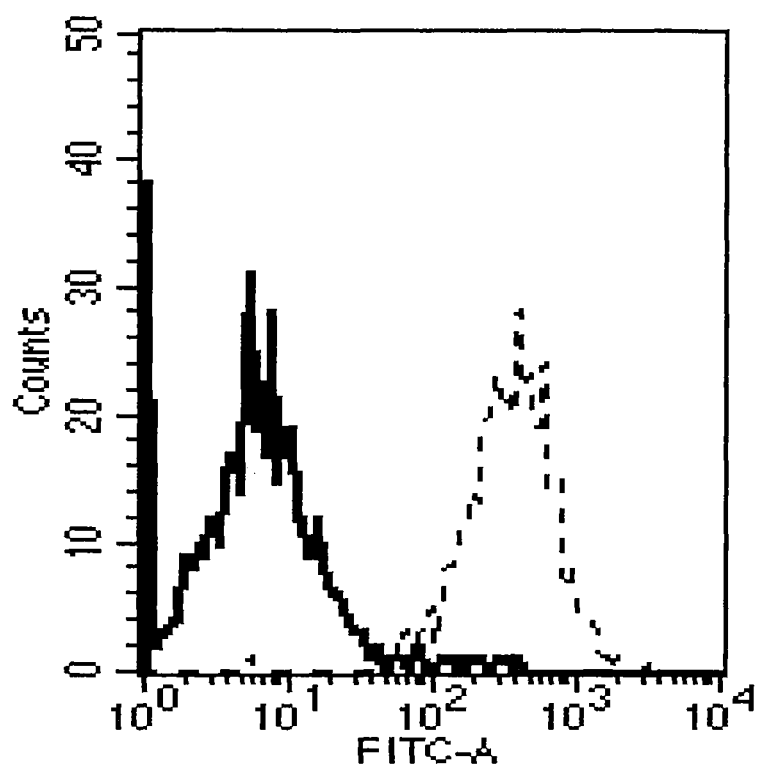
FIG. 8 provides exemplary data demonstrating in vivo recruitment of macrophages into polyvinyl alcohol (PVA) sponge containing α-gal liposomes. The sponge filled by soaking with α-gal liposome suspension (100 mg/ml) was implanted subcutaneously in α-1,3-galactosyltransferase knockout mice (KO mice) for 3 days, then removed. The infiltrating cells were obtained by repeated squeezing of the sponge in 1 ml PBS. The cells were stained with anti-CD 11b antibody (Pharmingen, Inc,) that specifically binds to macrophages and allows for the identification of macrophages by flow cytometry (FACS) analysis. Solid line—isotype control of cells stained only with the secondary FITC coupled anti-rat IgG antibody. Broken line—cells stained with monoclonal rat anti-mouse CD11b Ab, then with secondary fluorescein coupled anti-rat IgG antibody. Note the shift of the whole cell population to the right, implying that all cells migrating into the PVA sponge containing α-gal liposomes, are macrophages. A representative mouse is shown.

Recruitment of Macrophages into Polyvinyl Alcohol (PVA) Sponges by α-Gal Liposomes The objective in this study was to determine whether the mononuclear cells recruited by injected α-gal liposomes binding the anti-Gal antibody (FIG. 6) are macrophages that can be identified by immunostaining and analysis of stained cells by flow cytometry. This was performed by the use of subcutaneously implanted polyvinyl alcohol (PVA) sponge discs (PVA Unlimited, Inc., 10 mm diameter and 3 mm thickness). Prior to implantation, the discs were soaked in a suspension of α-gal liposomes (100 mg/ml). α1,3galactosyltransferase knockout mice (KO mice) were anaesthetized with 0.04 cc of ketamine/xylazine (50 mg/cc and 2.5 mg/cc, respectively). The dorsa of the mice are shaved and a 10 mm linear incision was made then implanted subcutaneously with the PVA disc soaked in α-gal liposome suspension. The wound was closed by suture. The PVA discs were removed from the mice 72 h post implantation. The present invention teaches that anti-Gal binds to the α-gal liposomes, activates complement and recruit inflammatory cells into the PVA sponge discs. The cells migrating in vivo into the PVA sponge discs were retrieved by repeated pressing on sponge discs immersed in PBS. Subsequently, the cells were washed, stained with the mouse monoclonal anti-CD11b macrophage specific antibody (Pharmingen Inc, CA) and subjected to flow cytometry (FACS). As shown in FIG. 8, all infiltrating cells were found to be macrophages, since all cells displayed shift to the right after staining with anti-CD 11b antibody (broken line) in comparison to isotype control (solid line). Thus, all infiltrating cells were stained positively with the macrophage specific monoclonal antibody. PVA discs soaked with saline and studied 3 days post implantation contained no measurable numbers of infiltrating cells.

Example 7

Effects of α-Gal Ointment Application on Wound Healing

The α-gal ointment is another composition containing α-glycolipids that can be used for accelerated wound healing by recruitment of macrophages to the damaged area. It is of particular beneficial use in skin burns. The α-gal ointment is prepared by mixing α-gal glycolipids with Vaseline or any other cream or gel at a final concentration ranging from 0.001% to more than 90% α-gal glycolipids. The α-gal glycolipids may or may not be purified from the mixture with phospholipids and cholesterol obtained by extraction from rabbit red blood cell membranes (described in Example 1). The α-gal ointment is applied topically onto such as, but not limited to skin burns. Burns may be caused by various injuries (e.g., hot objects, hot fluids or radiation). The illustration in FIG. 9 describes treatment of a burn with α-gal ointment. This treatment is applicable to other types of wounds as well. The natural anti-Gal antibody and complement proteins are among the serum proteins that leak from the damaged blood vessels into the burn area because of their high concentration in the serum. As illustrated in FIG. 9, the interaction of the natural anti-Gal antibody in the burn with the large amounts of α-gal glycolipids in the ointment induces local activation of the complement cascade, and thus, generates the complement fragments chemotactic fragments C5a and C3a that recruits macrophages to the area of this antibody binding to its antigen. This extensive recruitment of macrophages, which is much faster than the physiologic migration of macrophages into burns, results in accelerated debridement, epithelialization, fibroblasts migration and proliferation and collagen matrix deposition by the fibroblasts (fibroplasia), ultimately resulting in accelerated healing of burns and shorter morbidity than that achieved with current treatments. This treatment is applicable to various skin injuries where anti-Gal will leak from damaged capillaries and thus will interact with α-gal glycolipids within the applied α-gal ointment. α-Gal ointment may also be formed with ointments containing antibiotics (as those presently used for burns treatment), thus preventing infections while the healing process occurs. This treatment of topical application of α-gal glycolipids in an ointment formulation introduces no chemicals, other than the natural α-gal epitopes on glycolipids. Phospholipids and cholesterol, if present, are identical to those in human cells. Therefore, this treatment is likely to be safe. The safety of α-gal glycolipids is further implied from the fact that humans are constantly exposed to α-gal epitopes via a wide range of foods containing beef and pork meat, without any adverse effects.

Example 8

Binding of Anti-Gal to α-Gal Glycolipids in α-Gal Ointment

Figure 10:
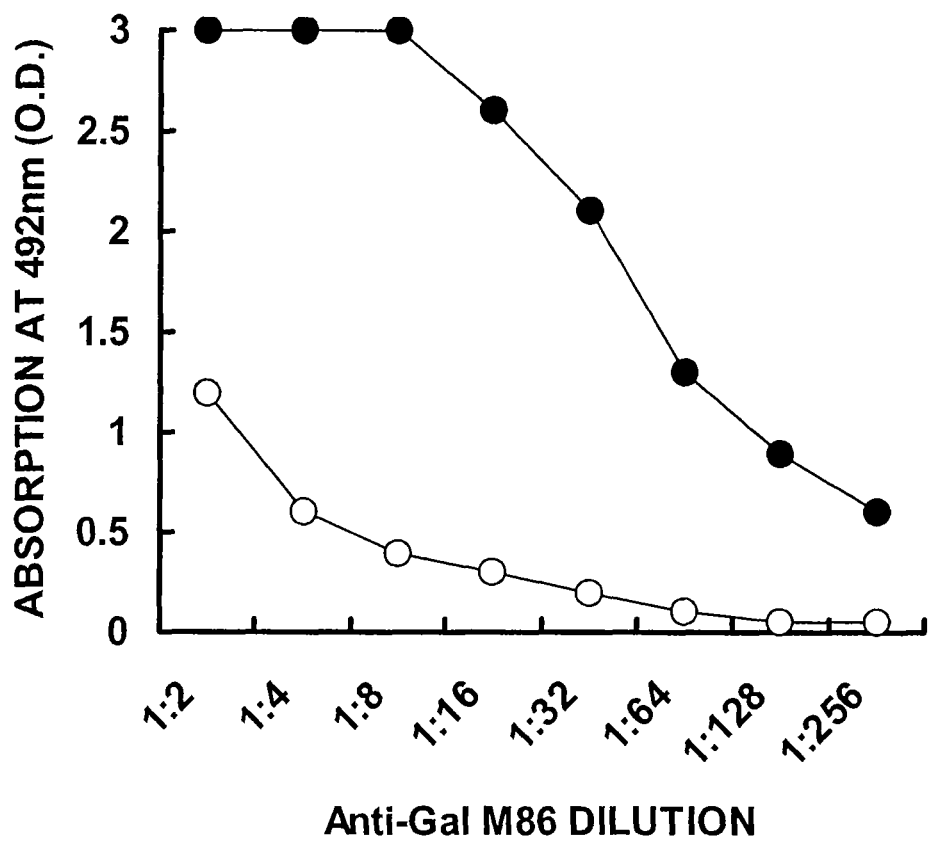
FIG. 10 demonstrates one embodiment of an interaction between an anti-Gal antibody and α-gal glycolipids within α-gal ointment. Neutralization of monoclonal anti-Gal following mixing with α-gal ointment (○), or Vaseline control lacking α-gal glycolipids (●). Anti-Gal activity was determined by subsequent binding to α-gal epitopes linked to BSA (α-gal BSA) as solid phase antigen in ELISA wells.

The interaction between the anti-Gal antibody and α-gal epitopes in α-gal ointment is demonstrated. The α-gal ointment can not be used as solid phase antigen in ELISA since it does not attach to ELISA wells. Thus, the accessibility of α-gal epitopes within the ointment to anti-Gal binding was tested by mixing of the monoclonal anti-Gal M86 antibody as provide for in Galili et al., *Transplantation* 65, 1129, 1998, hereby incorporated by reference, with the ointment at a 1:1 ratio (vol/vol) for 1 h at 37° C. Interaction of anti-Gal with α-gal epitopes in the ointment prevents (neutralizes) subsequent binding of the monoclonal anti-Gal antibody to α-gal epitopes on the synthetic α-gal epitopes linked to bovine serum albumin (α-gal BSA), which serves as solid phase antigen in ELISA. This provides a readout system for non-neutralized anti-Gal remaining active. Mixing the antibody preparations with Vaseline served as control for lack of α-gal epitopes, i.e. no binding of anti-Gal. α-Gal ointment neutralized >95% of the monoclonal anti-Gal M86 antibody mixed with the ointment as shown in FIG. 10. In the absence of α-gal glycolipids, Vaseline had no neutralizing effect on anti-Gal. This implies that anti-Gal in burn areas will readily bind to α-gal epitopes in α-gal ointment that is applied topically.

Example 9

Effect of α-Gal Ointment on Burn Healing Following Thermal Injury

Figure 11:
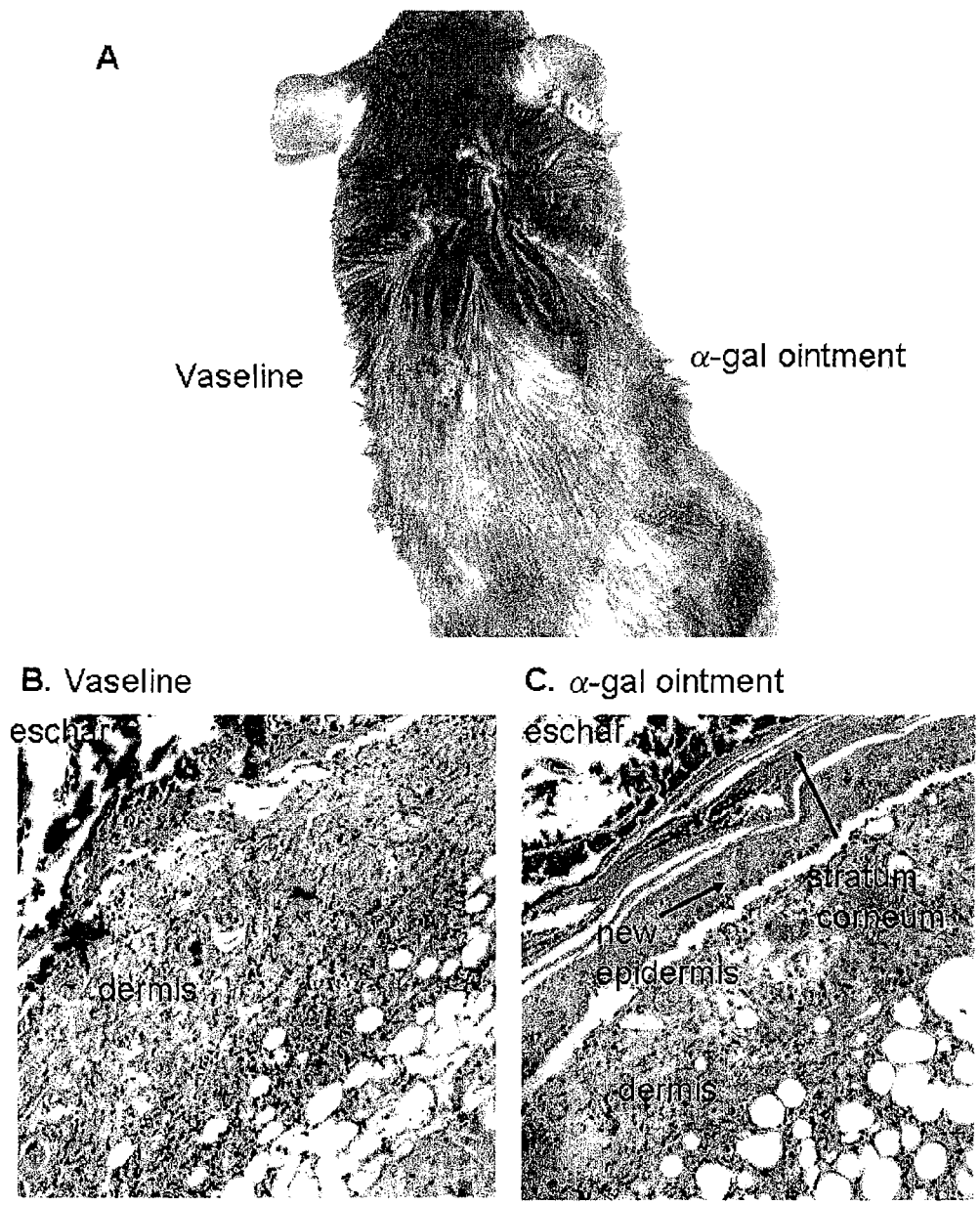
FIG. 11 provides exemplary data showing the effects of α-gal ointment on healing of burns induced by thermal injury to the skin. α1,3galactosyltransferase KO mice confirmed to produce anti-Gal in titers comparable to those in humans, were anesthetized and two burns were made on their backs by thermal injury with the heated bend end of a small metal spatula. One burn (left) was covered with Vaseline and the other (right) with α-gal ointment comprised of α-gal glycolipids mixed with Vaseline. Subsequently, burns were covered with small round band-aids. After six days the band-aids were removed from the burns. As shown in (A), the burn treated with α-gal ointment healed significantly faster than that with Vaseline and its size was ~50% of the Vaseline treated burn. Histological analysis of these burns demonstrated in the Vaseline treated burn (B) that the dermis was not covered by epidermis to replace the tissue damaged by the burn. The dark fragments on the skin are the damaged epidermis in the form of debris (crust) covering the wound and referred to as "eschar". The α-gal ointment treated wound (C) also has eschar caused by the burn. However, the skin is covered by a new multilayered epidermis comprised of epithelial cells covered by the keratinous layer (stratum corneum, stained-pink). Data are of one of 4 mice with similar results.

This section demonstrates the effects of α-gal ointment on healing of burns in α1,3galactosyltransferase knockout mice (KO mice) producing the anti-Gal antibody. KO mice were deeply anaesthetized with ketamine/xylazine injection and a superficial skin burn was caused in two sites on the back by brief touch with a heated end of a small metal spatula bend in the end (5 mm from the tip). Subsequently, α-gal ointment (FIG. 9) was applied topically to the right burn, whereas the left burn was covered with Vaseline lacking α-gal glycolipids. The left burn served as a control for healing of the burn in the absence of anti-Gal interaction with α-gal epitopes. The wounds were covered with circular band-aids. The mice (n=4) were euthanized on Day Six, the skin areas in the burn regions inspected and removed. The skin specimens were fixed with formalin and subjected to histological sections and hematoxyllin-eosin (H&E) staining (FIG. 11).

The burns were of the same size when formed by the heated edge of the metal spatula. However, after six days post-burn, the size of the damaged area treated by topical application of α-gal ointment, was approximately half the size of the control wound treated with Vaseline (FIG. 11A). Histological analysis of the control Vaseline covered burns revealed the absence of the epithelial cells of the epidermis (FIG. 11B). The presence of the debris comprised of dead tissue and granulocytes (eschar) is evident as dark fragments above the injured skin. A similar eschar is observed over the burn covered with α-gal ointment (FIG. 11C). However, the skin treated with α-gal ointment was completely covered at the burn area by a new epidermis consisting of several layers of epithelial cells, as well as a keratinous layer over this epithelial layer (stratum corneum) (FIG. 11C). These findings indicate that within a period of six days, the topical application of α-gal ointment results in complete regeneration of the top layer of the skin and the formation of an epidermis barrier that seals off the dermis from any microbial agent. It should be noted that at this early stage of burn healing, no skin appendages (e.g. hair shafts or sweat glands) are observed as yet. Overall, these findings imply that the histological analysis fits the gross morphology findings of accelerated healing of burns treated with α-gal ointment.

Example 10

Effects of α-Gal Liposome/Anti-Gal Antibody Application on Regeneration and Repair of Damaged Cartilage in Subjects with Osteoarthritis This example is aimed to study the efficacy of the compositions and methods of the present invention in recruitment of mesenchimal stem cells, or stem cells from any origin, for the healing and repair of damaged or injured tissues. In this example α-gal liposomes are injected into either the synovial cavity or the cartilage of human subjects having damaged articular cartilage in the joints, including but in no way limited to the knee joints of subjects with osteoarthritis. The α-gal liposomes are injected at any volume that is suitable for injection into the synovial cavity, with a preferred concentration ranging from 0.01 and 500 mg/ml. The injection is given once or several times in interval of one to several weeks. The anti-Gal antibody interaction with α-gal epitopes on α-gal liposomes results in activation of complement and local production of the complement fragments C5a and C3a, which are potent chemotactics. These factors induce recruitment of neutrophils, monocytes and macrophages into the synovial cavity or into cartilage, ultimately resulting in tissue repair. The Fcγ receptors on macrophages bind the Fe portion of anti-Gal coating the α-gal liposomes due to anti-Gal binding to α-gal epitopes on these liposomes. This Fc/Fcγ receptor interaction generates a signal that activates the macrophages recruited by the C5a and C3a chemotactic factors. Activated macrophages mediate debridement of the damaged cartilage and through secretion of growth factors and cytokines direct migration of stem cells that differentiate locally into chondroblasts in the damaged cartilage. The chondroblasts in turn secrete collagen and other cartilage matrix proteins and polysaccharides, resulting in repair and remodeling of the damaged articular cartilage within the treated joint. Similarly, macrophages activated by the binding of α-gal liposome/anti-Gal antibody complexes mediate debridement of the damaged bone and through secretion of growth factors and cytokines recruit osteoclasts and osteoblasts into the injection site for repair and remodeling of the damaged bone. By analogy, similar injection of α-gal liposomes into damaged heart tissue (myocardium) will result in local recruitment of monocytes/macrophages into the injection site and the subsequent secretion of growth factors and cytokines by these cells recruited into the injection sites. These growth factors and cytokines direct the migration of stem cells, either from the adjacent tissue or from another source, into the damaged tissue and further direct the subsequent repair and remodeling of the damaged heart tissue. Similarly, injection of α-gal liposomes into other damaged or inured tissues in the body may result in accelerated repair of the injury by recruitment of stem cells by a mechanism similar to that described above for the damaged articular cartilage treated with α-gal liposomes.

Example 11

Figure 12:
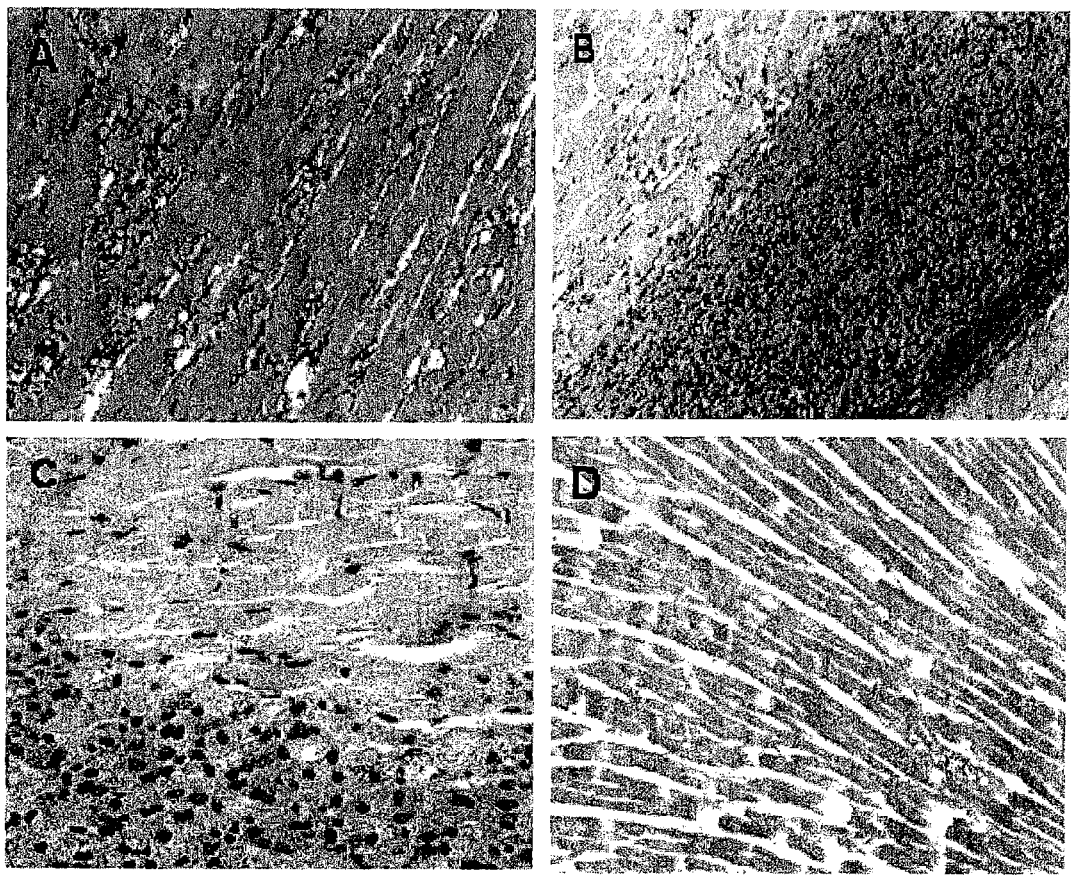
FIG. 12 provides exemplary data showing rapid recruitment of macrophages into ischemic heart muscle injected with α-gal liposomes in mouse heart implanted subcutaneously (Hematoxyllin & Eosin staining). Hearts removed from KO mice were injected into the myocardium with 2 mg α-gal liposomes, or with saline. Subsequently, the hearts were implanted subcutaneously in KO mice producing anti-Gal.

In Vivo Recruitment of Macrophages by α-Gal Liposomes Injected into Ischemic Heart Muscle This example demonstrates the ability of α-gal liposomes to recruit macrophages into the heart muscle. Hearts removed from KO mice were injected into the myocardium with 2 mg α-gal liposomes or with saline. Subsequently, the hearts were implanted subcutaneously in KO mice producing anti-Gal. Implanted hearts injected with saline and removed after 2 weeks contained necrotic cardiomyocytes and infiltrating neutrophils (FIG. 12A). After 4 weeks the heart implants disappeared due to the destruction of the organ. In contrast, myocardium specimens from implanted hearts that were injected with α-gal liposomes tissue maintained normal histological structure for 2 and 4 weeks and contained many recruited macrophages (FIGS. 12B and 12C). In addition, many of the recruited cells migrate into areas between the dead cardiomyocytes (FIG. 12C). All the nuclei visible in the sections are those of the infiltrating cells. This is indicated in FIG. 12D which describes an inner portion of the myocardium which lacks infiltrating cells. As seen in FIG. 12D (2 weeks post implantation of an α-gal liposomes injected KO mouse heart,) no nuclei are visible in the dead cardiomyocytes. Moreover, the myocardium in α-gal liposomes treated mice maintains its histological characteristics much better than saline injected hearts (FIGS. 12B-D, vs. FIG. 12A).

Example 12

Figure 13:
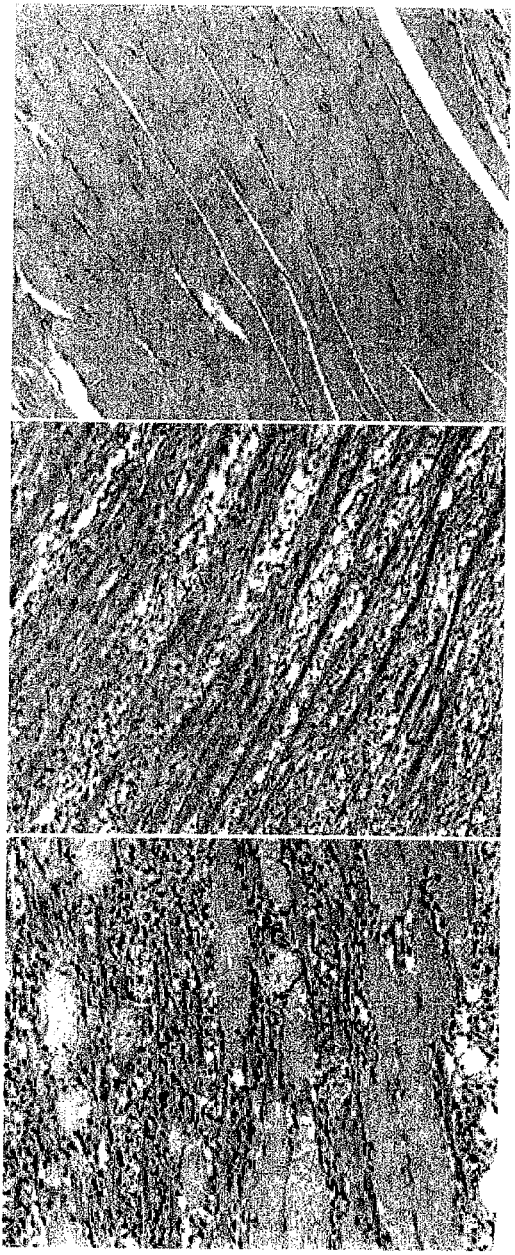
FIG. 13 presents exemplary data showing rapid infiltration of macrophages into ischemic leg muscle treated with α-gal liposomes by intramuscular injection of 10 mg α-gal liposomes. The study was performed in anti-Gal producing KO mice in which the blood flow is blocked in the right hind leg by applying a rubber band tourniquet over the leg. The tourniquet is removed after 4 h to allow for reperfusion of the leg blood vessels. The histology studies are performed in the leg muscle *Tibialis anterior.*

In Vivo Recruitment of Macrophages by α-Gal Liposomes into Ischemic Skeletal Muscle Another example for the in vivo recruitment of macrophages by α-gal liposomes is the injection of these liposomes into a KO mouse leg muscle by ischemia. The blood flow was blocked in the right hind leg of KO mice by applying a rubber band tourniquet over the leg according to a method previously described by Ott et al., *FASEB J* 19:106 (2005). The tourniquet was removed after 4 h to allow for reperfusion of the leg blood vessels. The histology studies are performed in the leg muscle (hind limb). The muscle fibers in an uninjured skeletal muscle comprise of muscle cell syncitia (myotubes), formed by fusion of myoblasts, with the nuclei in the periphery of the tubes. See, FIG. 13A. This ischemia results in death of the myotubes due to lack of oxygen. The resulting necrosis of the myotubes is clearly evident after 96 h. See, FIG. 13B. The specimen in FIG. 13B was injected with saline to serve as control to α-gal liposomes injection. At that time, many neutrophils infiltrate the necrotic tissue. The myotube syncitia decrease in their size and the nuclei of each myotube accumulate in a row. Subsequently, the dead myotubes are phagocytozed by debriding macrophages. Other ischemic leg muscles were injected with 10 mg α-gal liposomes immediately after removal of the tourniquet that prevented for 4 h blood flow into the muscle. Specimens obtained 4 days post α-gal liposomes injection (FIG. 13C) indicated that the tissue contained many more macrophages than the control tissue injected with saline (FIG. 13B). Moreover, the proportion of non-necrotic myotubes in the α-gal liposomes treated ischemic muscle was much higher than that in saline injected muscle, where the large majority of the myotubes are necrotic (FIGS. 13C vs. 13B respectively). These findings indicate that the injection of α-gal liposomes induces rapid recruitment of macrophages into the skeletal leg muscle and that the rapid migration of the macrophages into the injured tissue reduces the damage caused by ischemia to the muscle.

Example 13

In Vivo Recruitment of Stem Cells by α-Gal Liposomes

Figure 14:
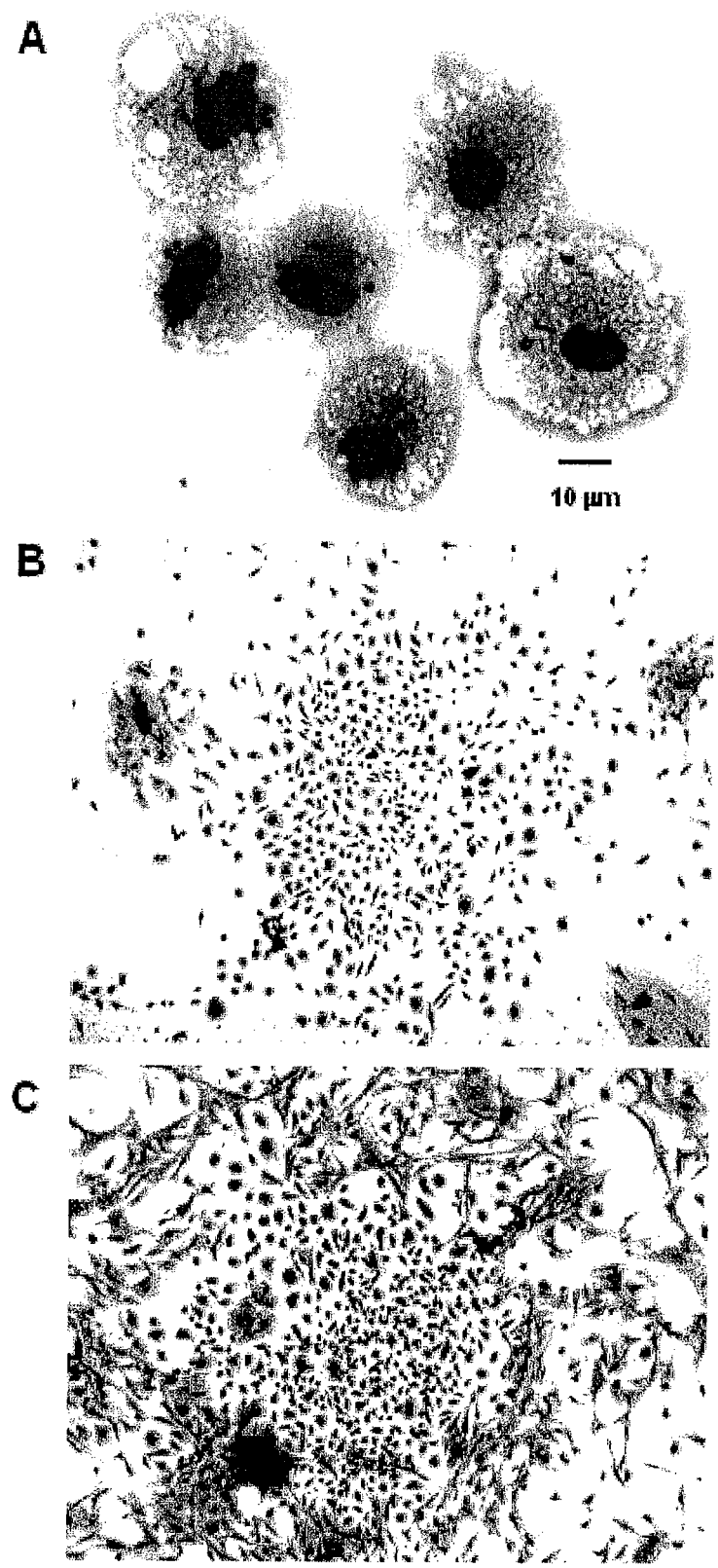
FIG. 14 presents exemplary data showing the presence of cells with stem cell potential among the macrophages recruited into polyvinyl alcohol (PVA) sponge discs by anti-Gal/α-gal liposomes interaction. In view of the ability of stem cells to proliferate in vitro and form cell colonies, the cells migrating into implanted PVA sponge discs, due to chemotactic factors generated by anti-Gal/α-gal liposomes interaction, were tested for the ability to form colonies in vitro. The cells infiltrating into the implanted PVA sponge discs were retrieved and cultured in vitro on round cover slips in tissue culture wells for 5 days. Subsequently, the cover slips were stained with Wright staining.

This example addresses the question of whether the population of macrophages recruited by α-gal liposomes also includes stem cells. Infiltrating macrophages were retrieved from PVA sponge discs containing 10 mg α-gal liposomes that were implanted subcutaneously for 6 days. The macrophages were retrieved by repeated squeezing of the sponge disc in phosphate buffered saline (PBS) and are presented in FIG. 14A. These cells were cultured in vitro on cover slips for 5 days in DMEM medium containing 10% fetal calf serum. Subsequently the cover slips were washed and stained with Wright staining. As shown in FIGS. 14B and 14C, cells which are recruited into PVA sponge discs containing α-gal liposomes, included, in addition to the migrating macrophages, also cells that display an extensive ability to proliferate (200-500 cells per colony formed from one cell within a period of 5 days). The frequency of these colony forming cells among cultured macrophages from PVA sponges to be 3-5 cells/$10^5$ macrophages. This is a similar frequency as that of mesenchimal stem cells in the bone marrow reported by Eisenberg et al., *Stem Cells* 24:1236 (2006). The ability to proliferate (i.e. self renew) and form colonies is one of the main characteristics of stem cells. These findings indicate that the macrophages recruited by anti-Gal/α-gal liposomes interaction, include also cells that have stem cell potential.

Example 14

Regeneration of Injured Brain Tissue by Treatment with α-Gal Liposomes

This example is aimed to study the efficacy of the compositions and methods of the present invention in recruitment of stem cells, for the healing and repair of damaged or injured brain tissue. In this example α-gal liposomes are injected intracranial into areas in the brain of human subjects having damage such as, but not limited to ischemia following infarct in one or more of the blood vessels in the brain. The α-gal liposomes are injected at any volume that is suitable for injection into the injured brain tissue and at a concentration ranging between 0.01 and 500 mg/ml. The interaction between the injected α-gal liposomes and the anti-Gal antibody activates complement and the generated chemotactic complement cleavage peptides recruit monocytes and macrophages to the injection site. The macrophages are activated by Fc/FcγR interaction with anti-Gal coated α-gal liposomes and secrete cytokines and growth factors that promote healing of the injured brain tissue and recruit stem cells. These stem cells proliferate and differentiate in to brain cells that repair and regenerate the injured brain tissue.

Example 15

Regeneration of Injured Peripheral Nerve or Injured Spinal Cord by Treatment with α-Gal Liposomes This example is aimed to study the efficacy of the compositions and methods of the present invention in recruitment of stem cells, for the healing and repair of damaged or injured peripheral nerve or spinal cord. In this example α-gal liposomes at a concentration ranging between 0.01 and 500 mg/ml are injected into the injured spinal cord or in the injured nerve. An alternative approach is that the injured spinal cord or peripheral nerve is surrounded by a device containing α-gal liposomes at a concentration ranging between 0.01 and 500 mg/ml. This device can be in the form of a gel, plasma or fibrin clot surrounding part or the whole injured nerve tissue or spinal cord. Alternatively, collagen sheet or any biodegradable or non-biodegradable sheet containing the α-gal liposomes or having on its surface α-gal liposomes and which can be shaped into a tube around the injured nerve or spinal cord, can be used to apply the α-gal liposomes around the injured nerve or the injured spinal cord. The interaction between the injected α-gal liposomes and the anti-Gal antibody activates complement and the generated chemotactic complement cleavage peptides recruit monocytes and macrophages to the injection site. The macrophages are activated by Fc/FcγR interaction with anti-Gal coated α-gal liposomes and secrete cytokines and growth factors that promote extension of the damaged axons for reconnecting with the distal portion of the damaged neurons. Alternatively, the stem cells recruited by these cytokines and growth factors proliferate and differentiate in to nerve cells that promote regeneration of the injured nerve tissue in the peripheral nerve and/or in the spinal cord. Injection of α-gal liposomes into the retina, lens, or cornea of the eye could be beneficial in the recruitment of stem cells that repair damages in these tissues of the eye.

Example 16

Treatment of Diabetic Patients by Injection of α-Gal Liposomes into the Pancreas This example is aimed to study the efficacy of the compositions and methods of the present invention in recruitment of stem cells, for regenerating the activity of Langerhans Islets in the pancreas of diabetic patients. In patients with Type I diabetes and in some of the patients with Type II diabetes the Langerhans Islets have been destroyed. The proposed treatment aims to restore biologically active Langerhans Islets in the pancreas of these patients, thereby provide endogenous insulin and cure the state of diabetes. In this example, α-gal liposomes at a concentration ranging between 0.01 and 500 mg/ml are injected into the pancreas by endoscopy ultrasound, or by laparoscopy or by any other procedure which enables for direct injection of the α-gal liposomes into the pancreas. The interaction between the injected α-gal liposomes and the anti-Gal antibody activates complement and the generated chemotactic complement cleavage peptides recruit monocytes and macrophages to the injection site. The macrophages are activated by Fc/FcγR interaction with anti-Gal coated α-gal liposomes and secrete cytokines and growth factors that recruit stem cells. These stem cells and/or stem cells originating from macrophages proliferate and differentiate into Langerhans Islet cells that form the islets and secrete endogenous insulin.

Example 17

Treatment of Patients with Injuries in the Gastrointestinal Track by Injection of α-Gal Liposomes This example is aimed to study the efficacy of the compositions and methods of the present invention in recruitment of stem cells, for repair and regeneration of the gastrointestinal wall in patients with ulcer and other injuries to the gastrointestinal tract. The non-limiting example here is of ulcers in the stomach. This described treatment is applicable to any damage to the wall at any part of the gastrointestinal tract. The injured area is injected with α-gal liposomes at a concentration ranging between 0.01 and 500 mg/ml. The interaction between the injected α-gal liposomes and the anti-Gal antibody activates complement and the generated chemotactic complement cleavage peptides recruit monocytes and macrophages to the injection site. The macrophages are activated by Fc/FcγR interaction with anti-Gal coated α-gal liposomes and secrete cytokines and growth factors that recruit stem cells and promote the repair of the injured tissue. The recruited stem cells proliferate and differentiate into cells that replace the injured cells and repair the damaged gastrointestinal wall at the injection site.

Example 18

Treatment of Patients with Injuries Blood Vessels by α-Gal Liposomes

This example is aimed to study the efficacy of the compositions and methods of the present invention in recruitment of stem cells, for repair and regeneration of the blood vessel wall in patients with damaged blood vessels or in anastomoses of blood vessels by the use of α-gal liposomes. The injured blood vessel is surrounded by a device containing α-gal liposomes at a concentration ranging between 0.01 and 500 mg/ml. This device can be in the form of a gel, plasma clot or fibrin clot surrounding part or the whole injured blood vessel. Alternatively, collagen sheet or any biodegradable or non-biodegradable sheet containing the α-gal liposomes or having on its surface α-gal liposomes and which can be shaped into a tube around the injured blood vessel can be used to apply α-gal liposomes around the injured blood vessel. The interaction between the injected α-gal liposomes and the anti-Gal antibody activates complement and the generated chemotactic complement cleavage peptides recruit monocytes and macrophages to the injection site. The macrophages are activated by Fc/FcγR interaction with anti-Gal coated α-gal liposomes and secrete cytokines and growth factors that promote the repair of the injured blood vessel wall. These secreted cytokines and growth factors also recruit stem cells that proliferate and differentiate into cells that enable the regeneration of the intact blood vessel wall. Some of the recruited macrophages, which have stem cell potential, also may transdifferentiate into cells that repair the injured blood vessel.

In summary, the present invention provides numerous advantages over the prior art, including methods and compositions for the accelerated healing of wounds, repair and regeneration of injured tissues. All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in diagnostics, cell culture, and/or related fields are intended to be within the scope of the present invention.

Example 19

Wound Healing Using Topically Applicants α-Gal Liposomes

Materials

Rabbit red blood cells (RBC) and pig kidneys were purchased from PelFreez (Rogers, Ark.). Pig RBC from α1,3galactosyltransferase knockout pigs (KO pigs) were a generous gift from Fios Therapeutics. Peroxidase (HRP) coupled goat anti-mouse IgG and IgM antibodies were purchased from Accurate Chemicals (Westbury, N.Y.), HRP coupled F4/80 anti-mouse antibody from Caltag (Invitrogen, Md.) and rhodamin coupled antibodies for CD 11b from Pharmingen (San Diego, Calif.). HRP coupled rabbit anti-human IgG antibodies were purchased from Dako (Copenhagen, Denmark). FITC coupled Bandeiraea (Griffonia) simplicifolia IB4 lectin (BS lectin) was purchased from Vector Labs (Burlingame, Calif.). Cobra venom factor (CVF) was purchased from Sigma (St. Louis, Mo.).

Preparation of α-Gal Liposomes and Liposome Wound Dressings

α-gal glycolipids comprise the majority of glycolipids in these RBC. Galili et al., 2007 "Intratumoral injection of α-gal glycolipids induces xenograft-like destruction and conversion of lesions into endogenous vaccines" *J. Immunol.* 178: 4676-4687; Eto et al., 1968 "Chemistry of lipids of the posthemolytic residue or stroma of erythrocytes. XVI. Occurance of ceramide pentasaccharide in the membrane of erythrocytes and reticulocytes in rabbit" *J. Biochem.* (*Tokyo*) 64:205-213; Stellner et al., 1973 "Determination of aminosugar linkage in glycolipids by methylation. Aminosugar linkage of ceramide pentasaccharides of rabbit erythrocytes and of Forssman antigen" *Arch. Biochem. Biophys.* 133: 464-472; Dabrowski et al., 1984 "Immunochemistry of Vi-active oligo- and polyglycosylceramides from rabbit erythrocyte membranes. Determination of branching patterns of a ceramide pentadecasaccharide by 1H nuclear magnetic resonance" *J. Biol. Chem.* 259:7648-7651; and Egge et al., 1985 "Immunochemistry of Pi-active oligo- and polyglycosylceramides from rabbit erythrocyte membranes. Characterization of linear, di-, and triantennary neolactoglycosphingolipids" *J. Biol. Chem.* 260: 4927-4935; Hanfland et al., 1988 "Structure elucidation of blood group B-like and I-active ceramide eicosa- and pentacosasaccharides from rabbit erythrocyte membranes by combined gas chromatography-mass spectrometry; electron-impact and fast-atom-bombardment mass spectrometry; and two-dimensional correlated, relayed-coherence transfer, and nuclear Overhauser effect 500-MHz 1H-n.m.r. spectroscopy" *Carbohydr. Res.* 178:1-21; and Honma et al., 1981 "Isolation and partial structural characterization of macroglycolipid from rabbit erythrocyte membranes" *J. Biochem.* (*Tokyo*). 90:1187-1196. Therefore, α-gal liposomes were prepared from rabbit RBC membranes. Abdel-Motal et al., 2009 "Mechanism for increased immunogenicity of vaccines that form in vivo immune complexes with the natural anti-Gal antibody" Vaccine 27:3072-3082; and Galili et al., 2010 "Accelerated healing of skin burns by anti-Gal/α-gal liposomes interaction" Burns 36:239-251. Batches of 1 liter rabbit RBC were lysed in water and washed repeatedly to remove hemoglobin. For the extraction process, rabbit RBC membranes (RBC ghosts) were mixed with 1000 ml chloroform and 1000 ml methanol (1:1 chloroform:methanol) for 2 h, then 1000 ml methanol was added for overnight incubation with constant stirring (1:2 chloroform:methanol). The extract was filtered under vacuum through Whatman filter paper for removing residual RBC membranes and precipitated proteins. The membrane extract was dried in a rotary evaporator, and sonicated in saline in a sonication bath. The liposomes are spun at 1000 rpm for 10 min to remove precipitating materials which form a pellet. Supernatants containing liposomes were further centrifuged at 14,000 rpm and liposome pellets resuspended in the saline supernatant at a final concentration 100 mg/ml (10% vol/vol). These liposomes were extensively sonicated for 10 min using a sonication probe on ice within a laminar flow hood. The α-gal liposomes suspension is sterile because all proteins were denatured and removed in the chloroform:methanol extraction process and because of the sonication process. The liposomes are referred to as α-gal liposomes as they present an abundance of α-gal epitopes on their membranes.

Preparation of Control Liposomes Lacking α-Gal Epitopes

Control liposomes lacking α-gal epitopes were prepared from α1,3galactosyltransferase knockout pigs (KO pig) RBC. These aGT KO pigs lack α-gal epitopes because of targeted disruption (knockout) of the α1,3GT gene. Byrne et al., 2008 "Proteomic identification of non-Gal antibody targets after pig-to-primate cardiac xenotransplantation" Xenotransplantation 15:268-276. The KO pig RBC were received as a generous gift from Fios Therapeutics (Rochester, Minn.). Control KO pig liposomes were prepared by a method identical to the one described above for α-gal liposomes.

Breeding and Immunization of α1,3Galactosyltransferase Knockout Mice

Mice used in this study have disrupted (e.g., knockout) α1,3GT genes and are referred to as αGT knockout (aGT KO) mice. Thall et al., 1995 "Oocyte Gal α1,3Gal epitopes implicated in sperm adhesion to the zona pellucida glycoprotein ZP3 are not required for fertilization in the mouse" J. Biol. Chem. 270:21437-21440. The mice were generated in C57BL/6 genetic background and are bred and maintained at the animal facility of the University of Massachusetts Medical School. All experiments were performed with both male and female mice. Study protocols were approved by the UMass IACUC and are in compliance with national guidelines. Anti-Gal antibody production was elicited in KO mice by 3-4 weekly i.p. immunizations with 50 mg pig kidney membrane (PKM) homogenate, i.e. xenogeneic membranes expressing multiple α-gal epitopes. Production of anti-Gal antibody in KO mice was confirmed to be at titers similar to those observed in humans (i.e., for example, titers of between approximately 1:100 to 1:2000), by ELISA with α-gal BSA as solid phase antigen. Tanemura et al., 2000 "Differential immune responses to α-gal epitopes on xenografts and allografts: implications for accommodation in xenotransplantation" J. Clin. Invest. 105:301-310; Abdel-Motal et al., 2006 "Increased immunogenicity of HIV gp120 engineered to express α-gal epitopes" J. Virol. 80:6943-6951; and Abdel-Motal et al., 2009 "Mechanism for increased immunogenicity of vaccines that form in vivo immune complexes with the natural anti-Gal antibody" Vaccine 27:3072-3082.

Treatment of Excisional Skin Wounds with α-Gal Liposomes

Wounds were formed in shaved abdominal flanks of anesthetized KO mice. A 3×6 mm oval skin incision was made in the right abdominal flank of the mouse. The epidermis, dermis and upper part of the hypodermis were removed in the wound area created by this incision, resulting in the exposure of the connective tissue fascia over the panniculus carnosus muscle layer. Prior to treatment, 0.1 ml of the liposome suspension containing 10 mg α-gal liposomes was applied onto the pad (1×1 cm) of a small circular wound dressing ("spot" bandage, CVS Pharmacies) in a sterile laminar flow hood. The pads of the control wound dressings had either 0.1 ml saline or 10 mg KO pig liposomes applied. The wound dressing was applied to cover the wound and was further covered with Tegaderm™ and with Transpore™ adhesive tape (3M, St. Paul, Minn.) in order to prevent removal by the mouse.

Example 20

Preparation of Peritoneal Macrophages

KO mice were injected intraperitoneally (i.p.) with 1.5 ml of a 4% Brewer's thioglycolate solution. Macrophages (>99%) migrating into the peritoneal cavity were harvested after 7 days by i.p. injection of 10 ml PBS into euthanized mice and subsequent collection of the fluid from the peritoneal cavity.

Binding of anti-Gal antibody coated α-gal liposomes via Fc/FcγR interaction in macrophages was measured by flow cytometry. α-gal liposomes were coated with mouse anti-Gal IgG antibodies by 1 h incubation with KO mouse serum diluted 1:50. The liposomes (1 mg/ml) were washed and further incubated with mouse peritoneal macrophages for 1 h at 4° C. The cells were washed at 1000 rpm for removal of unbound liposomes then stained with rhodamin anti-CD11b antibody (macrophage specific) and with FITC-Bandeiraea (Griffonia) simplicifolia IB4 lectin (BS lectin) which binds to α-gal epitopes on the liposomes. After 30 min incubation, cells were washed, fixed and subjected to flow cytometry analysis. Macrophages incubated with non-antibody coated α-gal liposomes served as controls.

Example 21

Analysis of the Expression of Cytokine Genes Associated with Tissue Healing

Activation of macrophage genes encoding for cytokines associated with healing was evaluated in the skin of KO mouse skin 48 h post injection with 10 mg α-gal liposomes and in peritoneal macrophages, 24 h post i.p. injection of 30 mg α-gal liposomes.

Gene activation in the injected skin or in peritoneal macrophages was determined by quantitative real time-PCR (q-RT-PCR). Skin specimens from mice injected with saline or peritoneal macrophages from mice injected i.p. with saline served as controls in the corresponding studies. Custom made SABiosciences (Frederic, Md.) q-RT-PCR 96 well plates containing primers for 11 cytokine encoding genes and for the house keeping gene GADPH (glyceraldehydes-3-ophosphate dehydrogenase) were used for this purpose. The reaction was performed with SYBR Green® master mix solution (SABiosciences PA-011).

Expression of the following genes was measured: i) Fgf1 (fibroblast growth factor 1); ii) Ill1a (interleukin 1a); iii) IL6

(interleukin 6); iv) Pdgfb (platelet derived growth factor b); v) Tnf (tumor necrosis factor a); vi) Vegfa (vascular endothelial growth factor a); vii) Bmp2 (bone morphogenic protein 2); viii) Fgf2 (fibroblast growth factor 2); ix) Csf1 (colony stimulating factor 1); and x) Csf2 (colony stimulating factor 2).

Total RNA was isolated using gentle MACS (Myltenyi Extractor apparatus), followed by mRNA isolation and cDNA synthesis using Miltenyi Magnetic Micro Beads. The cDNA was added as ~1 ng per well to wells containing the various primers. PCR reaction (30 cycles) was performed in the Biorad MyiQ single color Real Time PCR detection system. The results were normalized based on the house keeping gene and fold increase in $C_t$ values (threshold concentration) determined by using the software program provided on SABioscience web site that calculates $DDC_t$ based fold change.

Example 22

Analysis of In Vitro Secretion of VEGF by Macrophages

Macrophages co-incubated with anti-Gal coated α-gal liposomes, or with α-gal liposomes not coated by anti-Gal antibody were plated in 24 well plates at $3 \times 10^5$ cells/ml/well. Macrophages cultured without liposomes served as control. Supernatants were collected after 24 h and 48 h and subjected to analysis of VEGF secretion using VEGF ELISA kit (Antigenix, N.Y.) according to the manufacturer's protocol.

Example 23

ELISA with Liposomes as Solid Phase Antigen

Binding of anti-Gal IgG in αGT KO mouse sera to α-gal liposomes and to αGT KO pig liposomes was studied in ELISA wells that were coated with these liposomes.

Liposomes in PBS (1 mg/ml) were dried in ELISA wells, resulting in firm attachment of the liposomes to the wells. After blocking with PBS containing 1% BSA, KO mouse serum samples at serial two-fold dilutions were placed as 50 ml aliquots in liposome coated wells and incubated for 2 h at 24° C. The wells were washed with PBS containing 0.05% Tween, and HRP coupled anti-mouse IgG antibodies added for 1 h. Color reaction was developed with ortho-phenylene diamine (OPD) and absorbance measured at 492 nm.

Example 24

Histological Analysis

Wound healing was determined in histological sections and expressed as percentage of wound surface covered with regenerating epidermis.

The wound bed was determined by the intact dermis. The number of infiltrating neutrophils and macrophages at skin sites injected with liposomes was determined by counting cells within a rectangular area demarcated in a microscope lens at 400× magnification. The rectangle with a size corresponding to 100×200 μm was placed at the border of the liposome hypodermic injection site within the skin. Neutrophils were identified by segmented nuclei and macrophages by the kidney or oval shaped nuclei and large size of the cells. Four fields were counted in each section. Two sections of the same specimen were evaluated. The data represent mean+SD from >5 mice/group.

Example 25

Statistics

A $Chi^2$ test was used for statistical analyses. A p-value<0.05 was considered statistically significant.

Example 26

Effect of α-Gal Liposomes on Healing of Burns in the Skin

This example demonstrates the effects of α-gal liposomes on healing of burns in the skin of α1,3galactosyltransferase knockout mice (KO mice) producing the anti-Gal antibody.

KO mice were deeply anaesthetized with ketamine/xylazine injection and a superficial skin burn was caused in two sites on the back by brief touch with a heated end of a small metal spatula bend in the end (5 mm from the tip).

The treatment was provided by topically applying 10 mg α-gal liposomes on a spot bandage pad (10×10 mm) to the right burn, whereas the left burn was covered with bandage containing saline. The left burn served as a control for healing of the burn in the absence of α-gal liposomes. The mice were euthanized on different time points, the skin areas in the burn regions inspected and removed. The skin specimens were fixed with formalin and subjected to histological sections and hematoxylin-eosin (H&E) staining for evaluating the extent of burn healing by measuring percent regeneration of epidermis. Galili et al., "Accelerated healing of skin burns by anti-Gal/α-gal liposomes interaction" *Burns* 36:239-251 (2010).

I claim:

1. A method, comprising:
   a) providing
      i) a subject having endogenous anti-Gal antibody and an injured tissue, and
      ii) a preparation comprising an α-gal epitope having a terminal α-galactosyl, and
   b) applying said preparation to said injury under conditions such that said injured tissue healing, repair and regeneration is accelerated.

2. The method of claim 1, wherein said terminal α-galactosyl is selected from the group consisting of Galα1-3Gal, Galα11-2Gal, Galα1-6Gal, α-galactose sugar units capable of binding anti-Gal antibodies and peptides mimetic to α-gal epitopes and capable of binding anti-Gal antibodies.

3. The method of claim 1, wherein said α-gal epitope is soluble.

4. The method of claim 1, wherein said α-gal epitope is attached to a molecule selected from the group consisting of a natural or synthetic glycolipid, glycoprotein, proteoglycan and a glycopolymer.

5. The method of claim 1, wherein said preparation further comprises an injury care device selected from the group consisting of syringes, adhesive bands, compression bandages, wound dressings, sponges, gels, ointments, creams, suspensions, solutions, semi-permeable films, plasma clots, biomaterials and fibrin clots.

6. The method of claim 1, wherein said preparation further comprises anti-Gal antibodies bound to said α-gal liposomes.

7. The method of claim 1, wherein said injured tissue is selected from the group consisting of skin tissue, brain tissue, nerve tissue, eye tissue, gastrointestinal tissue, skeletal muscle tissue, heart muscle tissue, connective tissue, cartilage tissue, bone tissue, endocrine glands and vascular tissue.

8. The method of claim 1, wherein said preparation comprises α-gal liposomes.

9. The method of claim 8, wherein said α-gal liposomes further comprise anti-Gal antibodies.

* * * * *